United States Patent
Umehara et al.

(10) Patent No.: US 10,400,165 B2
(45) Date of Patent: Sep. 3, 2019

(54) COLOR CONVERSION COMPOSITION, COLOR CONVERSION SHEET AND LIGHT SOURCE UNIT INCLUDING THE SAME, DISPLAY, LIGHTING APPARATUS, BACKLIGHT UNIT, LED CHIP, AND LED PACKAGE

(71) Applicant: TORAY INDUSTRIES, INC., Tokyo (JP)

(72) Inventors: Masaaki Umehara, Otsu (JP); Daisaku Tanaka, Otsu (JP); Hirotoshi Sakaino, Otsu (JP); Tsubasa Hamano, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 15/766,195

(22) PCT Filed: Sep. 30, 2016

(86) PCT No.: PCT/JP2016/079120
§ 371 (c)(1),
(2) Date: Apr. 5, 2018

(87) PCT Pub. No.: WO2017/061337
PCT Pub. Date: Apr. 13, 2017

(65) Prior Publication Data
US 2018/0305611 A1  Oct. 25, 2018

(30) Foreign Application Priority Data

Oct. 9, 2015 (JP) ................. 2015-200792
Feb. 8, 2016 (JP) ................. 2016-021572

(51) Int. Cl.
*H01L 33/50* (2010.01)
*C09K 11/06* (2006.01)
(Continued)

(52) U.S. Cl.
CPC ............... *C09K 11/06* (2013.01); *C07F 5/02* (2013.01); *C08K 5/3155* (2013.01); *C08K 5/47* (2013.01);
(Continued)

(58) Field of Classification Search
CPC ..... H01L 33/56; H01L 33/507; H01L 33/483; H01L 33/502; C09K 11/06;
(Continued)

(56) References Cited

U.S. PATENT DOCUMENTS 5,446,157 A    8/1995  Morgan et al.
6,221,517 B1   4/2001  Eida et al.
(Continued)

FOREIGN PATENT DOCUMENTS

EP    1816178 A1    8/2007
JP    08509471 A   10/1996
(Continued)

OTHER PUBLICATIONS

International Search Report and Written Opinion for International Application No. PCT/JP2016/079120, dated Dec. 27, 2016, 8 pages.
(Continued)

*Primary Examiner* — Roy K Potter
(74) *Attorney, Agent, or Firm* — RatnerPrestia

(57) ABSTRACT

A color conversion composition includes the following Component (A) and Component (B):
Component (A): an organic light-emitting material; and
Component (B): at least one of a polyester resin having a partial structure represented by General Formula (1) in its molecular structure of the polyester resin and a resin containing a bisphenol structure represented by General Formula (2):

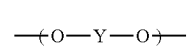

(1)

where Y is a divalent saturated aliphatic hydrocarbon group having at least one of a tertiary carbon and a quaternary carbon,
(Continued)

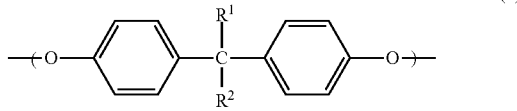

(2)

where $R^1$ and $R^2$ each represent hydrogen or a $C_{1-20}$ organic group; $R^1$ and $R^2$ may be the same as or different from each other.

24 Claims, 8 Drawing Sheets

(51) Int. Cl.
| | |
|---|---|
| F21V 9/30 | (2018.01) |
| C07F 5/02 | (2006.01) |
| C08L 67/03 | (2006.01) |
| C08L 71/08 | (2006.01) |
| F21S 2/00 | (2016.01) |
| G02B 5/20 | (2006.01) |
| H01L 51/50 | (2006.01) |
| C08K 5/315 | (2006.01) |
| C08K 5/47 | (2006.01) |
| C08K 5/55 | (2006.01) |
| C08K 5/56 | (2006.01) |
| C09K 11/02 | (2006.01) |
| G02F 1/00 | (2006.01) |
| G02F 1/13357 | (2006.01) |
| G02F 1/1335 | (2006.01) |
| H01L 51/52 | (2006.01) |

(52) U.S. Cl.
CPC .............. *C08K 5/55* (2013.01); *C08K 5/56* (2013.01); *C08L 67/03* (2013.01); *C08L 71/08* (2013.01); *C09K 11/02* (2013.01); *F21S 2/00* (2013.01); *F21V 9/30* (2018.02); *G02B 5/20* (2013.01); *G02F 1/00* (2013.01); *H01L 33/502* (2013.01); *H01L 51/50* (2013.01); *C09K 2211/1007* (2013.01); *C09K 2211/1011* (2013.01); *C09K 2211/1018* (2013.01); *C09K 2211/1022* (2013.01); *C09K 2211/185* (2013.01); *G02F 1/1336* (2013.01); *G02F 2001/133614* (2013.01); *H01L 33/501* (2013.01); *H01L 51/52* (2013.01)

(58) Field of Classification Search
CPC .... C09K 2211/1022; C09K 2211/1018; C09K 2211/1011; C09K 2211/1007; C08K 5/55; C08K 5/56; C08K 5/47; C08K 5/3155; F21V 9/30; G02F 1/1336

See application file for complete search history.

(56) References Cited

U.S. PATENT DOCUMENTS

| | | |
|---|---|---|
| 2001/0007412 A1 | 7/2001 | Eida et al. |
| 2004/0051781 A1* | 3/2004 | Kawaguchi ............ C09K 11/06 348/34 |
| 2012/0001217 A1 | 1/2012 | Kang et al. |
| 2013/0270591 A1 | 10/2013 | de Brouwer et al. |
| 2013/0307010 A1 | 11/2013 | Hikmet et al. |
| 2016/0272884 A1 | 9/2016 | Kim et al. |

FOREIGN PATENT DOCUMENTS

| | | | |
|---|---|---|---|
| JP | 08286033 A | 11/1996 | |
| JP | 2000208262 A | 7/2000 | |
| JP | 2001164245 A | 6/2001 | |
| JP | 2002348568 A | 12/2002 | |
| JP | 2002348568 A2 * | 12/2002 | ........... C08K 5/3437 |
| JP | 2006251076 A | 9/2006 | |
| JP | 2007273440 A | 10/2007 | |
| JP | 2010061824 A | 3/2010 | |
| JP | 2010276623 A | 12/2010 | |
| JP | 2011241160 A | 12/2011 | |
| JP | 2012022028 A | 2/2012 | |
| JP | 2014513865 A | 6/2014 | |
| JP | 2014136771 A | 7/2014 | |
| WO | 2001053065 A1 | 7/2001 | |
| WO | 2007088055 A1 | 8/2007 | |
| WO | 2015064864 A1 | 5/2015 | |

OTHER PUBLICATIONS

Japanese Office Action for Application No. 2016-561030, dated May 31, 2017 with translation, 6 pages.

Alvarez, M. et al., "Bichromatic laser emission from dipyrromethene dyes incorporated into solid polymeric media," Jun. 13, 2007, pp. 1-9, vol. 101, No. 113110, Sections I-II; Figures 1-3, Journal of Applied Physics.

Extended European Search Report for European Application No. 16 853 491.5, dated Apr. 16, 2019, 6 pages.

Singapore Written Opinion and Search Report for Singapore Application No. 11201802533R, dated May 7, 2019, 7 pages.

* cited by examiner

COLOR CONVERSION COMPOSITION, COLOR CONVERSION SHEET AND LIGHT SOURCE UNIT INCLUDING THE SAME, DISPLAY, LIGHTING APPARATUS, BACKLIGHT UNIT, LED CHIP, AND LED PACKAGE

CROSS REFERENCE TO RELATED APPLICATIONS

This is the U.S. National Phase application of PCT/JP2016/G079120, filed Sep. 30, 2016, which claims priority to Japanese Patent Application No. 2015-200792, filed Oct. 9, 2015 and Japanese Patent Application No. 2016-0215/2, filed Feb. 8, 2016, the disclosures of these applications being incorporated herein by reference in their entireties for all purposes.

TECHNICAL FIELD OF THE INVENTION

The present invention relates to a color conversion composition, a color conversion sheet and a light source unit including the same, a display, a lighting apparatus, a backlight unit, an LED chip, and an LED package.

BACKGROUND OF THE INVENTION

Application of a multicoloring technique by a color conversion method to liquid crystal displays, organic electroluminescence (EL) displays, lighting apparatuses, and the like is being energetically studied. Color conversion means converting light emission from a light-emitting body into light with a longer wavelength and means converting blue light emission into green or red light emission, for example.

A composition having this color conversion function (a color conversion composition) is formed into a sheet form and is combined with a blue light source, for example, whereby the three primary colors of blue, green, and red can be extracted, that is, white light can be extracted from the blue light source. A white light source obtained by combining the blue light source and the sheet having the color conversion function with each other forms a backlight unit, and this backlight unit, a liquid crystal drive part, and color filters are combined with each other, whereby a full-color display can be produced. Without the liquid crystal drive part, the residual part can be used as a white light source as it is, which can be used as the white light source such as LED lighting.

Improvement in color reproducibility is a problem in liquid crystal displays using the color conversion method. Narrowing the full width at half maximum of the respective emission spectra of blue, green, and red of the backlight unit to increase the color purity of each of blue, green, and red is effective in improving color reproducibility. To solve this problem, developed is a technique that uses quantum dots formed of inorganic semiconductor fine particles as a component of the color conversion composition (refer to Patent Literature 1, for example). Although the technique using the quantum dots indeed is narrow in the full width at half maximum of green and red emission spectra to improve color reproducibility, the quantum dots are vulnerable to heat and water and oxygen in the air and are thus deficient in durability on the other hand.

Also developed is a technique that uses a light-emitting material formed of an organic substance as a component of the color conversion composition in place of the quantum dots. Disclosed as examples of the technique that uses an organic light-emitting material as the component of the color conversion composition are one that uses a coumarin derivative (refer to Patent Literature 2, for example), one that uses a pyridine-phthalimide condensation product (refer to Patent Literature 3, for example), one that uses a rhodamine derivative (refer to Patent Literature 4, for example), and one that uses a pyrromethene derivative (refer to Patent Literature 5, for example).

CITATION LIST

Patent Literature

Patent Literature 1: Japanese Patent Application Laid-open No. 2012-22028

Patent Literature 2: Japanese Patent Application Laid-open No. 2007-273440

Patent Literature 3: Japanese Patent Application Laid-open No. 2002-348568

Patent Literature 4: Japanese Patent Application Laid-open No. 2001-164245

Patent Literature 5: Japanese Patent Application Laid-open No. 2011-241160

SUMMARY OF THE INVENTION

However, even these organic light-emitting materials are still insufficient in view of achieving both color reproducibility and durability. In particular, deficient is a technique that also achieves durability when an organic light-emitting material that exhibits light emission with high color purity is used as a component of a color conversion sheet.

A problem to be solved by the present invention is to achieve both improvement in color reproducibility and durability in a color conversion sheet for use in displays, lighting apparatuses, and the like.

The inventors of the present invention have found out that, the use of either one or both of a polyester resin having a specific structure and a resin containing a bisphenol structure having a specific structure as components of a binder resin in a color conversion composition inhibits the degradation of an organic light-emitting material and greatly improves the durability of a color conversion sheet.

To solve the problem described above and to achieve the object, a color conversion composition according to the present invention converts incident light into light with a wavelength longer than that of the incident light. The color conversion composition includes the following Component (A) and Component (B):

Component (A): an organic light-emitting material; and

Component (B): at least one of a polyester resin having a partial structure represented by General Formula (1) in a molecular structure of the polyester resin and a resin containing a bisphenol structure represented by General Formula (2):

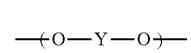

(1)

(where Y is a divalent saturated aliphatic hydrocarbon group having at least one of a tertiary carbon and a quaternary carbon)

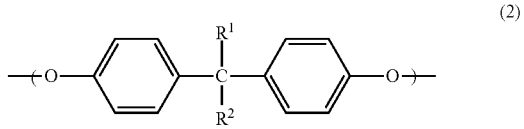

(2)

(where $R^1$ and $R^2$ each represents hydrogen or a $C_{1-20}$ organic group; $R^1$ and $R^2$ are the same as or different from each other).

In the color conversion composition according to the present invention, Y in the General Formula (1) is at least one selected from groups of the following structures:

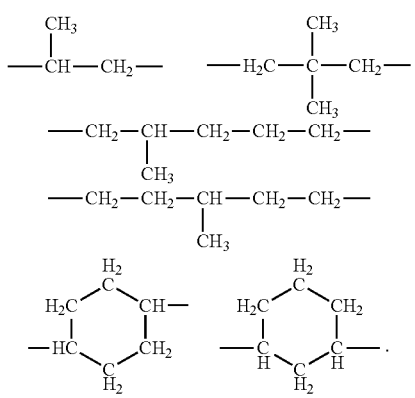

In the color conversion composition according to the present invention, Y in the General Formula (1) contains a group of the following structure:

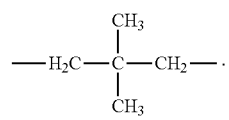

In the color conversion composition according to the present invention, when a weight ratio of the partial structure represented by the General Formula (1) to a total amount of the polyester resin contained as the Component (B) is represented as $m_1\%$ by weight, $m_1$ satisfies $10 \leq m_1 \leq 60$.

In the color conversion composition according to the present invention, the polyester resin has at least one of a partial structure represented by General Formula (3) and a partial structure represented by General Formula (4) in the molecular structure of the polyester resin:

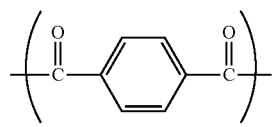

(3)

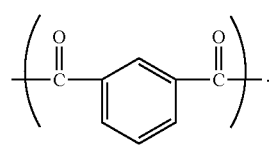

(4)

In the color conversion composition according to the present invention, the polyester resin has at least the partial structure represented by the General Formula (3) in the molecular structure of the polyester resin, and when a weight ratio of the partial structure represented by the General Formula (3) to a total amount of the polyester resin contained as the Component (B) is represented as by weight, $m_2$ satisfies $20 \leq m_2 \leq 70$.

In the color conversion composition according to the present invention, when a weight ratio of the partial structure represented by the General Formula (3) to a total amount of the polyester resin contained as the Component (B) is represented as $m_2\%$ by weight, and a weight ratio of the partial structure represented by the General Formula (4) to a total amount of the polyester resin contained as the Component (B) is represented as $m_3\%$ by weight, $m_2$ and $m_3$ satisfy $20 \leq m_2+m_3 \leq 70$.

In the color conversion composition according to the present invention, the polyester resin has at least one of a partial structure represented by General Formula (5) and a partial structure represented by General Formula (6) in a molecular structure of the polyester resin:

(5)

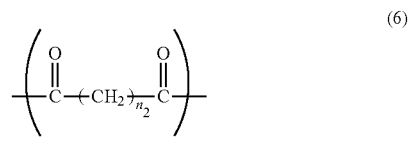

(6)

(where $n_1$ and $n_2$ are natural numbers, in which $2 \leq n_1 \leq 10$ and $2 \leq n_1 \leq 14$).

In the color conversion composition according to the present invention, $n_1=2$, and $n_2=8$.

In the color conversion composition according to the present invention, a weight average molecular weight of the polyester resin is 5,000 or more and 100,000 or less.

In the color conversion composition according to the present invention, the resin containing the bisphenol structure has at least a structure represented by General Formula (7) in a molecular structure of the resin:

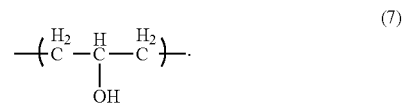

(7)

In the color conversion composition according to the present invention, a weight average molecular weight of the resin containing the bisphenol structure is 10,000 or more and 100,000 or less.

In the color conversion composition according to the present invention, the Component (A) contains a compound represented by General Formula (8):

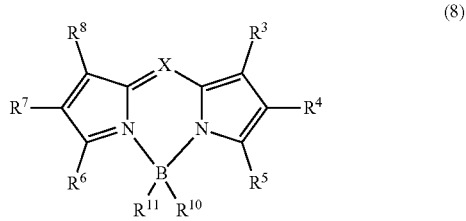

(8)

(where X is C—$R^9$ or N; $R^3$ to $R^{11}$ are the same as or different from each other and are selected from hydrogen, an alkyl group, a cycloalkyl group, a heterocyclic group, an alkenyl group, a cycloalklnyl group, an alkynyl group, a hydroxy group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a beryl group, a phosphine oxide group, and a condensed ring and an aliphatic ring formed between adjacent substituents).

In the color conversion composition according to the present invention, X in the General Formula (8) is C—R$^9$ in which R$^9$ is a group represented by General Formula (9):

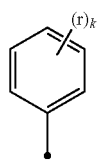

(9)

(where r is selected from the group consisting of hydrogen, an alkyl group, a cycloalkyl group, a heterocyclic group, alkenyl group, a cycloalkenyl group, an alkynyl group, a hydroxy group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a boryl group, and a phosphine oxide group; k is an integer of 1 to 3; when k is 2 or more, rs are the same as or different from each other).

In the color conversion composition according to the present invention, R$^3$, R$^5$, R$^6$, and R$^8$ in the General Formula (8) are the same as or different from each other and are substituted or unsubstituted phenyl groups.

In the color conversion composition according to the present invention, R$^3$, R$^5$, R$^6$, and R$^8$ in the General Formula (8) are the same as or different from each other and are substituted or unsubstituted alkyl groups.

In the color conversion composition according to the present invention, the Component (A) contains a light-emitting material that exhibits light emission with a peak wavelength observed in a region of 500 nm or more and 580 nm or less by using excitation light in a wavelength range of 400 nm or more and 500 nm or less.

In the color conversion composition according to the present invention, the Component (A) contains the following Light-Emitting Material (a) and Light-Emitting Material (b): Light-Emitting Material (a): a light-emitting material that exhibits light emission with a peak wavelength observed in a region of 500 nm or more and 580 nm or less by using excitation light in a wavelength range of 400 nm or more and 500 nm or less, and Light-Emitting Material (b): a light-emitting material that exhibits light emission with a peak wavelength observed in a region of 580 nm or more and 750 nm or less by being excited by at least either excitation light in a wavelength range of 400 nm or more and 500 nm or less or light emission from the Light-Emitting Material (a).

In the color conversion composition according to the present invention, a content $w_a$ of the Light-Emitting Material (a) and a content $w_b$ of the Light-Emitting Material (b) have a relation of $w_a \geq w_b$.

In the color conversion composition according to the present invention, the light-emitting material that exhibits light emission with a peak wavelength of 500 nm or more and 580 nm or less by using the excitation light in a wavelength range of 400 nm or more and 500 nm or less is the compound represented by the General Formula (8).

In the color conversion composition according to the present invention, the Light-Emitting Material (b) is the compound represented by the General Formula (8).

A color conversion sheet according to the present invention includes a layer of the color conversion composition according to any one of the above-described inventions or a layer of a cured object of the color conversion composition according to any one of the above-described inventions.

In the color conversion sheet according to the present invention further includes a barrier layer.

A light source unit according to the present invention includes: a light source; and the color conversion sheet according to any one of the above-described inventions.

In the light source unit according to the present invention, the light source is a light-emitting diode having maximum emission in a range of 400 nm or mere and 500 nm or less.

A display according to the present invention includes the light source unit according to any one of the above-described inventions.

A lighting apparatus according to the present invention includes the light source unit according to any one of the above-described inventions.

An LED chip according to the present invention includes a light-emitting face provided with the color conversion sheet according to any one of the above-described inventions.

An LED package according to the present invention includes a cured object of the color conversion composition according to any one of the above-described inventions.

An LED package according to the present invention includes the color conversion sheet according to any one of the above-described inventions.

A backlight unit according to the present, invention includes the LED package according to any one of the above-described inventions.

A display according to the present invention includes the LED package according to any one of the above-described inventions.

A lighting apparatus according to the present invention includes the LED package according to any one of the above-described inventions.

Advantageous Effects of Invention

The color conversion composition and the color conversion sheet containing the same according to the present invention achieve both high color purity and durability and thus produce an effect of making it possible to achieve both high color reproducibility and high durability. The light source unit, the display, and the lighting apparatus according to the present invention use the color conversion sheet and thus produce an effect of making it possible to achieve both high color reproducibility and high durability.

DETAILED DESCRIPTION OF CERTAIN EMBODIMENTS OF THE INVENTION

Figure 1:
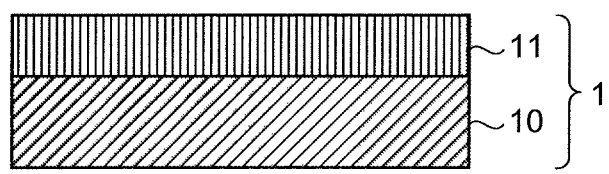
FIG. 1 is a schematic sectional view of an example of a color conversion sheet according to an embodiment of the present invention.

The following specifically describes preferred embodiments of a color conversion composition, a color conversion sheet and a light source unit including the same, a display, a lighting apparatus, a backlight unit, an LED chip, and an LED package according to the present invention; the present invention is not limited to the following embodiments and can be performed in a variously modified manner in accordance with objects and uses.

<Color Conversion Composition>

The color conversion composition according to the embodiment of the present invention converts incident light from a light-emitting body such as a light source into light with a wavelength longer than that of the incident light and contains Component (A) and Component (B). In the present invention, Component (A) is an organic light-emitting material. Component (B) is a resin containing at least one of a polyester resin having a partial structure represented by General Formula (1) in its molecular structure and a resin containing a bisphenol structure represented by General Formula (2):

(1)

In General Formula (1), Y is a divalent saturated aliphatic hydrocarbon group having at least one of a tertiary carbon and a quaternary carbon.

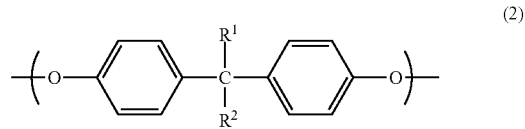

(2)

In General Formula (2), $R^1$ and $R^2$ each represent hydrogen or a $C_{1-20}$ organic group. $R^1$ and $R^2$ may be the same as or different from each other.

<Component (A): Organic Light-Emitting Material>

The color conversion composition according to the embodiment of the present invention contains the organic light-emitting material as Component (A). The light-emitting material, in the present invention refers to a material that, when being irradiated with some light, emits light with a wavelength different from that of the light.

To achieve highly efficient color conversion, the light-emitting material is preferably a material that exhibits light emission characteristics with high quantum yield. Examples of the light-emitting material generally include known light-emitting materials such as inorganic fluorescent bodies, fluorescent pigments, fluorescent dyes, and quantum dots; the organic light-emitting material is preferred in view of dispersion uniformity, a reduction in the amount of use, and a reduction in environmental loads.

Examples of the organic light-emitting material include the following ones. Preferred examples of the organic light-emitting material include compounds having a condensed aryl ring such as naphthalene, anthracene, phenanthrene, pyrene, chrysene, naphthacene, triphenylene, perylene, fluoranthene, fluorene, and indene and derivatives thereof. Preferred examples of the organic light-emitting material include compounds having a heteroaryl ring such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyridine, pyrazine, naphthyridine, quinoxaline, and pyrrolopyridine, derivatives thereof, and borane derivatives. Preferred examples of the organic light emitting material include stilbene derivatives such as 1,4-distyrylbenzene, 4,4'-bis(2-(4-diphenylaminophenyl)ethenyl)biphenyl, and 4,4'-bis(N-(stilben-4-yl)-N-phenylamino)stilbene, aromatic acetylene derivatives, tetraphenyl butadiene derivatives, aldazine derivatives, pyrromethene derivatives, and diketopyrolo[3,4-c]pyrrole derivatives. Preferred examples of the organic light-emitting material include coumarin derivatives such as coumarin 6, coumarin 7, and coumarin 153, azole derivatives such as imidazole, thiazole, thiadiazole, carbazole, oxazole oxadiazole, and triazole and metal complexes thereof, cyanine-based compounds such as indocyanine green, xanthene-based compounds such as fluorescein, eosine, and rhodamine, and thioxanthene-based compounds. Preferred examples of the organic light-emitting material include polyphenylene-based compounds, naphthalimide derivatives, phthalocyanine derivatives and metal complexes thereof, porphyrin derivatives and metal complexes thereof, oxazine-based compounds such as Nile Red and Nile Blue, helicene-based compounds, and aromatic amine derivatives such as N,N'-diphenyl-N,N'-di(3-methylphenyl)-4,4'-diphenyl-1,1'-diamine. Preferred examples of the organic light-emitting material include organic metal complex compounds of iridium (Ir), ruthenium (Ru), rhodium (Rh), palladium (Pd), platinum (Pt), osmium (Os), rhenium (Re), and the like. However, the organic light-emitting material of the present invention is not limited to these compounds.

At least one organic light-emitting material is required to be contained in the color conversion composition, and two or more ones may be contained. The organic light-emitting material may be a fluorescent light-emitting material or a phosphorescent light-emitting material; to achieve high color purity, a fluorescent light-emitting material is preferred. Among these materials, preferred are compounds having a condensed aryl ring or derivatives thereof, because of high thermal stability and photostability.

In view of solubility and the versatility of molecular structure, compounds having a coordinated bond are preferred as the organic light-emitting material. In view of being small in full width at half maximum and the capability of giving highly efficient light emission, also preferred are compounds containing boron such as boron fluoride complexes. Among them, pyrromethene derivatives are preferred in view of giving high fluorescence quantum yield and being favorable in durability. More preferred is a compound represented by General Formula (8)

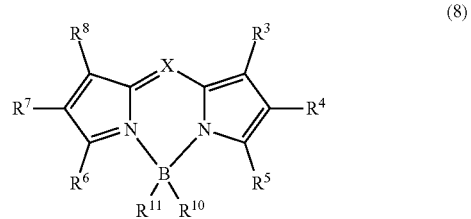

(8)

When the organic light-emitting material contains the compound represented by General Formula (8), in General Formula (8), X is C—$R^9$ or N. $R^3$ to $R^{11}$ may be the same as or different from each other and are selected from hydrogen, an alkyl group, a cycloalkyl group, a heterocyclic group, an alkenyl group, a cycloalkenyl group, an alkynyl group, a hydroxy group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a boryl group, a phosphine oxide group, and a condensed ring and an aliphatic ring formed between adjacent substituents.

In all the above groups, the hydrogen may be deuterium. This holds true for compounds or partial structures thereof described below. In the following description, a substituted or unsubstituted $C_{6-40}$ aryl group, for example, is an aryl group all the carbon number of which is 6 to 40 including the carbon number included in a substituent by which the aryl group is substituted. This holds true for other substituents defining the carbon number.

In all the above groups, a substituent when they are substituted is preferably an alkyl group, a cycloalkyl group, a heterocyclic group, an alkenyl group, a cycloalkenyl group, an alkynyl group, a hydroxy group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a boryl group, a phosphine oxide group, or further, a specific substituent described as preferred in the descriptions of the respective substituents. These substituents may be further substituted by the substituents described above.

"Unsubstituted" in "substituted or unsubstituted" means that a hydrogen atom or deuterium atom has substituted. The above holds true for cases described as "substituted or unsubstituted" in the compounds or partial structures thereof described below.

In all the above groups, the alkyl group refers to a saturated aliphatic hydrocarbon group such as a methyl group, an ethyl group, a n-propyl group, an isopropyl group, a n-butyl group, a sec-butyl group, or a tert-butyl group, which optionally has a substituent. An additional substituent when it is substituted is not limited to a particular substituent, and examples thereof include an alkyl group, halogen, an aryl group, and a heteroaryl group, which is common to the following description. The carbon number of the alkyl group, which is not limited to a particular number, is in the range of preferably 1 or more and 20 or less and more preferably 1 or more and 8 or less in view of availability and cost.

The cycloalkyl group refers to a saturated alicyclic hydrocarbon group such as a cyclopropyl group, a cyclohexyl group, a norbornyl group, or an adamantyl group, which optionally has a substituent. The carbon number of the alkyl group part, which is not limited to a particular number, is preferably in the range of 3 or more and 20 or less.

The heterocyclic group refers to an aliphatic ring having an atom other than carbon within its ring such as a pyran ring, a piperidine ring, or a cyclic amide, which optionally has a substituent. The carbon number of the heterocyclic group, which is not limited to a particular number, is preferably in the range of 2 or more and 20 or less.

The alkenyl group refers to an unsaturated aliphatic hydrocarbon group containing a double bond such as a vinyl group, an allyl group, or a butadienyl group, which optionally has a substituent. The carbon number of the alkenyl group, which is not limited to a particular number, is preferably in the range of 2 or more and 20 or less.

The cycloalkenyl group refers to an unsaturated alicyclic hydrocarbon group containing a double bond such as a cyclopentenyl group, a cyclopentadienyl group, or a cyclohexenyl group, which optionally has a substituent.

The alkynyl group refers to an unsaturated aliphatic hydrocarbon group containing a triple bond such as an ethynyl group, which optionally has a substituent. The carbon number of the alkynyl group, which is not limited to a particular number, is preferably in the range of 2 or more and 20 or less.

The alkoxy group refers to a functional group to which an aliphatic hydrocarbon group bonds through an ether bond such as a methoxy group, an ethoxy group, or a propoxy group, and this aliphatic hydrocarbon group optionally has a substituent. The carbon number of the alkoxy group, which is not limited to a particular number, is preferably in the range of 1 or more and 20 or less.

The alkylthio group is a group in which the oxygen atom of the ether bond of the alkoxy group is substituted by a sulfur atom. The hydrocarbon group of the alkylthio group optionally has a substituent. The carbon number of the alkylthio group, which is not limited to a particular number, is preferably in the range of 1 or more and 20 or less.

The aryl ether group refers to a function group to which an aromatic hydrocarbon group bonds through an ether bond such as a phenoxy group, and the aromatic hydrocarbon group optionally has a substituent. The carbon number of the aryl ether group, which is not limited to a particular number, is preferably in the range of 6 or more and 40 or less.

The aryl thioether group is a group in which the oxygen atom of the ether bond of the aryl ether group is substituted by a sulfur atom. The aromatic hydrocarbon group of the aryl thioether group optionally has a substituent. The carbon number of the aryl thioether group, which is not limited to a particular number, is preferably in the range of 6 or more and 40 or less.

The aryl group refers to an aromatic hydrocarbon group such as a phenyl group, a biphenyl group, a terphenyl group, a naphthyl group, a fluorenyl group, a benzofluorenyl group, a dibenzofluorenyl group, a phenanthryl group, an anthracenyl group, a benzophenanthryl group, a benzoanthracenyl group, a crycenyl group, a pyrenyl group, a fluoranthenyl group, a triphenylenyl group, a benzofluoranthenyl group, a dibenzoanthracenyl group, a perylenyl group, or a helicenyl group. Among them, preferred are a phenyl group, a biphenyl group, a terphenyl group, a naphthyl group, a fluorenyl group, a phenanthryl group, an anthracenyl group, a pyrenyl group, a fluoranthenyl group, and a triphenylenyl group. The aryl group optionally has a substituent. The carbon number of the aryl group, which is not limited to a particular number, is in the range of preferably 6 or more and 40 or less and more preferably 6 or more and 30 or less.

When $R^3$ to $R^{11}$ are each a substituted or unsubstituted aryl group, the aryl group is preferably a phenyl group, a biphenyl group, a terphenyl group, a naphthyl group, a fluorenyl group, a phenanthryl group, or an anthracenyl group, more preferably a phenyl group, a biphenyl group, a terphenyl group, or a naphthyl group, further preferably a phenyl group, a biphenyl group, or a terphenyl group, and particularly preferably a phenyl group.

When each of the substituents is further substituted by an aryl group, the aryl group is preferably a phenyl group, a biphenyl group, a terphenyl group, a naphthyl group, a fluorenyl group, a phenanthryl group, or an anthracenyl group, more preferably a phenyl group, a biphenyl group, a terphenyl group, or a naphthyl group, and particularly preferably a phenyl group.

The heteroaryl group refers to a cyclic aromatic group having one or more atoms other than carbon within its ring such as a pyridyl group, a furanyl group, a thiophenyl group, a quinolinyl group, an isoquinolinyl group, a pyrazinyl group, a pyrimidyl group, a pyridazinyl group, a triazinyl group, a naphthyridinyl group, a cinnolinyl group, a phthalazinyl group, a quinoxalinyl group, a quinazolinyl group, a benzofuranyl group, a benzothiophenyl group, an indolyl group, a dibenzofuranyl group, a dibenzothiophenyl group, a carbazolyl group, a benzocarbazolyl group, a carbolinyl group, an indolocarbazolyl group, a benzofurocarbazolyl group, a benzothienocarbazolyl group, a dihydroindenocarbazolyl group, a benzoquinolinyl group, an acridinyl group, a dibenzoacridinyl group, a benzimidazolyl group, an imidazopyridyl group, a benzoxazolyl group, a benzothiazolyl group, or a phenanthrolinyl group. The naphthyridinyl group refers to any of a 1,5-naphthyridinyl group, a 1,6-naphthyridinyl group, a 1,7-naphthyridinyl group a 1,8-naphthyridinyl group, a 2,6-naphthyridinyl group, or a 2,7-naphthyridinyl group. The heteroaryl group optionally has a substituent. The carbon number of the heteroaryl group which is not limited to a particular number, is in the range of preferably 2 or more and 40 or less and more preferably 2 or more and 30 or less.

When $R^3$ to $R^{11}$ are each a substituted or unsubstituted heteroaryl group, the heteroaryl group is preferably a pyridyl group, a furanyl group, a thiophenyl group, a quinolinyl group, a pyrimidyl group, a triazinyl group, a benzofuranyl group, a benzothiophenyl group, an indolyl group, a dibenzofuranyl group, a dibenzothiophenyl group, a carbazolyl group, a benzimidazolyl group, an imidazopyridyl group, a benzoxazolyl group, a benzothiazolyl group, or a phenanthrolinyl group, more preferably a pyridyl group, a furanyl group, a thiophenyl group, or a quinolinyl group, and particularly preferably a pyridyl group.

When each of the substituents is further substituted by a heteroaryl group, the heteroaryl group is preferably a pyridyl group, a furanyl group, a thiophenyl group, a quinolinyl group, a pyrimidyl group, a triazinyl group, a benzofuranyl group, a benzothiophenyl group, an indolyl group, a dibenzofuranyl group, a dibenzothiophenyl group, a carbazolyl group, a benzimidazolyl group, an imidazopyridyl group, a benzoxazolyl group, a benzothiazolyl group, or a phenanthrolinyl group, more preferably a pyridyl group, a furanyl group, a thiophenyl group, or a quinolinyl group, and particularly preferably a pyridyl group.

The halogen refers to an atom selected from fluorine, chlorine, bromine, and iodine. The carbonyl group, the carboxy group, the oxycarbonyl group, and the carbamoyl group each optionally have a substituent. Examples of the substituent include an alkyl group, a cycloalkyl group, an aryl group, and a heteroaryl group, and these substituents may be further substituted.

The amino group is a substituted or unsubstituted amino group. The amino group optionally has a substituent; examples of the substituent when it is substituted include an aryl group, a heteroaryl group, a linear alkyl group, and a branched alkyl group. The aryl group and the heteroaryl group are preferably a phenyl group, a naphthyl group, a pyridyl group, or a quinolinyl group. These substituents may be further substituted. The carbon number, which is not limited to a particular number, is in the range of preferably 2 or more and 50 or less, more preferably 6 or more and 40 or less, and particularly preferably 6 or more and 30 or less.

The silyl group refers to an alkyl silyl group such as a trimethylsilyl group, a triethylsilyl group, a tert-butyl dimethyl silyl group, a propyl dimethyl silyl group, or a vinyl dimethyl silyl group and an aryl silyl group such as a phenyl dimethyl silyl group, a tert-butyl diphenyl silyl group, a triphenyl silyl group, or a trinaphthyl silyl group. The substituent on the silicon may be further substituted. The carbon number of the silyl group, which is not limited to a particular number, is preferably in the range of 1 or more and 30 or less.

The siloxanyl group refers to a silicide through an ether bond such as trimethylsiloxanyl group. The substituent on the silicon may be further substituted. The boryl group is a substituted or unsubstituted boryl group. The boryl group optionally has a substituent; examples of the substituent when it is substituted include an aryl group, a heteroaryl group, a linear alkyl group, a branched alkyl group, an aryl ether group, an alkoxy group, and a hydroxy group. Among them, preferred are an aryl group and an aryl ether group. The phosphine oxide group is a group represented by —P(=O)$R^{12}R^{13}$. $R^{12}R^{13}$ are each selected from a group similar to that for $R^3$ to $R^{11}$.

The condensed ring formed between adjacent substituents refers to mutual bonding between any two adjacent substituents ($R^3$ and $R^4$ in General Formula (8), for example) forming a conjugated or non-conjugated cyclic skeleton. The element of the condensed ring may contain an element selected from nitrogen, oxygen, sulfur, phosphorous, and silicon apart from carbon. The condensed ring may further condense with another ring.

The compound represented by General Formula (8) exhibits high fluorescence quantum yield and is small in the peak full width at half maximum of an emission spectrum, thus enabling both efficient color conversion and high color purity to be achieved. Furthermore, the compound represented by General Formula (8), by introducing an appropriate substituent to an appropriate position, enables various characteristics and properties such as emission efficiency, color purity, thermal stability, photostability, and dispersibility to be adjusted. A case in which at least one of $R^3$, $R^5$, $R^6$, and $R^8$ is a substituted or unsubstituted alkyl group, a substituted or unsubstituted aryl group, or a substituted or unsubstituted heteroaryl group exhibits better thermal stability and photostability compared with a case in which all $R^3$, $R^5$, $R^6$, and $R^8$ are hydrogens, for example.

When at least one of $R^3$, $R^5$, $R^6$, and $R^8$ is a substituted or unsubstituted alkyl group, the alkyl group is preferably a $C_{1-6}$ alkyl group such as a methyl group, an ethyl group, a n-propyl group, an isopropyl group, a n-butyl group, a sec-butyl group, a tert-butyl group, a pentyl group, or a hexyl group. Furthermore, this alkyl group is preferably a methyl group, an ethyl group, a n-propyl group, an isopropyl group, a n-butyl group, a sec-butyl group, or a tert-butyl group in view of being excellent in thermal stability. In view of preventing concentration quenching to improve fluorescence quantum yield, this alkyl group is more preferably a tert-butyl group, which is sterically bulky. In view of the easiness of synthesis and raw material availability, this alkyl group is also preferably a methyl group.

When at least one of $R^3$, $R^5$, $R^6$, and $R^8$ is a substituted or unsubstituted aryl group, the aryl group is preferably a phenyl group, a biphenyl group, a terphenyl group, or a naphthyl group, further preferably a phenyl group or a biphenyl group, and particularly preferably a phenyl group.

When at least one of $R^3$, $R^5$, $R^6$, and $R^8$ is a substituted or unsubstituted heteroaryl group, the heteroaryl group is preferably a pyridyl group, a quinolinyl group, or a thiophenyl group, further preferably a pyridyl group or a quinolinyl group, and particularly preferably a pyridyl group.

When all $R^3$, $R^5$, $R^6$, and $R^8$ may be the same as or different from each other and are substituted or unsubstituted alkyl groups, solubility to a binder resin or a solvent is favorable, which is preferred. In this case, the alkyl group is preferably a methyl group in view of the easiness of synthesis and raw material availability.

When all $R^3$, $R^5$, $R^6$, and $R^8$ which may be the same as or different from each other, are substituted or unsubstituted aryl groups or substituted or unsubstituted heteroaryl groups, better thermal stability and photostability are exhibited, which is preferred. In this case, all $R^3$, $R^5$, $R^6$, and $R^8$ which may be the same as or different from each other, are more preferably substituted or unsubstituted aryl groups.

Although some substituents improve a plurality of properties, substituents that exhibit sufficient performance in all are limited. In particular, it is difficult to achieve both high emission efficiency and high color purity. Given these circumstances, a plurality of kinds of substituents are introduced to the compound represented by General Formula (8), whereby a compound having a balance among emission characteristics, high color purity, and the like can be obtained.

In particular, when all $R^3$, $R^5$, $R^6$, and $R^8$, which may be the same as or different from each other, are substituted or unsubstituted aryl groups, a plurality of kinds of substituents are preferably introduced, such as $R^3 \neq R^6$, $R^5 \neq R^8$, $R^3 \neq R^5$, or $R^6 \neq R^8$. In this example, "$\neq$" means that they are groups having different structures. $R^3 \neq R^6$ means that $R^3$ and $R^6$ are groups having different structures, for example. A plurality of kinds of substituents are introduced as described above, whereby an aryl group that has an influence on color purity and an aryl group that has an influence on emission efficiency can be simultaneously introduced, and fine adjustment can be made.

Among them, $R^3 \neq R^5$ or $R^6 \neq R^8$ is preferred in view of improving emission efficiency and color purity with a good balance. In this case, to the compound represented by General Formula (8), one or more aryl groups having an influence on color purity can be introduced to both pyrrole rings each, whereas an aryl group having an influence on emission efficiency can be introduced to any other position, and both of these properties can be improved to the maximum. In addition, when $R^3 \neq R^5$ or $R^6 \neq R^8$, in view of improving both heat resistance and color purity, more preferred are $R^3 = R^6$ and $R^5 = R^3$.

The aryl group that has an influence mainly on color purity is preferably an aryl group substituted by an electron donating group. Examples of this electron donating group include an alkyl group and an alkoxy group. In particular, a $C_{1-8}$ alkyl group or a $C_{1-8}$ alkoxy group is preferred, and more preferred are a methyl group, an ethyl group, a tert-butyl group, and a methoxy group. In view of dispersibility, a tert-butyl group and a methoxy group are particularly preferred; when these substituents are introduced as the electron donating group, quenching caused by the flocculation of molecules can be prevented in the compound represented by General Formula (8). Although the substitution position of the substituent is not limited to a particular position, the substituent is preferably bonded to the meta position or the para position relative to the position bonding to the pyrromethene skeleton, because the twist, of bonding is required to be inhibited in order to increase the photostability of the compound represented by General Formula (8). The aryl group that has an influence mainly on emission efficiency is preferably an aryl group having a bulky substituent such as a tert-butyl group, an adamantyl group, or a methoxy group.

When $R^3$, $R^5$, $R^6$, and $R^8$ which may be the same as or different from each other, are substituted or unsubstituted aryl groups, $R^3$, $R^5$, $R^6$, and $R^8$, which may be the same as or different from each other, are preferably substituted or unsubstituted phenyl groups. In this case, $R^3$, $R^5$, $R^6$, and $R^8$ are each more preferably selected from the following Ar-1 to Ar-6. In this case, examples of a preferred combination of $R^3$, $R^5$, $R^6$, and $R^8$ include, but are not limited to, combinations listed in Table 1-1 to Table 1-11.

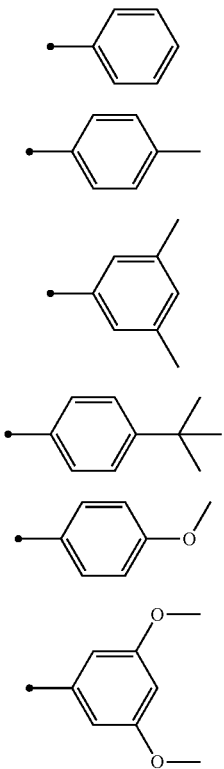

Ar-1

Ar-2

Ar-3

Ar-4

Ar-5

Ar-6

TABLE 1-1

| R3 | R5 | R6 | R8 |
|---|---|---|---|
| Ar-1 | Ar-1 | Ar-1 | Ar-1 |
| Ar-1 | Ar-1 | Ar-1 | Ar-2 |
| Ar-1 | Ar-1 | Ar-1 | Ar-3 |
| Ar-1 | Ar-1 | Ar-1 | Ar-4 |
| Ar-1 | Ar-1 | Ar-1 | Ar-5 |
| Ar-1 | Ar-1 | Ar-1 | Ar-6 |
| Ar-1 | Ar-1 | Ar-2 | Ar-1 |
| Ar-1 | Ar-1 | Ar-2 | Ar-2 |
| Ar-1 | Ar-1 | Ar-2 | Ar-3 |
| Ar-1 | Ar-1 | Ar-2 | Ar-4 |
| Ar-1 | Ar-1 | Ar-2 | Ar-5 |
| Ar-1 | Ar-1 | Ar-2 | Ar-6 |
| Ar-1 | Ar-1 | Ar-3 | Ar-1 |
| Ar-1 | Ar-1 | Ar-3 | Ar-2 |
| Ar-1 | Ar-1 | Ar-3 | Ar-3 |
| Ar-1 | Ar-1 | Ar-3 | Ar-4 |
| Ar-1 | Ar-1 | Ar-3 | Ar-5 |
| Ar-1 | Ar-1 | Ar-3 | Ar-6 |
| Ar-1 | Ar-1 | Ar-4 | Ar-1 |
| Ar-1 | Ar-1 | Ar-4 | Ar-2 |
| Ar-1 | Ar-1 | Ar-4 | Ar-3 |
| Ar-1 | Ar-1 | Ar-4 | Ar-4 |
| Ar-1 | Ar-1 | Ar-4 | Ar-5 |
| Ar-1 | Ar-1 | Ar-4 | Ar-6 |
| Ar-1 | Ar-1 | Ar-5 | Ar-1 |
| Ar-1 | Ar-1 | Ar-5 | Ar-2 |
| Ar-1 | Ar-1 | Ar-5 | Ar-3 |
| Ar-1 | Ar-1 | Ar-5 | Ar-4 |
| Ar-1 | Ar-1 | Ar-5 | Ar-5 |

TABLE 1-1-continued

| R3 | R5 | R6 | R8 |
|---|---|---|---|
| Ar-1 | Ar-1 | Ar-5 | Ar-6 |
| Ar-1 | Ar-1 | Ar-6 | Ar-1 |
| Ar-1 | Ar-1 | Ar-6 | Ar-2 |
| Ar-1 | Ar-1 | Ar-6 | Ar-3 |
| Ar-1 | Ar-1 | Ar-6 | Ar-4 |
| Ar-1 | Ar-1 | Ar-6 | Ar-5 |
| Ar-1 | Ar-1 | Ar-6 | Ar-6 |
| Ar-1 | Ar-2 | Ar-1 | Ar-2 |
| Ar-1 | Ar-2 | Ar-1 | Ar-3 |
| Ar-1 | Ar-2 | Ar-1 | Ar-4 |
| Ar-1 | Ar-2 | Ar-1 | Ar-5 |
| Ar-1 | Ar-2 | Ar-1 | Ar-6 |
| Ar-1 | Ar-2 | Ar-2 | Ar-1 |
| Ar-1 | Ar-2 | Ar-2 | Ar-2 |
| Ar-1 | Ar-2 | Ar-2 | Ar-3 |
| Ar-1 | Ar-2 | Ar-2 | Ar-4 |
| Ar-1 | Ar-2 | Ar-2 | Ar-5 |
| Ar-1 | Ar-2 | Ar-2 | Ar-6 |
| Ar-1 | Ar-2 | Ar-3 | Ar-1 |
| Ar-1 | Ar-2 | Ar-3 | Ar-2 |
| Ar-1 | Ar-2 | Ar-3 | Ar-3 |
| Ar-1 | Ar-2 | Ar-3 | Ar-4 |
| Ar-1 | Ar-2 | Ar-3 | Ar-5 |
| Ar-1 | Ar-2 | Ar-3 | Ar-6 |
| Ar-1 | Ar-2 | Ar-4 | Ar-1 |
| Ar-1 | Ar-2 | Ar-4 | Ar-2 |
| Ar-1 | Ar-2 | Ar-4 | Ar-3 |
| Ar-1 | Ar-2 | Ar-4 | Ar-4 |
| Ar-1 | Ar-2 | Ar-4 | Ar-5 |
| Ar-1 | Ar-2 | Ar-4 | Ar-6 |

TABLE 1-2

| R3 | R5 | R6 | R8 |
|---|---|---|---|
| Ar-1 | Ar-2 | Ar-5 | Ar-1 |
| Ar-1 | Ar-2 | Ar-5 | Ar-2 |
| Ar-1 | Ar-2 | Ar-5 | Ar-3 |
| Ar-1 | Ar-2 | Ar-5 | Ar-4 |
| Ar-1 | Ar-2 | Ar-5 | Ar-5 |
| Ar-1 | Ar-2 | Ar-5 | Ar-6 |
| Ar-1 | Ar-2 | Ar-6 | Ar-1 |
| Ar-1 | Ar-2 | Ar-6 | Ar-2 |
| Ar-1 | Ar-2 | Ar-6 | Ar-3 |
| Ar-1 | Ar-2 | Ar-6 | Ar-4 |
| Ar-1 | Ar-2 | Ar-6 | Ar-5 |
| Ar-1 | Ar-2 | Ar-6 | Ar-6 |
| Ar-1 | Ar-3 | Ar-1 | Ar-2 |
| Ar-1 | Ar-3 | Ar-1 | Ar-3 |
| Ar-1 | Ar-3 | Ar-1 | Ar-4 |
| Ar-1 | Ar-3 | Ar-1 | Ar-5 |
| Ar-1 | Ar-3 | Ar-1 | Ar-6 |
| Ar-1 | Ar-3 | Ar-2 | Ar-2 |
| Ar-1 | Ar-3 | Ar-2 | Ar-3 |
| Ar-1 | Ar-3 | Ar-2 | Ar-4 |
| Ar-1 | Ar-3 | Ar-2 | Ar-5 |
| Ar-1 | Ar-3 | Ar-2 | Ar-6 |
| Ar-1 | Ar-3 | Ar-3 | Ar-1 |
| Ar-1 | Ar-3 | Ar-3 | Ar-2 |
| Ar-1 | Ar-3 | Ar-3 | Ar-3 |
| Ar-1 | Ar-3 | Ar-3 | Ar-4 |
| Ar-1 | Ar-3 | Ar-3 | Ar-5 |
| Ar-1 | Ar-3 | Ar-3 | Ar-6 |
| Ar-1 | Ar-3 | Ar-4 | Ar-1 |
| Ar-1 | Ar-3 | Ar-4 | Ar-2 |
| Ar-1 | Ar-3 | Ar-4 | Ar-3 |
| Ar-1 | Ar-3 | Ar-4 | Ar-4 |
| Ar-1 | Ar-3 | Ar-4 | Ar-5 |
| Ar-1 | Ar-3 | Ar-4 | Ar-6 |
| Ar-1 | Ar-3 | Ar-5 | Ar-1 |
| Ar-1 | Ar-3 | Ar-5 | Ar-2 |
| Ar-1 | Ar-3 | Ar-5 | Ar-3 |
| Ar-1 | Ar-3 | Ar-5 | Ar-4 |
| Ar-1 | Ar-3 | Ar-5 | Ar-5 |
| Ar-1 | Ar-3 | Ar-5 | Ar-6 |

TABLE 1-2-continued

| R3 | R5 | R6 | R8 |
|---|---|---|---|
| Ar-1 | Ar-3 | Ar-6 | Ar-1 |
| Ar-1 | Ar-3 | Ar-6 | Ar-2 |
| Ar-1 | Ar-3 | Ar-6 | Ar-3 |
| Ar-1 | Ar-3 | Ar-6 | Ar-4 |
| Ar-1 | Ar-3 | Ar-6 | Ar-5 |
| Ar-1 | Ar-3 | Ar-6 | Ar-6 |
| Ar-1 | Ar-4 | Ar-1 | Ar-2 |
| Ar-1 | Ar-4 | Ar-1 | Ar-3 |
| Ar-1 | Ar-4 | Ar-1 | Ar-4 |
| Ar-1 | Ar-4 | Ar-1 | Ar-5 |
| Ar-1 | Ar-4 | Ar-1 | Ar-6 |
| Ar-1 | Ar-4 | Ar-2 | Ar-2 |
| Ar-1 | Ar-4 | Ar-2 | Ar-3 |
| Ar-1 | Ar-4 | Ar-2 | Ar-4 |
| Ar-1 | Ar-4 | Ar-2 | Ar-5 |
| Ar-1 | Ar-4 | Ar-2 | Ar-6 |
| Ar-1 | Ar-4 | Ar-3 | Ar-2 |
| Ar-1 | Ar-4 | Ar-3 | Ar-3 |
| Ar-1 | Ar-4 | Ar-3 | Ar-4 |
| Ar-1 | Ar-4 | Ar-3 | Ar-5 |
| Ar-1 | Ar-4 | Ar-3 | Ar-6 |

TABLE 1-3

| R3 | R5 | R6 | R8 |
|---|---|---|---|
| Ar-1 | Ar-4 | Ar-4 | Ar-1 |
| Ar-1 | Ar-4 | Ar-4 | Ar-2 |
| Ar-1 | Ar-4 | Ar-4 | Ar-3 |
| Ar-1 | Ar-4 | Ar-4 | Ar-4 |
| Ar-1 | Ar-4 | Ar-4 | Ar-5 |
| Ar-1 | Ar-4 | Ar-4 | Ar-6 |
| Ar-1 | Ar-4 | Ar-5 | Ar-1 |
| Ar-1 | Ar-4 | Ar-5 | Ar-2 |
| Ar-1 | Ar-4 | Ar-5 | Ar-3 |
| Ar-1 | Ar-4 | Ar-5 | Ar-4 |
| Ar-1 | Ar-4 | Ar-5 | Ar-5 |
| Ar-1 | Ar-4 | Ar-5 | Ar-6 |
| Ar-1 | Ar-4 | Ar-6 | Ar-1 |
| Ar-1 | Ar-4 | Ar-6 | Ar-2 |
| Ar-1 | Ar-4 | Ar-6 | Ar-3 |
| Ar-1 | Ar-4 | Ar-6 | Ar-4 |
| Ar-1 | Ar-4 | Ar-6 | Ar-5 |
| Ar-1 | Ar-4 | Ar-6 | Ar-6 |
| Ar-1 | Ar-5 | Ar-1 | Ar-2 |
| Ar-1 | Ar-5 | Ar-1 | Ar-3 |
| Ar-1 | Ar-5 | Ar-1 | Ar-4 |
| Ar-1 | Ar-5 | Ar-1 | Ar-5 |
| Ar-1 | Ar-5 | Ar-1 | Ar-6 |
| Ar-1 | Ar-5 | Ar-2 | Ar-2 |
| Ar-1 | Ar-5 | Ar-2 | Ar-3 |
| Ar-1 | Ar-5 | Ar-2 | Ar-4 |
| Ar-1 | Ar-5 | Ar-2 | Ar-5 |
| Ar-1 | Ar-5 | Ar-2 | Ar-6 |
| Ar-1 | Ar-5 | Ar-3 | Ar-2 |
| Ar-1 | Ar-5 | Ar-3 | Ar-3 |
| Ar-1 | Ar-5 | Ar-3 | Ar-4 |
| Ar-1 | Ar-5 | Ar-3 | Ar-5 |
| Ar-1 | Ar-5 | Ar-3 | Ar-6 |
| Ar-1 | Ar-5 | Ar-4 | Ar-2 |
| Ar-1 | Ar-5 | Ar-4 | Ar-3 |
| Ar-1 | Ar-5 | Ar-4 | Ar-4 |
| Ar-1 | Ar-5 | Ar-4 | Ar-5 |
| Ar-1 | Ar-5 | Ar-4 | Ar-6 |
| Ar-1 | Ar-5 | Ar-5 | Ar-1 |
| Ar-1 | Ar-5 | Ar-5 | Ar-2 |
| Ar-1 | Ar-5 | Ar-5 | Ar-3 |
| Ar-1 | Ar-5 | Ar-5 | Ar-4 |
| Ar-1 | Ar-5 | Ar-5 | Ar-5 |
| Ar-1 | Ar-5 | Ar-5 | Ar-6 |
| Ar-1 | Ar-5 | Ar-6 | Ar-1 |
| Ar-1 | Ar-5 | Ar-6 | Ar-2 |
| Ar-1 | Ar-5 | Ar-6 | Ar-3 |
| Ar-1 | Ar-5 | Ar-6 | Ar-4 |
| Ar-1 | Ar-5 | Ar-6 | Ar-5 |

TABLE 1-3-continued

| R3 | R5 | R6 | R8 |
|---|---|---|---|
| Ar-1 | Ar-5 | Ar-6 | Ar-6 |
| Ar-1 | Ar-6 | Ar-1 | Ar-2 |
| Ar-1 | Ar-6 | Ar-1 | Ar-3 |
| Ar-1 | Ar-6 | Ar-1 | Ar-4 |
| Ar-1 | Ar-6 | Ar-1 | Ar-5 |
| Ar-1 | Ar-6 | Ar-1 | Ar-6 |
| Ar-1 | Ar-6 | Ar-2 | Ar-2 |
| Ar-1 | Ar-6 | Ar-2 | Ar-3 |
| Ar-1 | Ar-6 | Ar-2 | Ar-4 |
| Ar-1 | Ar-6 | Ar-2 | Ar-5 |
| Ar-1 | Ar-6 | Ar-2 | Ar-6 |

TABLE 1-4

| R3 | R5 | R6 | R8 |
|---|---|---|---|
| Ar-1 | Ar-6 | Ar-3 | Ar-2 |
| Ar-1 | Ar-6 | Ar-3 | Ar-3 |
| Ar-1 | Ar-6 | Ar-3 | Ar-4 |
| Ar-1 | Ar-6 | Ar-3 | Ar-5 |
| Ar-1 | Ar-6 | Ar-3 | Ar-6 |
| Ar-1 | Ar-6 | Ar-4 | Ar-2 |
| Ar-1 | Ar-6 | Ar-4 | Ar-3 |
| Ar-1 | Ar-6 | Ar-4 | Ar-4 |
| Ar-1 | Ar-6 | Ar-4 | Ar-5 |
| Ar-1 | Ar-6 | Ar-4 | Ar-6 |
| Ar-1 | Ar-6 | Ar-5 | Ar-2 |
| Ar-1 | Ar-6 | Ar-5 | Ar-3 |
| Ar-1 | Ar-6 | Ar-5 | Ar-4 |
| Ar-1 | Ar-6 | Ar-5 | Ar-5 |
| Ar-1 | Ar-6 | Ar-5 | Ar-6 |
| Ar-1 | Ar-6 | Ar-6 | Ar-1 |
| Ar-1 | Ar-6 | Ar-6 | Ar-2 |
| Ar-1 | Ar-6 | Ar-6 | Ar-3 |
| Ar-1 | Ar-6 | Ar-6 | Ar-4 |
| Ar-1 | Ar-6 | Ar-6 | Ar-5 |
| Ar-1 | Ar-6 | Ar-6 | Ar-6 |
| Ar-2 | Ar-1 | Ar-1 | Ar-2 |
| Ar-2 | Ar-1 | Ar-1 | Ar-3 |
| Ar-2 | Ar-1 | Ar-1 | Ar-4 |
| Ar-2 | Ar-1 | Ar-1 | Ar-5 |
| Ar-2 | Ar-1 | Ar-1 | Ar-6 |
| Ar-2 | Ar-1 | Ar-2 | Ar-2 |
| Ar-2 | Ar-1 | Ar-2 | Ar-3 |
| Ar-2 | Ar-1 | Ar-2 | Ar-4 |
| Ar-2 | Ar-1 | Ar-2 | Ar-5 |
| Ar-2 | Ar-1 | Ar-2 | Ar-6 |
| Ar-2 | Ar-1 | Ar-3 | Ar-2 |
| Ar-2 | Ar-1 | Ar-3 | Ar-3 |
| Ar-2 | Ar-1 | Ar-3 | Ar-4 |
| Ar-2 | Ar-1 | Ar-3 | Ar-5 |
| Ar-2 | Ar-1 | Ar-3 | Ar-6 |
| Ar-2 | Ar-1 | Ar-4 | Ar-2 |
| Ar-2 | Ar-1 | Ar-4 | Ar-3 |
| Ar-2 | Ar-1 | Ar-4 | Ar-4 |
| Ar-2 | Ar-1 | Ar-4 | Ar-5 |
| Ar-2 | Ar-1 | Ar-4 | Ar-6 |
| Ar-2 | Ar-1 | Ar-5 | Ar-2 |
| Ar-2 | Ar-1 | Ar-5 | Ar-3 |
| Ar-2 | Ar-1 | Ar-5 | Ar-4 |
| Ar-2 | Ar-1 | Ar-5 | Ar-5 |
| Ar-2 | Ar-1 | Ar-5 | Ar-6 |
| Ar-2 | Ar-1 | Ar-6 | Ar-2 |
| Ar-2 | Ar-1 | Ar-6 | Ar-3 |
| Ar-2 | Ar-1 | Ar-6 | Ar-4 |
| Ar-2 | Ar-1 | Ar-6 | Ar-5 |
| Ar-2 | Ar-1 | Ar-6 | Ar-6 |
| Ar-2 | Ar-2 | Ar-1 | Ar-3 |
| Ar-2 | Ar-2 | Ar-1 | Ar-4 |
| Ar-2 | Ar-2 | Ar-1 | Ar-5 |
| Ar-2 | Ar-2 | Ar-1 | Ar-6 |
| Ar-2 | Ar-2 | Ar-2 | Ar-3 |
| Ar-2 | Ar-2 | Ar-2 | Ar-4 |
| Ar-2 | Ar-2 | Ar-2 | Ar-5 |

TABLE 1-4-continued

| R3 | R5 | R6 | R8 |
|---|---|---|---|
| Ar-2 | Ar-2 | Ar-2 | Ar-6 |

TABLE 1-5

| R3 | R5 | R6 | R8 |
|---|---|---|---|
| Ar-2 | Ar-2 | Ar-3 | Ar-2 |
| Ar-2 | Ar-2 | Ar-3 | Ar-3 |
| Ar-2 | Ar-2 | Ar-3 | Ar-4 |
| Ar-2 | Ar-2 | Ar-3 | Ar-5 |
| Ar-2 | Ar-2 | Ar-3 | Ar-6 |
| Ar-2 | Ar-2 | Ar-4 | Ar-2 |
| Ar-2 | Ar-2 | Ar-4 | Ar-3 |
| Ar-2 | Ar-2 | Ar-4 | Ar-4 |
| Ar-2 | Ar-2 | Ar-4 | Ar-5 |
| Ar-2 | Ar-2 | Ar-4 | Ar-6 |
| Ar-2 | Ar-2 | Ar-5 | Ar-2 |
| Ar-2 | Ar-2 | Ar-5 | Ar-3 |
| Ar-2 | Ar-2 | Ar-5 | Ar-4 |
| Ar-2 | Ar-2 | Ar-5 | Ar-5 |
| Ar-2 | Ar-2 | Ar-5 | Ar-6 |
| Ar-2 | Ar-2 | Ar-6 | Ar-2 |
| Ar-2 | Ar-2 | Ar-6 | Ar-3 |
| Ar-2 | Ar-2 | Ar-6 | Ar-4 |
| Ar-2 | Ar-2 | Ar-6 | Ar-5 |
| Ar-2 | Ar-2 | Ar-6 | Ar-6 |
| Ar-2 | Ar-3 | Ar-1 | Ar-3 |
| Ar-2 | Ar-3 | Ar-1 | Ar-4 |
| Ar-2 | Ar-3 | Ar-1 | Ar-5 |
| Ar-2 | Ar-3 | Ar-1 | Ar-6 |
| Ar-2 | Ar-3 | Ar-2 | Ar-3 |
| Ar-2 | Ar-3 | Ar-2 | Ar-4 |
| Ar-2 | Ar-3 | Ar-2 | Ar-5 |
| Ar-2 | Ar-3 | Ar-2 | Ar-6 |
| Ar-2 | Ar-3 | Ar-3 | Ar-2 |
| Ar-2 | Ar-3 | Ar-3 | Ar-3 |
| Ar-2 | Ar-3 | Ar-3 | Ar-4 |
| Ar-2 | Ar-3 | Ar-3 | Ar-5 |
| Ar-2 | Ar-3 | Ar-3 | Ar-6 |
| Ar-2 | Ar-3 | Ar-4 | Ar-2 |
| Ar-2 | Ar-3 | Ar-4 | Ar-3 |
| Ar-2 | Ar-3 | Ar-4 | Ar-4 |
| Ar-2 | Ar-3 | Ar-4 | Ar-5 |
| Ar-2 | Ar-3 | Ar-4 | Ar-6 |
| Ar-2 | Ar-3 | Ar-5 | Ar-2 |
| Ar-2 | Ar-3 | Ar-5 | Ar-3 |
| Ar-2 | Ar-3 | Ar-5 | Ar-4 |
| Ar-2 | Ar-3 | Ar-5 | Ar-5 |
| Ar-2 | Ar-3 | Ar-5 | Ar-6 |
| Ar-2 | Ar-3 | Ar-6 | Ar-2 |
| Ar-2 | Ar-3 | Ar-6 | Ar-3 |
| Ar-2 | Ar-3 | Ar-6 | Ar-4 |
| Ar-2 | Ar-3 | Ar-6 | Ar-5 |
| Ar-2 | Ar-3 | Ar-6 | Ar-6 |
| Ar-2 | Ar-4 | Ar-1 | Ar-3 |
| Ar-2 | Ar-4 | Ar-1 | Ar-4 |
| Ar-2 | Ar-4 | Ar-1 | Ar-5 |
| Ar-2 | Ar-4 | Ar-1 | Ar-6 |
| Ar-2 | Ar-4 | Ar-2 | Ar-3 |
| Ar-2 | Ar-4 | Ar-2 | Ar-4 |
| Ar-2 | Ar-4 | Ar-2 | Ar-5 |
| Ar-2 | Ar-4 | Ar-2 | Ar-6 |
| Ar-2 | Ar-4 | Ar-3 | Ar-3 |
| Ar-2 | Ar-4 | Ar-3 | Ar-4 |
| Ar-2 | Ar-4 | Ar-3 | Ar-5 |
| Ar-2 | Ar-4 | Ar-3 | Ar-6 |

TABLE 1-6

| R3 | R5 | R6 | R8 |
|---|---|---|---|
| Ar-2 | Ar-4 | Ar-4 | Ar-2 |
| Ar-2 | Ar-4 | Ar-4 | Ar-3 |
| Ar-2 | Ar-4 | Ar-4 | Ar-4 |
| Ar-2 | Ar-4 | Ar-4 | Ar-5 |
| Ar-2 | Ar-4 | Ar-4 | Ar-6 |
| Ar-2 | Ar-4 | Ar-5 | Ar-2 |
| Ar-2 | Ar-4 | Ar-5 | Ar-3 |
| Ar-2 | Ar-4 | Ar-5 | Ar-4 |
| Ar-2 | Ar-4 | Ar-5 | Ar-5 |
| Ar-2 | Ar-4 | Ar-5 | Ar-6 |
| Ar-2 | Ar-4 | Ar-6 | Ar-2 |
| Ar-2 | Ar-4 | Ar-6 | Ar-3 |
| Ar-2 | Ar-4 | Ar-6 | Ar-4 |
| Ar-2 | Ar-4 | Ar-6 | Ar-5 |
| Ar-2 | Ar-4 | Ar-6 | Ar-6 |
| Ar-2 | Ar-5 | Ar-1 | Ar-3 |
| Ar-2 | Ar-5 | Ar-1 | Ar-4 |
| Ar-2 | Ar-5 | Ar-1 | Ar-5 |
| Ar-2 | Ar-5 | Ar-1 | Ar-6 |
| Ar-2 | Ar-5 | Ar-2 | Ar-3 |
| Ar-2 | Ar-5 | Ar-2 | Ar-4 |
| Ar-2 | Ar-5 | Ar-2 | Ar-5 |
| Ar-2 | Ar-5 | Ar-2 | Ar-6 |
| Ar-2 | Ar-5 | Ar-3 | Ar-3 |
| Ar-2 | Ar-5 | Ar-3 | Ar-4 |
| Ar-2 | Ar-5 | Ar-3 | Ar-5 |
| Ar-2 | Ar-5 | Ar-3 | Ar-6 |
| Ar-2 | Ar-5 | Ar-4 | Ar-3 |
| Ar-2 | Ar-5 | Ar-4 | Ar-4 |
| Ar-2 | Ar-5 | Ar-4 | Ar-5 |
| Ar-2 | Ar-5 | Ar-4 | Ar-6 |
| Ar-2 | Ar-5 | Ar-5 | Ar-2 |
| Ar-2 | Ar-5 | Ar-5 | Ar-3 |
| Ar-2 | Ar-5 | Ar-5 | Ar-4 |
| Ar-2 | Ar-5 | Ar-5 | Ar-5 |
| Ar-2 | Ar-5 | Ar-5 | Ar-6 |
| Ar-2 | Ar-5 | Ar-6 | Ar-2 |
| Ar-2 | Ar-5 | Ar-6 | Ar-3 |
| Ar-2 | Ar-5 | Ar-6 | Ar-4 |
| Ar-2 | Ar-5 | Ar-6 | Ar-5 |
| Ar-2 | Ar-5 | Ar-6 | Ar-6 |
| Ar-2 | Ar-6 | Ar-1 | Ar-3 |
| Ar-2 | Ar-6 | Ar-1 | Ar-4 |
| Ar-2 | Ar-6 | Ar-1 | Ar-5 |
| Ar-2 | Ar-6 | Ar-1 | Ar-6 |
| Ar-2 | Ar-6 | Ar-2 | Ar-3 |
| Ar-2 | Ar-6 | Ar-2 | Ar-4 |
| Ar-2 | Ar-6 | Ar-2 | Ar-5 |
| Ar-2 | Ar-6 | Ar-2 | Ar-6 |
| Ar-2 | Ar-6 | Ar-3 | Ar-3 |
| Ar-2 | Ar-6 | Ar-3 | Ar-4 |
| Ar-2 | Ar-6 | Ar-3 | Ar-5 |
| Ar-2 | Ar-6 | Ar-3 | Ar-6 |
| Ar-2 | Ar-6 | Ar-4 | Ar-3 |
| Ar-2 | Ar-6 | Ar-4 | Ar-4 |
| Ar-2 | Ar-6 | Ar-4 | Ar-5 |
| Ar-2 | Ar-6 | Ar-4 | Ar-6 |
| Ar-2 | Ar-6 | Ar-5 | Ar-3 |
| Ar-2 | Ar-6 | Ar-5 | Ar-4 |
| Ar-2 | Ar-6 | Ar-5 | Ar-5 |
| Ar-2 | Ar-6 | Ar-5 | Ar-6 |

TABLE 1-7

| R3 | R5 | R6 | R8 |
|---|---|---|---|
| Ar-2 | Ar-6 | Ar-6 | Ar-2 |
| Ar-2 | Ar-6 | Ar-6 | Ar-3 |
| Ar-2 | Ar-6 | Ar-6 | Ar-4 |
| Ar-2 | Ar-6 | Ar-6 | Ar-5 |
| Ar-2 | Ar-6 | Ar-6 | Ar-6 |
| Ar-3 | Ar-1 | Ar-1 | Ar-3 |
| Ar-3 | Ar-1 | Ar-1 | Ar-4 |
| Ar-3 | Ar-1 | Ar-1 | Ar-5 |
| Ar-3 | Ar-1 | Ar-1 | Ar-6 |
| Ar-3 | Ar-1 | Ar-2 | Ar-3 |
| Ar-3 | Ar-1 | Ar-2 | Ar-4 |

TABLE 1-7-continued

| R3 | R5 | R6 | R8 |
|---|---|---|---|
| Ar-3 | Ar-1 | Ar-2 | Ar-5 |
| Ar-3 | Ar-1 | Ar-2 | Ar-6 |
| Ar-3 | Ar-1 | Ar-3 | Ar-3 |
| Ar-3 | Ar-1 | Ar-3 | Ar-4 |
| Ar-3 | Ar-1 | Ar-3 | Ar-5 |
| Ar-3 | Ar-1 | Ar-3 | Ar-6 |
| Ar-3 | Ar-1 | Ar-4 | Ar-3 |
| Ar-3 | Ar-1 | Ar-4 | Ar-4 |
| Ar-3 | Ar-1 | Ar-4 | Ar-5 |
| Ar-3 | Ar-1 | Ar-4 | Ar-6 |
| Ar-3 | Ar-1 | Ar-5 | Ar-3 |
| Ar-3 | Ar-1 | Ar-5 | Ar-4 |
| Ar-3 | Ar-1 | Ar-5 | Ar-5 |
| Ar-3 | Ar-1 | Ar-5 | Ar-6 |
| Ar-3 | Ar-1 | Ar-6 | Ar-3 |
| Ar-3 | Ar-1 | Ar-6 | Ar-4 |
| Ar-3 | Ar-1 | Ar-6 | Ar-5 |
| Ar-3 | Ar-1 | Ar-6 | Ar-6 |
| Ar-3 | Ar-2 | Ar-1 | Ar-4 |
| Ar-3 | Ar-2 | Ar-1 | Ar-5 |
| Ar-3 | Ar-2 | Ar-1 | Ar-6 |
| Ar-3 | Ar-2 | Ar-2 | Ar-3 |
| Ar-3 | Ar-2 | Ar-2 | Ar-4 |
| Ar-3 | Ar-2 | Ar-2 | Ar-5 |
| Ar-3 | Ar-2 | Ar-2 | Ar-6 |
| Ar-3 | Ar-2 | Ar-3 | Ar-3 |
| Ar-3 | Ar-2 | Ar-3 | Ar-4 |
| Ar-3 | Ar-2 | Ar-3 | Ar-5 |
| Ar-3 | Ar-2 | Ar-3 | Ar-6 |
| Ar-3 | Ar-2 | Ar-4 | Ar-3 |
| Ar-3 | Ar-2 | Ar-4 | Ar-4 |
| Ar-3 | Ar-2 | Ar-4 | Ar-5 |
| Ar-3 | Ar-2 | Ar-4 | Ar-6 |
| Ar-3 | Ar-2 | Ar-5 | Ar-3 |
| Ar-3 | Ar-2 | Ar-5 | Ar-4 |
| Ar-3 | Ar-2 | Ar-5 | Ar-5 |
| Ar-3 | Ar-2 | Ar-5 | Ar-6 |
| Ar-3 | Ar-2 | Ar-6 | Ar-3 |
| Ar-3 | Ar-2 | Ar-6 | Ar-4 |
| Ar-3 | Ar-2 | Ar-6 | Ar-5 |
| Ar-3 | Ar-2 | Ar-6 | Ar-6 |
| Ar-3 | Ar-3 | Ar-1 | Ar-4 |
| Ar-3 | Ar-3 | Ar-1 | Ar-5 |
| Ar-3 | Ar-3 | Ar-1 | Ar-6 |
| Ar-3 | Ar-3 | Ar-2 | Ar-4 |
| Ar-3 | Ar-3 | Ar-2 | Ar-5 |
| Ar-3 | Ar-3 | Ar-2 | Ar-6 |
| Ar-3 | Ar-3 | Ar-3 | Ar-3 |
| Ar-3 | Ar-3 | Ar-3 | Ar-4 |
| Ar-3 | Ar-3 | Ar-3 | Ar-5 |

TABLE 1-8

| R3 | R5 | R6 | R8 |
|---|---|---|---|
| Ar-3 | Ar-3 | Ar-3 | Ar-6 |
| Ar-3 | Ar-3 | Ar-4 | Ar-3 |
| Ar-3 | Ar-3 | Ar-4 | Ar-4 |
| Ar-3 | Ar-3 | Ar-4 | Ar-5 |
| Ar-3 | Ar-3 | Ar-4 | Ar-6 |
| Ar-3 | Ar-3 | Ar-5 | Ar-3 |
| Ar-3 | Ar-3 | Ar-5 | Ar-4 |
| Ar-3 | Ar-3 | Ar-5 | Ar-5 |
| Ar-3 | Ar-3 | Ar-5 | Ar-6 |
| Ar-3 | Ar-3 | Ar-6 | Ar-3 |
| Ar-3 | Ar-3 | Ar-6 | Ar-4 |
| Ar-3 | Ar-3 | Ar-6 | Ar-5 |
| Ar-3 | Ar-3 | Ar-6 | Ar-6 |
| Ar-3 | Ar-4 | Ar-1 | Ar-4 |
| Ar-3 | Ar-4 | Ar-1 | Ar-5 |
| Ar-3 | Ar-4 | Ar-1 | Ar-6 |
| Ar-3 | Ar-4 | Ar-2 | Ar-4 |
| Ar-3 | Ar-4 | Ar-2 | Ar-5 |
| Ar-3 | Ar-4 | Ar-2 | Ar-6 |
| Ar-3 | Ar-4 | Ar-3 | Ar-4 |

TABLE 1-8-continued

| R3 | R5 | R6 | R8 |
|---|---|---|---|
| Ar-3 | Ar-4 | Ar-3 | Ar-5 |
| Ar-3 | Ar-4 | Ar-3 | Ar-6 |
| Ar-3 | Ar-4 | Ar-4 | Ar-3 |
| Ar-3 | Ar-4 | Ar-4 | Ar-4 |
| Ar-3 | Ar-4 | Ar-4 | Ar-5 |
| Ar-3 | Ar-4 | Ar-4 | Ar-6 |
| Ar-3 | Ar-4 | Ar-5 | Ar-3 |
| Ar-3 | Ar-4 | Ar-5 | Ar-4 |
| Ar-3 | Ar-4 | Ar-5 | Ar-5 |
| Ar-3 | Ar-4 | Ar-5 | Ar-6 |
| Ar-3 | Ar-4 | Ar-6 | Ar-3 |
| Ar-3 | Ar-4 | Ar-6 | Ar-4 |
| Ar-3 | Ar-4 | Ar-6 | Ar-5 |
| Ar-3 | Ar-4 | Ar-6 | Ar-6 |
| Ar-3 | Ar-5 | Ar-1 | Ar-4 |
| Ar-3 | Ar-5 | Ar-1 | Ar-5 |
| Ar-3 | Ar-5 | Ar-1 | Ar-6 |
| Ar-3 | Ar-5 | Ar-2 | Ar-4 |
| Ar-3 | Ar-5 | Ar-2 | Ar-5 |
| Ar-3 | Ar-5 | Ar-2 | Ar-6 |
| Ar-3 | Ar-5 | Ar-3 | Ar-4 |
| Ar-3 | Ar-5 | Ar-3 | Ar-5 |
| Ar-3 | Ar-5 | Ar-3 | Ar-6 |
| Ar-3 | Ar-5 | Ar-4 | Ar-4 |
| Ar-3 | Ar-5 | Ar-4 | Ar-5 |
| Ar-3 | Ar-5 | Ar-4 | Ar-6 |
| Ar-3 | Ar-5 | Ar-5 | Ar-3 |
| Ar-3 | Ar-5 | Ar-5 | Ar-4 |
| Ar-3 | Ar-5 | Ar-5 | Ar-5 |
| Ar-3 | Ar-5 | Ar-5 | Ar-6 |
| Ar-3 | Ar-5 | Ar-6 | Ar-3 |
| Ar-3 | Ar-5 | Ar-6 | Ar-4 |
| Ar-3 | Ar-5 | Ar-6 | Ar-5 |
| Ar-3 | Ar-5 | Ar-6 | Ar-6 |
| Ar-3 | Ar-6 | Ar-1 | Ar-4 |
| Ar-3 | Ar-6 | Ar-1 | Ar-5 |
| Ar-3 | Ar-6 | Ar-1 | Ar-6 |
| Ar-3 | Ar-6 | Ar-2 | Ar-4 |
| Ar-3 | Ar-6 | Ar-2 | Ar-5 |
| Ar-3 | Ar-6 | Ar-2 | Ar-6 |

TABLE 1-9

| R3 | R5 | R6 | R8 |
|---|---|---|---|
| Ar-3 | Ar-6 | Ar-3 | Ar-4 |
| Ar-3 | Ar-6 | Ar-3 | Ar-5 |
| Ar-3 | Ar-6 | Ar-3 | Ar-6 |
| Ar-3 | Ar-6 | Ar-4 | Ar-4 |
| Ar-3 | Ar-6 | Ar-4 | Ar-5 |
| Ar-3 | Ar-6 | Ar-4 | Ar-6 |
| Ar-3 | Ar-6 | Ar-5 | Ar-4 |
| Ar-3 | Ar-6 | Ar-5 | Ar-5 |
| Ar-3 | Ar-6 | Ar-5 | Ar-6 |
| Ar-3 | Ar-6 | Ar-6 | Ar-3 |
| Ar-3 | Ar-6 | Ar-6 | Ar-4 |
| Ar-3 | Ar-6 | Ar-6 | Ar-5 |
| Ar-3 | Ar-6 | Ar-6 | Ar-6 |
| Ar-4 | Ar-1 | Ar-1 | Ar-4 |
| Ar-4 | Ar-1 | Ar-1 | Ar-5 |
| Ar-4 | Ar-1 | Ar-1 | Ar-6 |
| Ar-4 | Ar-1 | Ar-2 | Ar-4 |
| Ar-4 | Ar-1 | Ar-2 | Ar-5 |
| Ar-4 | Ar-1 | Ar-2 | Ar-6 |
| Ar-4 | Ar-1 | Ar-3 | Ar-4 |
| Ar-4 | Ar-1 | Ar-3 | Ar-5 |
| Ar-4 | Ar-1 | Ar-3 | Ar-6 |
| Ar-4 | Ar-1 | Ar-4 | Ar-4 |
| Ar-4 | Ar-1 | Ar-4 | Ar-5 |
| Ar-4 | Ar-1 | Ar-4 | Ar-6 |
| Ar-4 | Ar-1 | Ar-5 | Ar-4 |
| Ar-4 | Ar-1 | Ar-5 | Ar-5 |
| Ar-4 | Ar-1 | Ar-5 | Ar-6 |
| Ar-4 | Ar-1 | Ar-6 | Ar-4 |
| Ar-4 | Ar-1 | Ar-6 | Ar-5 |

TABLE 1-9-continued

| R3 | R5 | R6 | R8 |
|---|---|---|---|
| Ar-4 | Ar-1 | Ar-6 | Ar-6 |
| Ar-4 | Ar-2 | Ar-1 | Ar-5 |
| Ar-4 | Ar-2 | Ar-2 | Ar-4 |
| Ar-4 | Ar-2 | Ar-2 | Ar-5 |
| Ar-4 | Ar-2 | Ar-2 | Ar-6 |
| Ar-4 | Ar-2 | Ar-3 | Ar-4 |
| Ar-4 | Ar-2 | Ar-3 | Ar-5 |
| Ar-4 | Ar-2 | Ar-3 | Ar-6 |
| Ar-4 | Ar-2 | Ar-4 | Ar-4 |
| Ar-4 | Ar-2 | Ar-4 | Ar-5 |
| Ar-4 | Ar-2 | Ar-4 | Ar-6 |
| Ar-4 | Ar-2 | Ar-5 | Ar-4 |
| Ar-4 | Ar-2 | Ar-5 | Ar-5 |
| Ar-4 | Ar-2 | Ar-5 | Ar-6 |
| Ar-4 | Ar-2 | Ar-6 | Ar-4 |
| Ar-4 | Ar-2 | Ar-6 | Ar-5 |
| Ar-4 | Ar-2 | Ar-6 | Ar-6 |
| Ar-4 | Ar-3 | Ar-1 | Ar-5 |
| Ar-4 | Ar-3 | Ar-1 | Ar-6 |
| Ar-4 | Ar-3 | Ar-2 | Ar-5 |
| Ar-4 | Ar-3 | Ar-2 | Ar-6 |
| Ar-4 | Ar-3 | Ar-3 | Ar-4 |
| Ar-4 | Ar-3 | Ar-3 | Ar-5 |
| Ar-4 | Ar-3 | Ar-3 | Ar-6 |
| Ar-4 | Ar-3 | Ar-4 | Ar-4 |
| Ar-4 | Ar-3 | Ar-4 | Ar-5 |
| Ar-4 | Ar-3 | Ar-4 | Ar-6 |
| Ar-4 | Ar-3 | Ar-5 | Ar-4 |
| Ar-4 | Ar-3 | Ar-5 | Ar-5 |
| Ar-4 | Ar-3 | Ar-5 | Ar-6 |

TABLE 1-10

| R3 | R5 | R6 | R8 |
|---|---|---|---|
| Ar-4 | Ar-3 | Ar-6 | Ar-4 |
| Ar-4 | Ar-3 | Ar-6 | Ar-5 |
| Ar-4 | Ar-3 | Ar-6 | Ar-6 |
| Ar-4 | Ar-4 | Ar-1 | Ar-5 |
| Ar-4 | Ar-4 | Ar-1 | Ar-6 |
| Ar-4 | Ar-4 | Ar-2 | Ar-5 |
| Ar-4 | Ar-4 | Ar-2 | Ar-6 |
| Ar-4 | Ar-4 | Ar-3 | Ar-5 |
| Ar-4 | Ar-4 | Ar-3 | Ar-6 |
| Ar-4 | Ar-4 | Ar-4 | Ar-4 |
| Ar-4 | Ar-4 | Ar-4 | Ar-5 |
| Ar-4 | Ar-4 | Ar-4 | Ar-6 |
| Ar-4 | Ar-4 | Ar-5 | Ar-4 |
| Ar-4 | Ar-4 | Ar-5 | Ar-5 |
| Ar-4 | Ar-4 | Ar-5 | Ar-6 |
| Ar-4 | Ar-4 | Ar-6 | Ar-4 |
| Ar-4 | Ar-4 | Ar-6 | Ar-5 |
| Ar-4 | Ar-4 | Ar-6 | Ar-6 |
| Ar-4 | Ar-5 | Ar-1 | Ar-5 |
| Ar-4 | Ar-5 | Ar-1 | Ar-6 |
| Ar-4 | Ar-5 | Ar-2 | Ar-5 |
| Ar-4 | Ar-5 | Ar-2 | Ar-6 |
| Ar-4 | Ar-5 | Ar-3 | Ar-5 |
| Ar-4 | Ar-5 | Ar-3 | Ar-6 |
| Ar-4 | Ar-5 | Ar-4 | Ar-5 |
| Ar-4 | Ar-5 | Ar-4 | Ar-6 |
| Ar-4 | Ar-5 | Ar-5 | Ar-4 |
| Ar-4 | Ar-5 | Ar-5 | Ar-5 |
| Ar-4 | Ar-5 | Ar-5 | Ar-6 |
| Ar-4 | Ar-5 | Ar-6 | Ar-4 |
| Ar-4 | Ar-5 | Ar-6 | Ar-5 |
| Ar-4 | Ar-5 | Ar-6 | Ar-6 |
| Ar-4 | Ar-6 | Ar-1 | Ar-5 |
| Ar-4 | Ar-6 | Ar-1 | Ar-6 |
| Ar-4 | Ar-6 | Ar-2 | Ar-6 |
| Ar-4 | Ar-6 | Ar-3 | Ar-5 |
| Ar-4 | Ar-6 | Ar-3 | Ar-6 |
| Ar-4 | Ar-6 | Ar-4 | Ar-5 |

TABLE 1-10-continued

| R3 | R5 | R6 | R8 |
|---|---|---|---|
| Ar-4 | Ar-6 | Ar-4 | Ar-6 |
| Ar-4 | Ar-6 | Ar-5 | Ar-5 |
| Ar-4 | Ar-6 | Ar-5 | Ar-6 |
| Ar-4 | Ar-6 | Ar-6 | Ar-4 |
| Ar-4 | Ar-6 | Ar-6 | Ar-5 |
| Ar-4 | Ar-6 | Ar-6 | Ar-6 |
| Ar-5 | Ar-1 | Ar-1 | Ar-5 |
| Ar-5 | Ar-1 | Ar-1 | Ar-6 |
| Ar-5 | Ar-1 | Ar-2 | Ar-5 |
| Ar-5 | Ar-1 | Ar-2 | Ar-6 |
| Ar-5 | Ar-1 | Ar-3 | Ar-5 |
| Ar-5 | Ar-1 | Ar-3 | Ar-6 |
| Ar-5 | Ar-1 | Ar-4 | Ar-5 |
| Ar-5 | Ar-1 | Ar-4 | Ar-6 |
| Ar-5 | Ar-1 | Ar-5 | Ar-5 |
| Ar-5 | Ar-1 | Ar-5 | Ar-6 |
| Ar-5 | Ar-1 | Ar-6 | Ar-5 |
| Ar-5 | Ar-1 | Ar-6 | Ar-6 |
| Ar-5 | Ar-2 | Ar-1 | Ar-6 |
| Ar-5 | Ar-2 | Ar-2 | Ar-5 |
| Ar-5 | Ar-2 | Ar-2 | Ar-6 |
| Ar-5 | Ar-2 | Ar-3 | Ar-5 |
| Ar-5 | Ar-2 | Ar-3 | Ar-6 |

TABLE 1-11

| R3 | R5 | R6 | R8 |
|---|---|---|---|
| Ar-5 | Ar-2 | Ar-4 | Ar-5 |
| Ar-5 | Ar-2 | Ar-4 | Ar-6 |
| Ar-5 | Ar-2 | Ar-5 | Ar-5 |
| Ar-5 | Ar-2 | Ar-5 | Ar-6 |
| Ar-5 | Ar-2 | Ar-6 | Ar-5 |
| Ar-5 | Ar-2 | Ar-6 | Ar-6 |
| Ar-5 | Ar-3 | Ar-1 | Ar-6 |
| Ar-5 | Ar-3 | Ar-2 | Ar-6 |
| Ar-5 | Ar-3 | Ar-3 | Ar-5 |
| Ar-5 | Ar-3 | Ar-3 | Ar-6 |
| Ar-5 | Ar-3 | Ar-4 | Ar-5 |
| Ar-5 | Ar-3 | Ar-4 | Ar-6 |
| Ar-5 | Ar-3 | Ar-5 | Ar-5 |
| Ar-5 | Ar-3 | Ar-5 | Ar-6 |
| Ar-5 | Ar-3 | Ar-6 | Ar-5 |
| Ar-5 | Ar-3 | Ar-6 | Ar-6 |
| Ar-5 | Ar-4 | Ar-1 | Ar-6 |
| Ar-5 | Ar-4 | Ar-2 | Ar-6 |
| Ar-5 | Ar-4 | Ar-3 | Ar-6 |
| Ar-5 | Ar-4 | Ar-4 | Ar-5 |
| Ar-5 | Ar-4 | Ar-4 | Ar-6 |
| Ar-5 | Ar-4 | Ar-5 | Ar-5 |
| Ar-5 | Ar-4 | Ar-5 | Ar-6 |
| Ar-5 | Ar-4 | Ar-6 | Ar-5 |
| Ar-5 | Ar-4 | Ar-6 | Ar-6 |
| Ar-5 | Ar-5 | Ar-1 | Ar-6 |
| Ar-5 | Ar-5 | Ar-2 | Ar-6 |
| Ar-5 | Ar-5 | Ar-3 | Ar-6 |
| Ar-5 | Ar-5 | Ar-4 | Ar-6 |
| Ar-5 | Ar-5 | Ar-5 | Ar-5 |
| Ar-5 | Ar-5 | Ar-5 | Ar-6 |
| Ar-5 | Ar-5 | Ar-6 | Ar-5 |
| Ar-5 | Ar-5 | Ar-6 | Ar-6 |
| Ar-5 | Ar-6 | Ar-1 | Ar-6 |
| Ar-5 | Ar-6 | Ar-2 | Ar-6 |
| Ar-5 | Ar-6 | Ar-3 | Ar-6 |
| Ar-5 | Ar-6 | Ar-4 | Ar-6 |
| Ar-5 | Ar-6 | Ar-5 | Ar-5 |
| Ar-5 | Ar-6 | Ar-5 | Ar-6 |
| Ar-5 | Ar-6 | Ar-6 | Ar-5 |
| Ar-5 | Ar-6 | Ar-6 | Ar-6 |
| Ar-6 | Ar-1 | Ar-1 | Ar-6 |
| Ar-6 | Ar-1 | Ar-2 | Ar-6 |
| Ar-6 | Ar-1 | Ar-3 | Ar-6 |
| Ar-6 | Ar-1 | Ar-4 | Ar-6 |
| Ar-6 | Ar-1 | Ar-5 | Ar-6 |
| Ar-6 | Ar-1 | Ar-6 | Ar-6 |
| Ar-6 | Ar-2 | Ar-2 | Ar-6 |

TABLE 1-11-continued

| R3 | R5 | R6 | R8 |
|---|---|---|---|
| Ar-6 | Ar-2 | Ar-3 | Ar-6 |
| Ar-6 | Ar-2 | Ar-4 | Ar-6 |
| Ar-6 | Ar-2 | Ar-5 | Ar-6 |
| Ar-6 | Ar-2 | Ar-6 | Ar-6 |
| Ar-6 | Ar-3 | Ar-3 | Ar-6 |
| Ar-6 | Ar-3 | Ar-4 | Ar-6 |
| Ar-6 | Ar-3 | Ar-5 | Ar-6 |
| Ar-6 | Ar-3 | Ar-6 | Ar-6 |
| Ar-6 | Ar-4 | Ar-4 | Ar-6 |
| Ar-6 | Ar-4 | Ar-5 | Ar-6 |
| Ar-6 | Ar-4 | Ar-6 | Ar-6 |
| Ar-6 | Ar-5 | Ar-5 | Ar-6 |
| Ar-6 | Ar-5 | Ar-6 | Ar-6 |
| Ar-6 | Ar-6 | Ar-6 | Ar-6 |

$R^4$ and $R^7$ are each preferably any of hydrogen, an alkyl group, a carbonyl group, an oxycarbonyl group, and an aryl group and preferably hydrogen or an alkyl group in view of thermal stability. In particular, in view of the easiness of obtaining a narrow full width at half maximum in an emission spectrum, $R^4$ and $R^7$ are each more preferably hydrogen.

$R^{10}$ and $R^{11}$ are each preferably an alkyl group, an aryl group, a heteroaryl group, fluorine, a fluorine-containing alkyl group, a fluorine-containing heteroaryl group, or a fluorine-containing aryl group. In particular, because of being stable against excitation light and the capability of obtaining higher fluorescence quantum yield, $R^{10}$ and $R^{11}$ are each more preferably fluorine or a fluorine-containing aryl group. Furthermore, $R^{10}$ and $R^{11}$ are each still more preferably fluorine in view of the easiness of synthesis.

The fluorine-containing aryl group is an aryl group containing fluorine; examples thereof include a fluorophenyl group, a trifluoromethylphenyl group, and pentafluorophenyl group. The fluorine-containing heteroaryl group is a heteroaryl group containing fluorine; examples thereof include a fluoropyridyl group, a trifluoromethylpyridyl group and trifluoropyridyl group. The fluorine-containing alkyl group is an alkyl group containing fluorine; examples thereof include a trifluoromethyl group and a pentafluoroethyl group.

In General Formula (8), X is preferably C—$R^9$ in view of photostability. When X is C—$R^9$, the substituent $R^9$ has a great influence on the durability of the compound represented by General Formula (8), that is, a temporal reduction in the emission intensity of this compound. Specifically, when $R^9$ is hydrogen, the reactivity of this part is high, and this part and water and oxygen in the air easily react with each other. This phenomenon causes the decomposition of the compound represented by General Formula (8). When $R^9$ is a substituent having a large degree of freedom of the motion of a molecular chain such as an alkyl group, although the reactivity indeed reduces, the compounds flocculate with the lapse of time in the composition, resulting in a reduction in emission intensity caused by concentration quenching. Thus, $R^9$ is preferably a group that is rigid, is small in the degree of freedom of motion, and is difficult to cause flocculation, and specifically preferably any of a substituted or unsubstituted aryl group and a substituted or unsubstituted heteroaryl group.

In view of giving higher fluorescence quantum yield, being more resistant to thermal decomposition, and photostability, X is preferably C—$R^9$ in which $R^9$ is a substituted or unsubstituted aryl group. In view of not impairing emission wavelength, the aryl group is preferably a phenyl group, a biphenyl group, a terphenyl group, a naphthyl group, a fluorenyl group, a phenanthryl group, or an anthracenyl group.

Furthermore, to increase the photostability of the compound represented by General Formula (8), the twist of the carbon-carbon bond between $R^9$ and the pyrromethene skeleton is required to be appropriately reduced, because an excessively large twist causes a reduction in photostability, such as an increase in reactivity against the excitation light. Given these circumstances, $R^9$ is preferably a substituted or unsubstituted phenyl group, a substituted or unsubstituted biphenyl group, a substituted or unsubstituted terphenyl group, or a substituted or unsubstituted naphthyl group, more preferably a substituted or unsubstituted phenyl group, a substituted or unsubstituted biphenyl group, or a substituted or unsubstituted terphenyl group, and particularly preferably a substituted or unsubstituted phenyl group.

$R^9$ is preferably an appropriately bulky substituent. $R^9$ has bulkiness to some extent, whereby the flocculation of molecules can be prevented. Consequently, the emission efficiency and durability of the compound further improve.

A further preferred example of the bulky substituent is the structure of $R^9$ represented by the following General Formula (9).

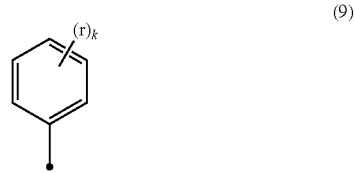

(9)

In General Formula (9), r Is selected from the group consisting of hydrogen, an alkyl group, a cycloalkyl group, a heterocyclic group, an alkenyl group, a cycloalkenyl group, an alkynyl group, a hydroxy group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a boryl group, and a phosphine oxide group. The symbol k is an integer of 1 to 3. When k is 2 or more, rs may be the same as or different from each other.

In view of the capability of giving higher fluorescence quantum yield, r is preferably a substituted or unsubstituted aryl group. Preferred examples of the aryl group include a phenyl group and a naphthyl group in particular. When r is an aryl group, k in General Formula (9) is preferably 1 or 2, and in view of preventing the flocculation of molecules, k is more preferably 2. Furthermore, when k is 2 or more, at least one of rs is preferably substituted by an alkyl group. Particularly preferred examples of the alkyl group in this case include a methyl group, an ethyl group, and a tert-butyl group in view of thermal stability.

In view of controlling fluorescence wavelength and absorption wavelength and increasing compatibility with the solvent, r is preferably a substituted or unsubstituted alkyl group, a substituted or unsubstituted alkoxy group, or halogen and more preferably a methyl group, an ethyl group, a tert-butyl group, or a methoxy group. In view of dispersibility, r is particularly preferably a tert-butyl group or a methoxy group. The fact that r is a tert-butyl group or a methoxy group is more effective for the prevention of quenching caused by the flocculation of molecules.

As another mode of the compound represented by General Formula (8), at least one of $R^3$ to $R^9$ is preferably an electron withdrawing group. In particular, preferred is (1) at least one of $R^3$ to $R^8$ being an electron withdrawing group, (2) $R^9$ being an electron withdrawing group, or (3) at least one of $R^3$ to $R^8$ being an electron withdrawing group and $R^9$ being an electron withdrawing group. The electron withdrawing group is thus introduced to the pyrromethene skeleton of the compound, whereby the electron density of the pyrromethene skeleton can be greatly reduced. With this reduction in electron density, the stability of the compound against oxygen further improves, and consequently, the durability of the compound can be further improved.

The electron withdrawing group is called also an electron accepting group and is an atomic group that attracts an electron from a substituted atomic group by the inductive effect and/or the resonance effect in the organic electron theory. Examples of the electron withdrawing group include ones having a positive value as a substituent constant (σp (para)) of Hammett's Rule. The substituent constant (σp (para)) of Hammett's Rule can be cited from Kagaku Binran Kiso-Hen Revised 5th Edition (II, p. 380). Although the phenyl group has an example taking a positive value as in the above, the electron withdrawing group does not include the phenyl group in the present invention.

Examples of the electron withdrawing group include —F (σp: +0.06), —Cl (σp: +0.23), —Br (σp: +0.23), —I (σp: +0.18), —$CO_2R^{14}$ (σp: +0.45 when $R^{14}$ is an ethyl group), —$CONH_2$ (σp: +0.38), —$COR^{14}$ (σp: +0.49 when $R^{14}$ is a methyl group), —$CF_3$ (σp: +0.50), —$SO_2R^{14}$ (σp: +0.69 when $R^{14}$ is a methyl group), —$NO_2$ (σp: +0.81). $R^{14}$s each independently represent a hydrogen atom, a substituted or unsubstituted aromatic hydrocarbon group with a ring-forming carbon number of 6 o 30, a substituted or unsubstituted heterocyclic group with a ring-forming carbon number of 5 o 30, a substituted or unsubstituted $C_{1-30}$ alkyl group, or a substituted or unsubstituted $C_{1-30}$ cycloalkyl group. Specific examples of these groups include examples similar to those described above.

Preferred examples of the electron withdrawing group include fluorine, a fluorine-containing aryl group, a fluorine-containing heteroaryl group, a fluorine-containing alkyl group, a substituted or unsubstituted acyl group, a substituted or unsubstituted ester group, a substituted or unsubstituted amide group, a substituted or unsubstituted sulfonyl group, and a cyano group; this is because they are resistant to chemical decomposition.

More preferred examples of the electron withdrawing group include a fluorine-containing alkyl group, a substituted or unsubstituted, acyl group, a substituted or unsubstituted ester group, and a cyano group; this is because they prevent concentration quenching, leading to an effect of improving fluorescence quantum yield. A particularly preferred electron withdrawing group is a substituted or unsubstituted ester group.

One particularly preferred example of the compound represented by General Formula (8) is a case in which all $R^3$, $R^5$, $R^6$, and $R^8$, which may be the same as or different from each other, are substituted or unsubstituted alkyl groups and further X is C—$R^9$ in which $R^9$ is a group represented by General Formula (9). In this case, $R^9$ is particularly preferably the group represented by General Formula (9) in which r is contained as a substituted or unsubstituted phenyl group.

Another particularly preferred example of the compound represented by General Formula (8) is a case in which all $R^3$, $R^5$, $R^6$, and $R^8$, which may be the same as or different from each other, are selected from Ar-1 to Ar-6 described above and further X is C—$R^9$ in which $R^9$ is the group represented by General Formula (9). In this case, $R^9$ is more preferably the group represented by General Formula (9) in which r is contained as a tert-butyl group or a methoxy group and particularly preferably the group represented by General Formula (9) in which r is contained as a methoxy group.

The following shows examples of the compound represented by General Formula (8); this compound is not limited to these examples.

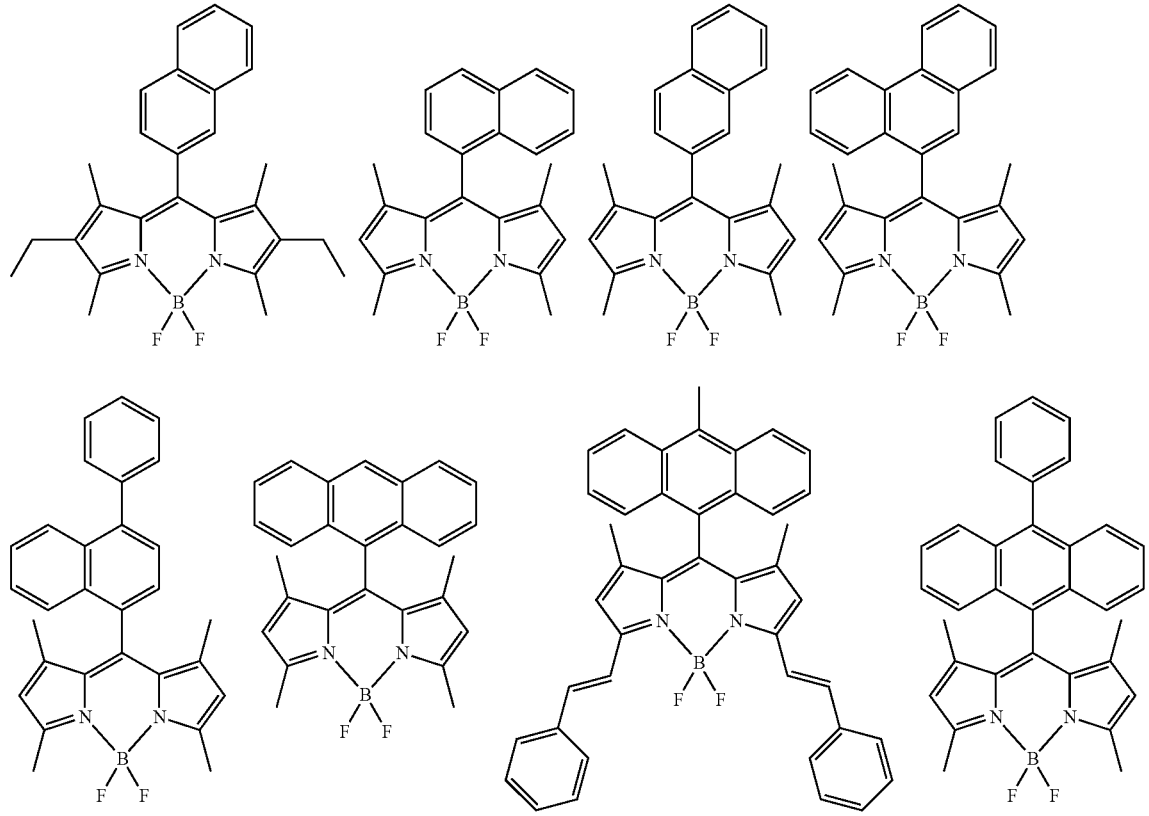

-continued
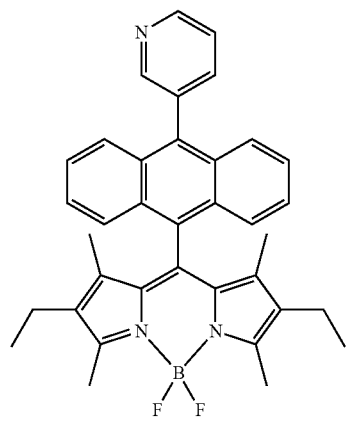 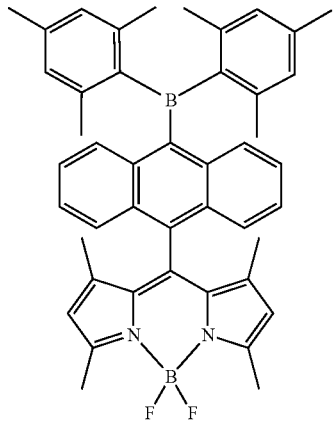 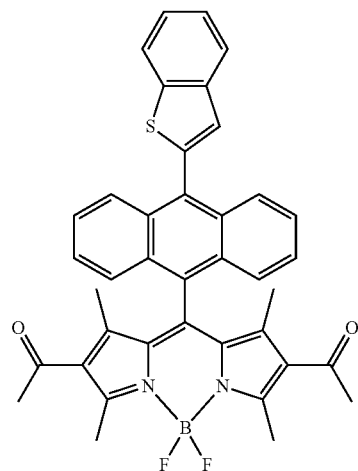
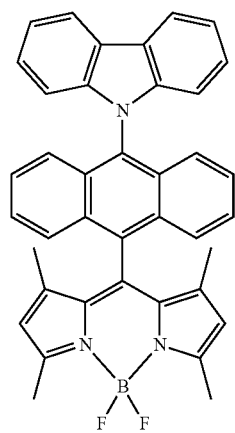 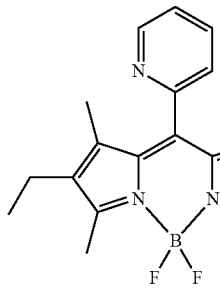 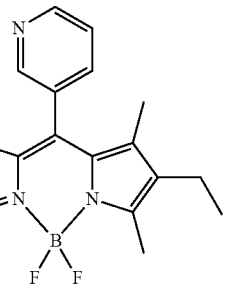
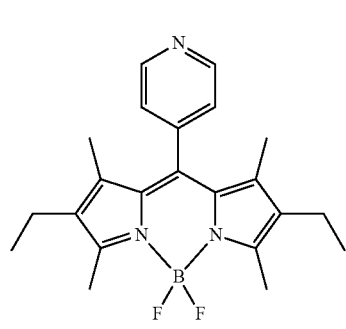 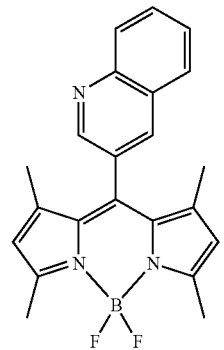 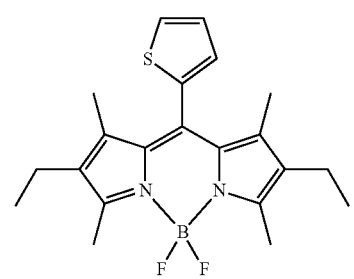
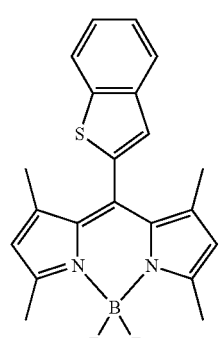 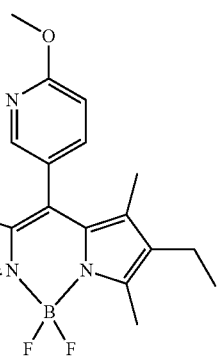 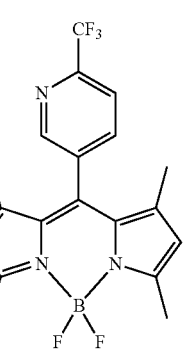 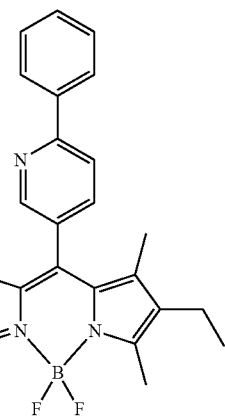

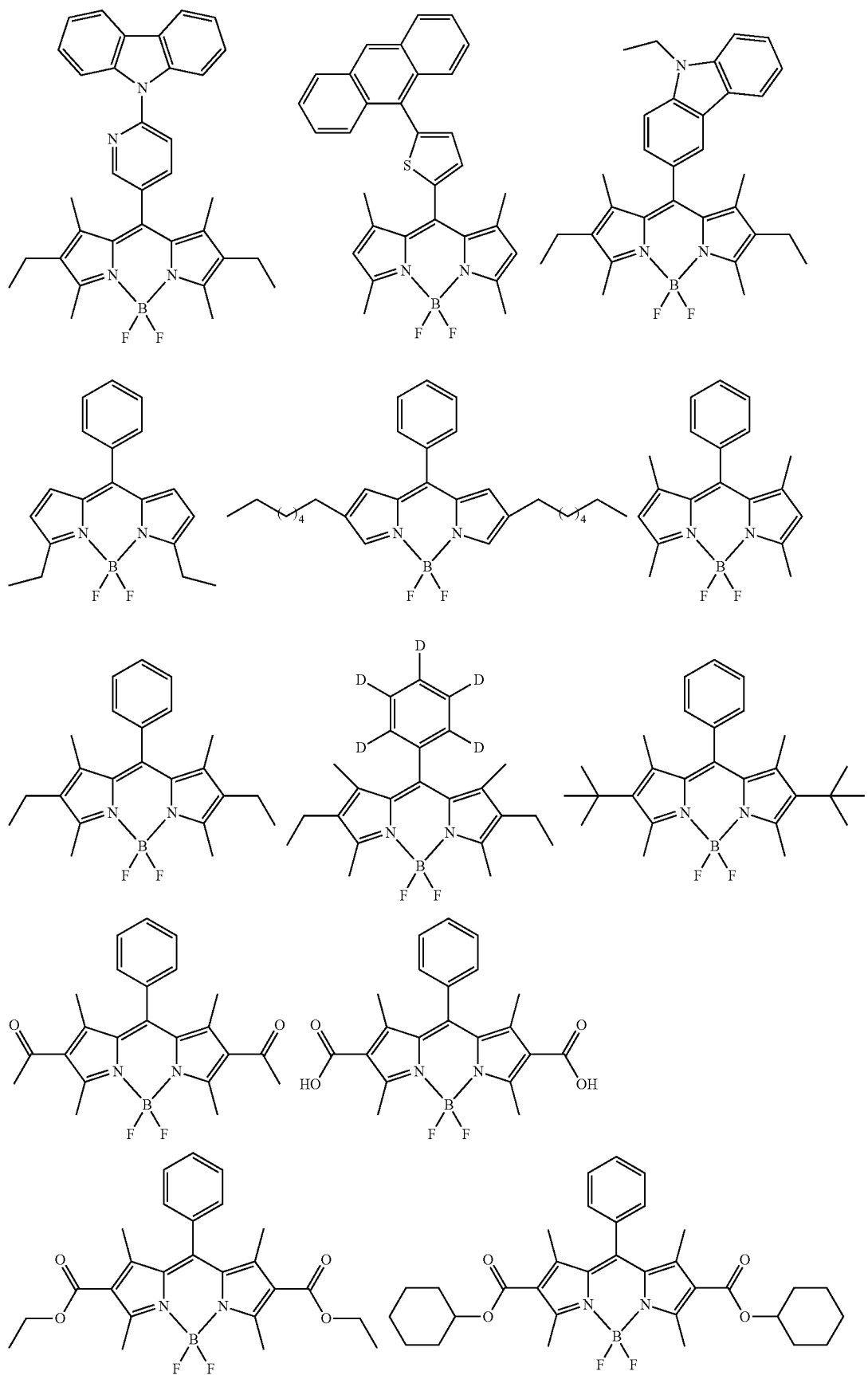

-continued
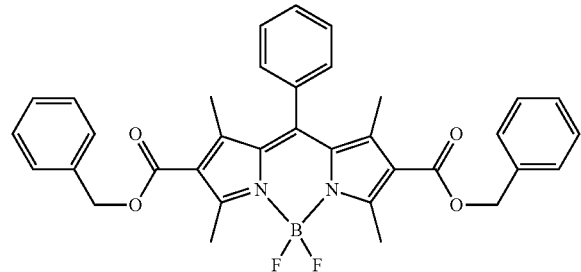
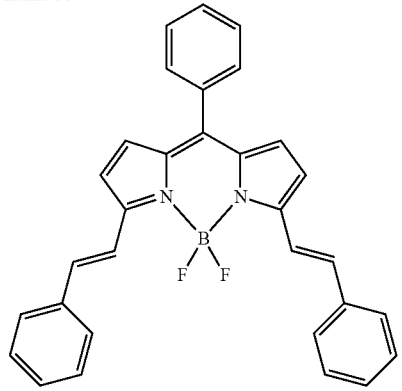
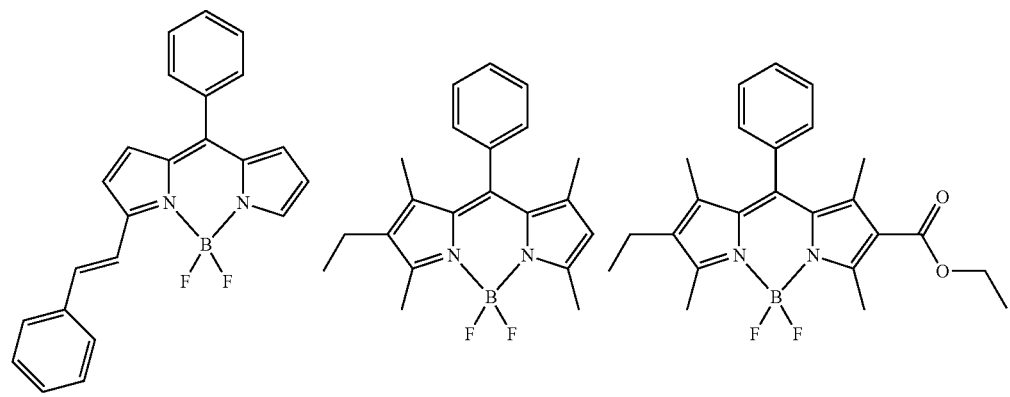
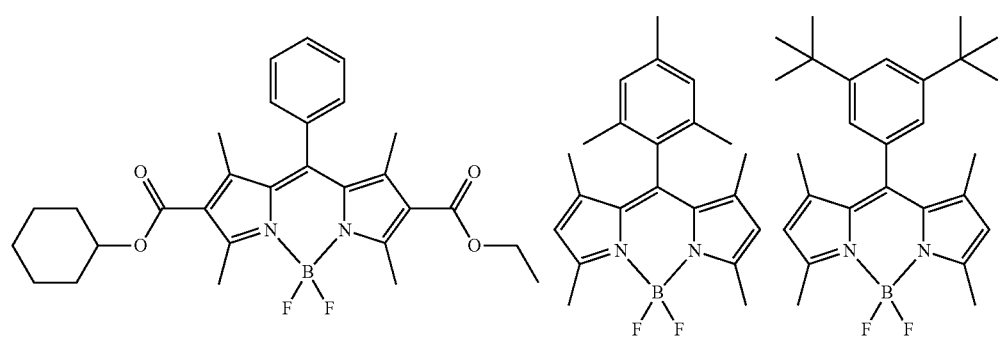
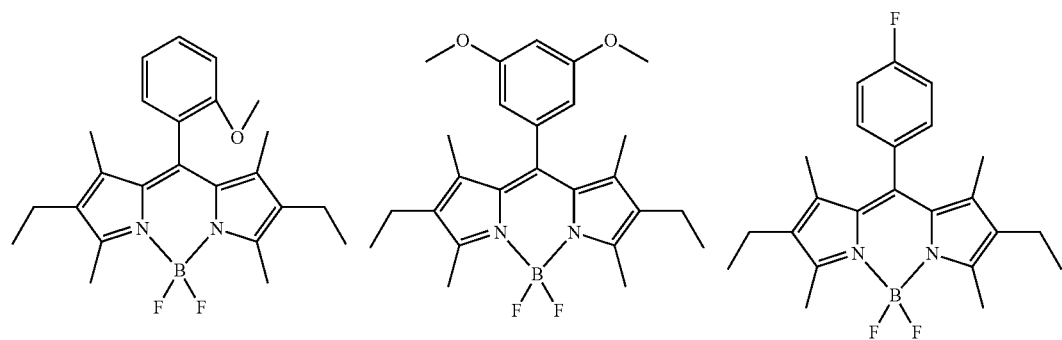

-continued
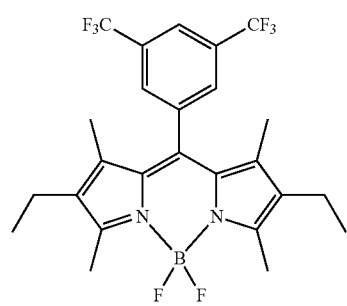
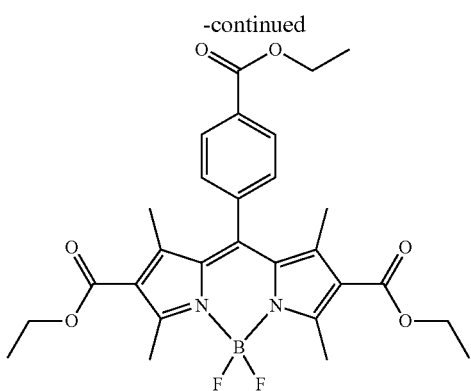
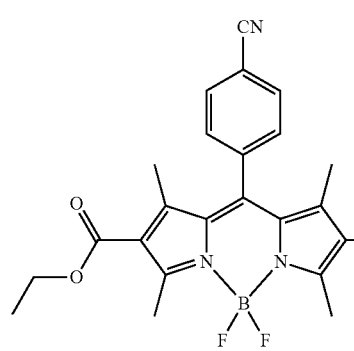
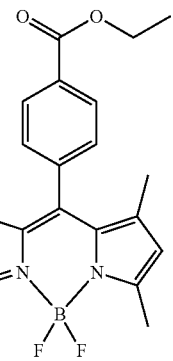
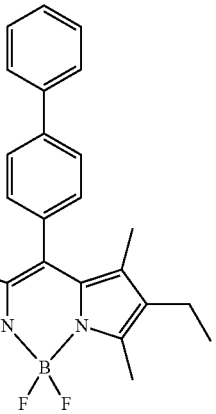
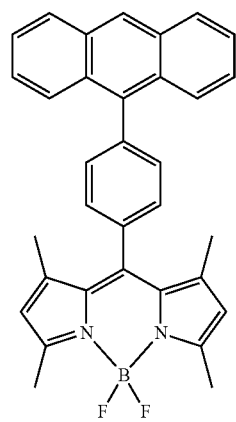
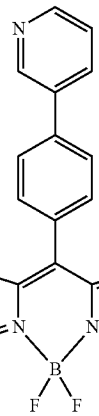
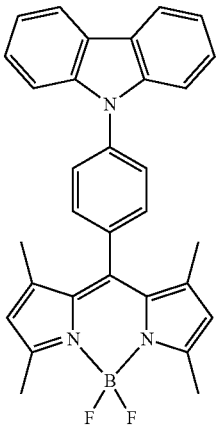
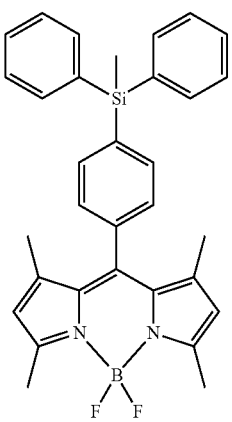
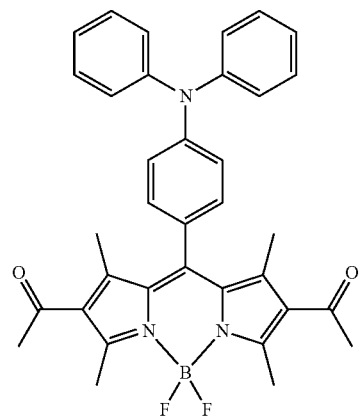
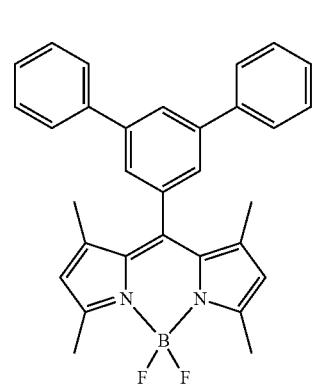
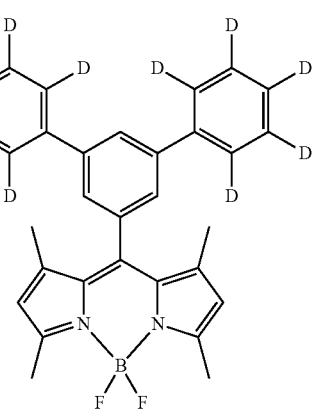

37 38
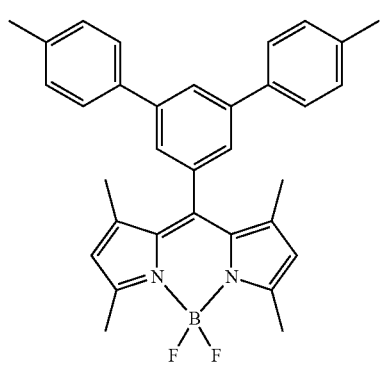 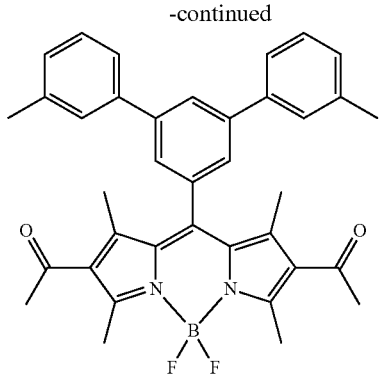 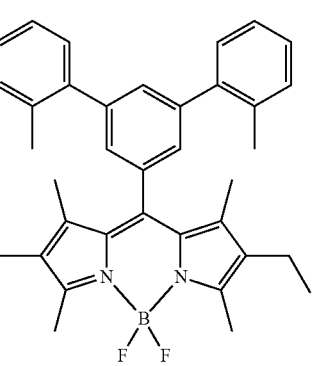
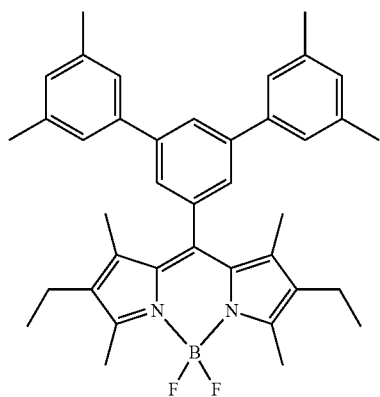 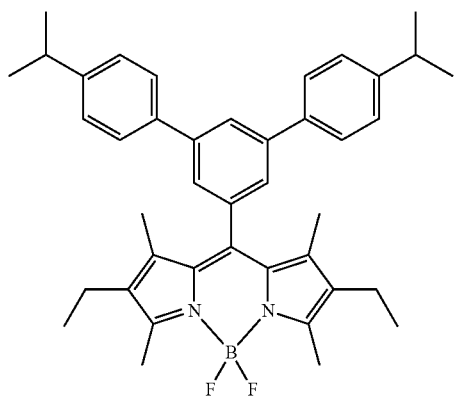
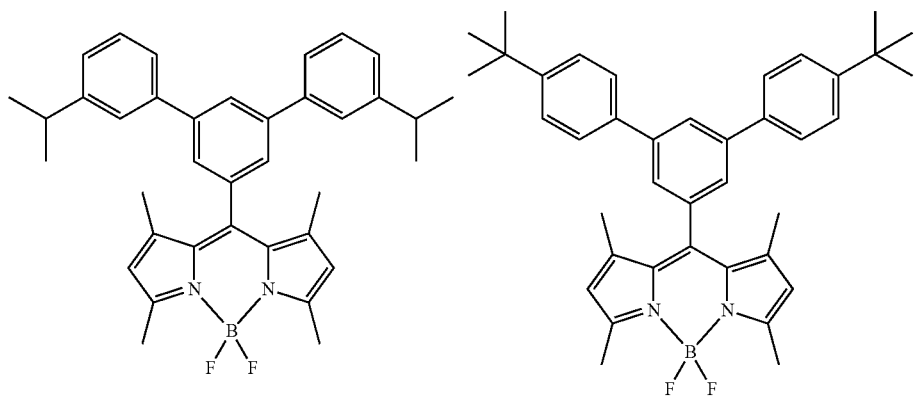
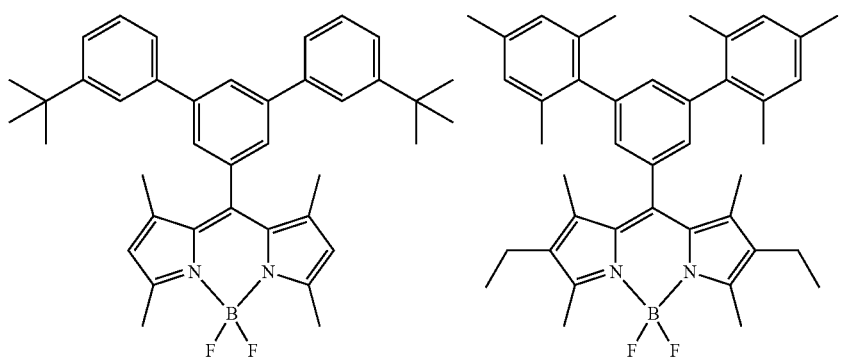

-continued
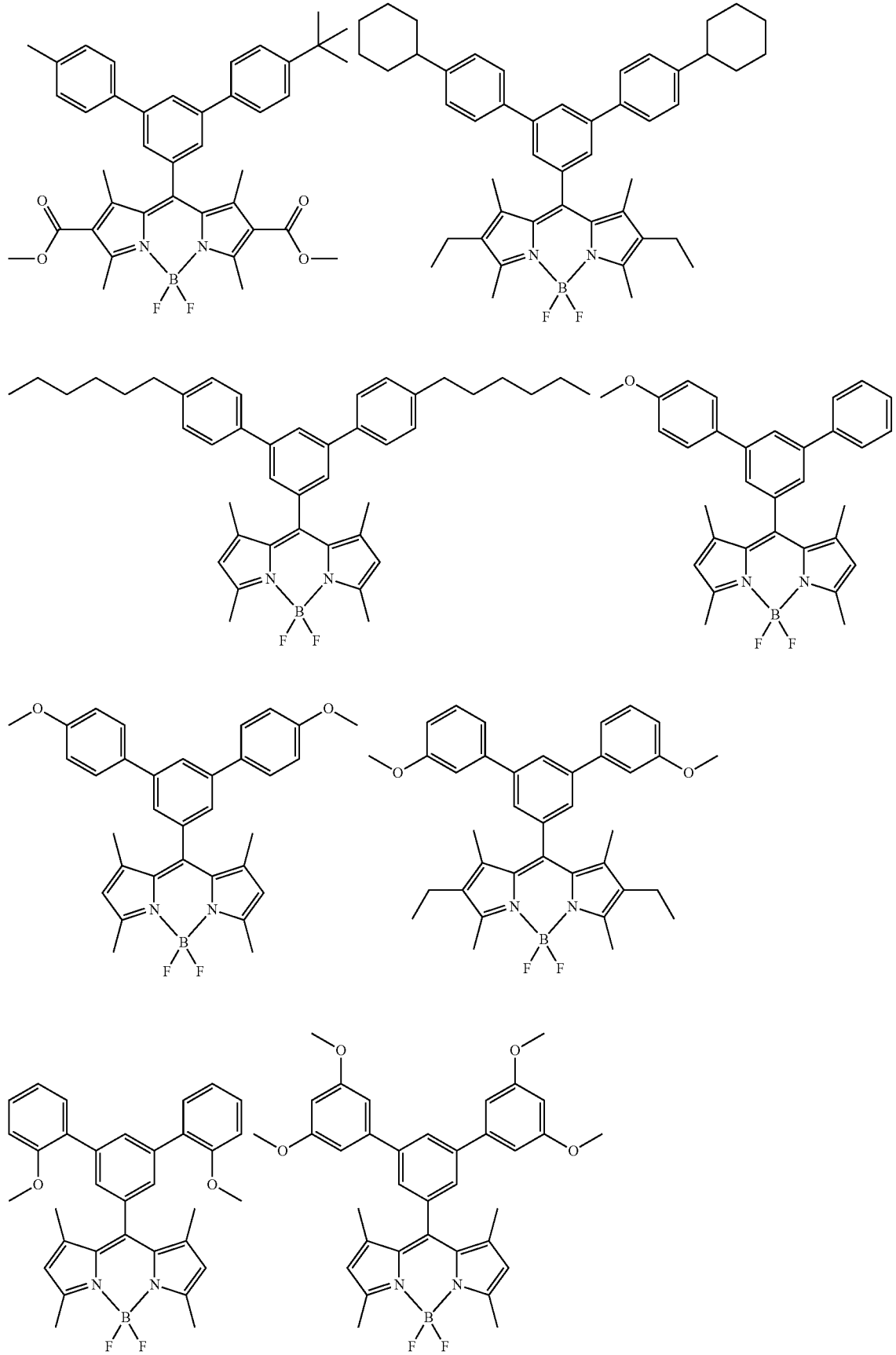

-continued
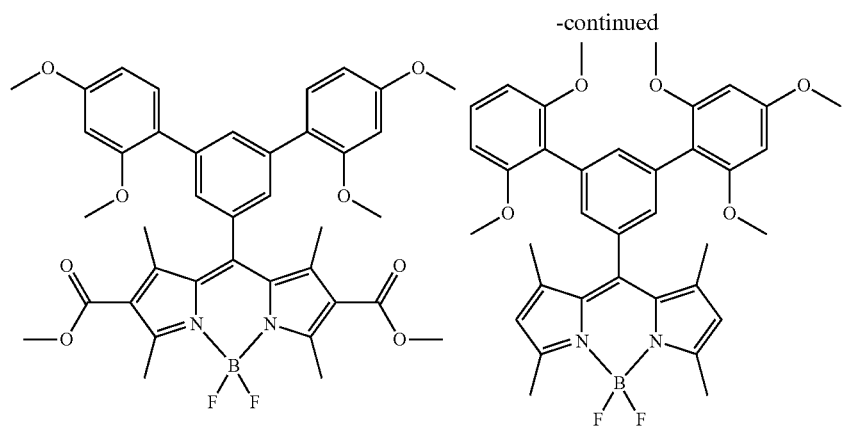
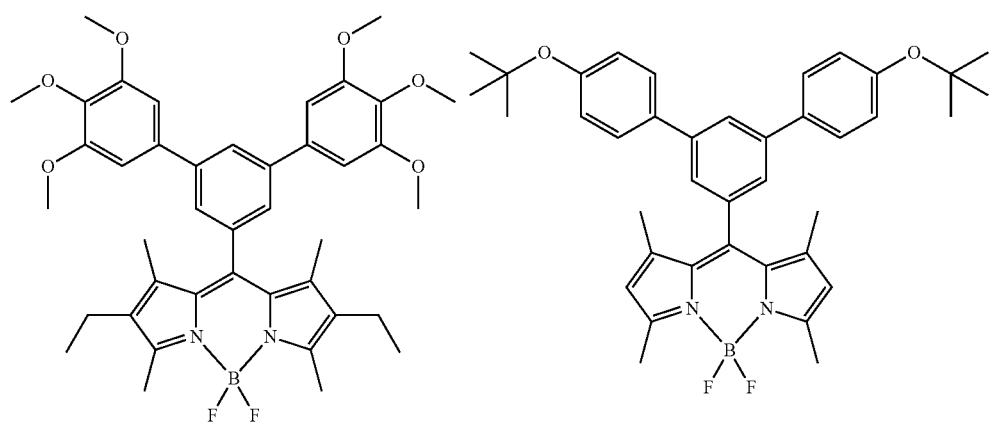
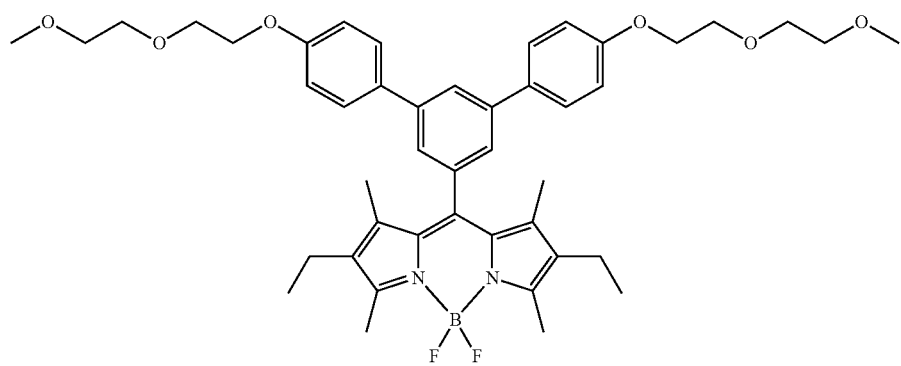
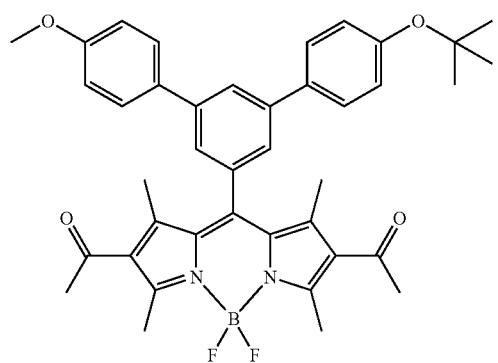

-continued
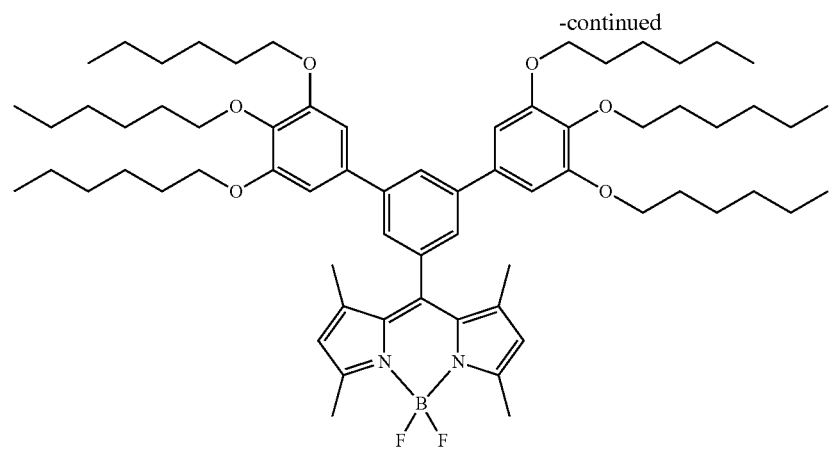
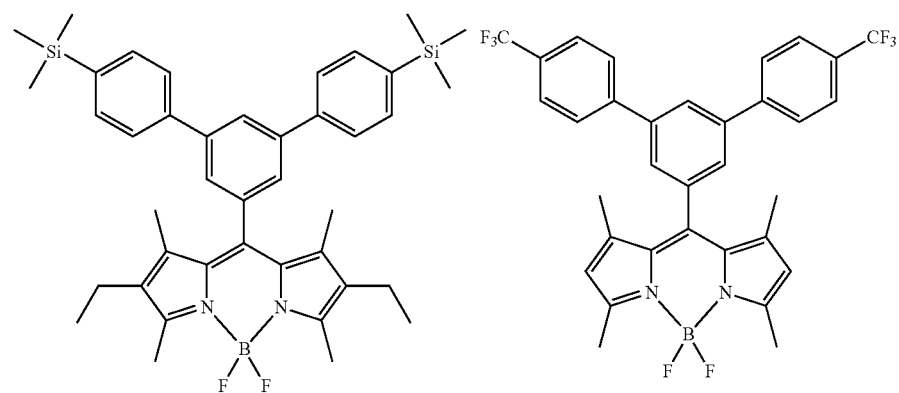
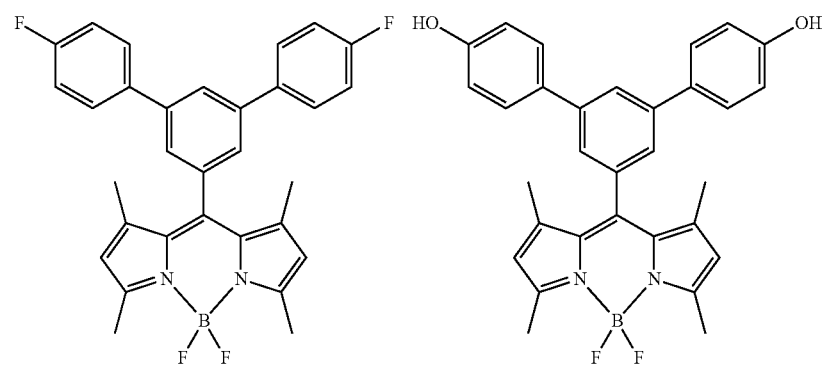
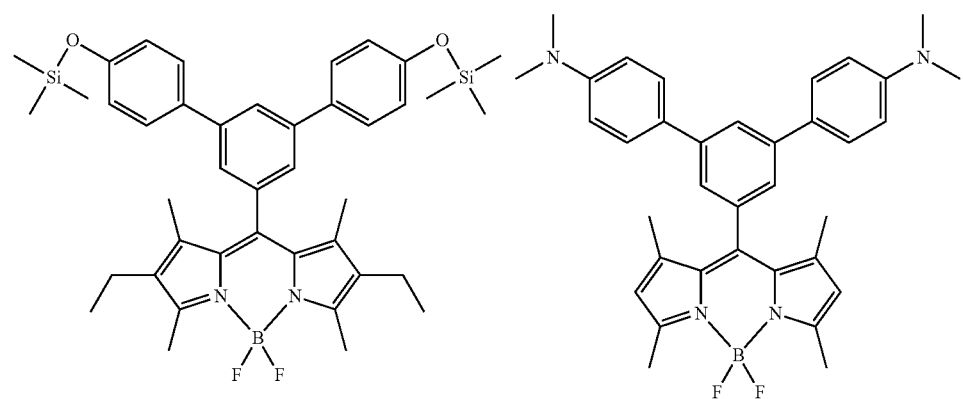

-continued
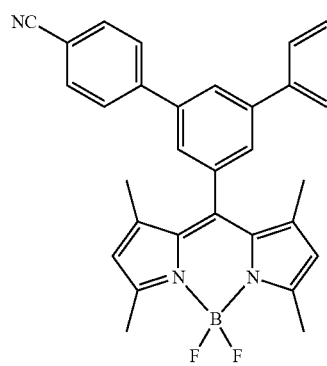 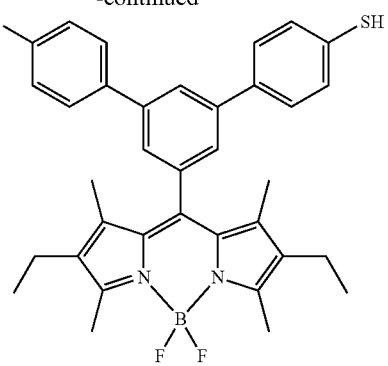
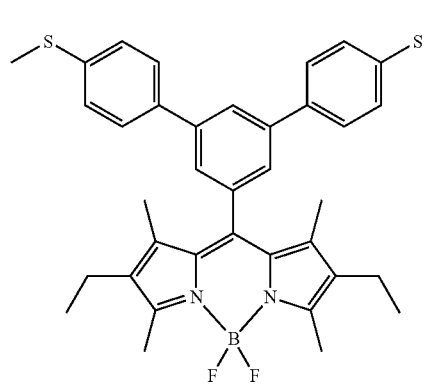 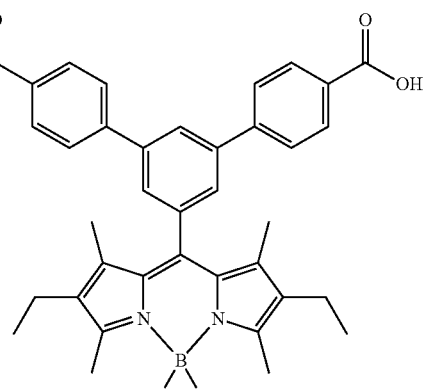
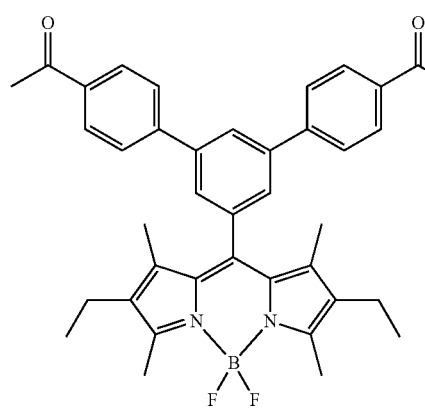 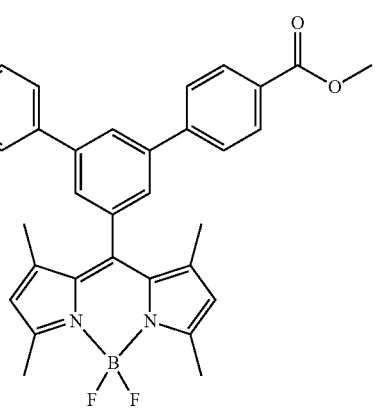
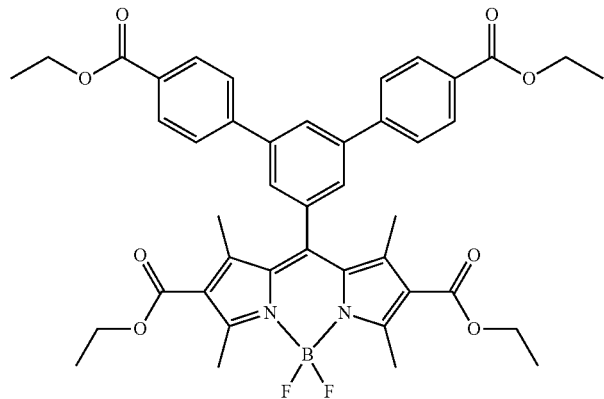 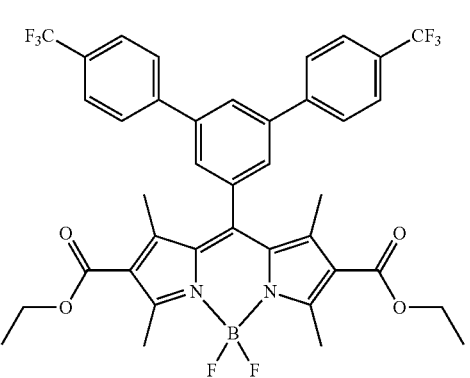

-continued
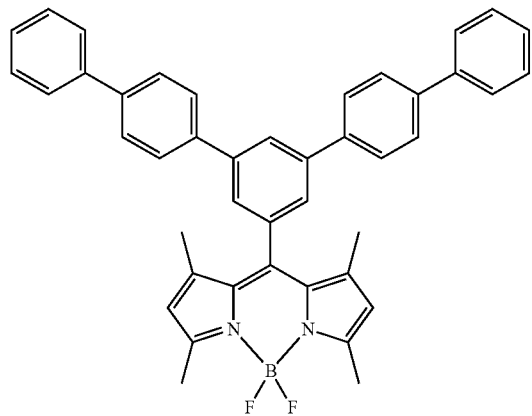
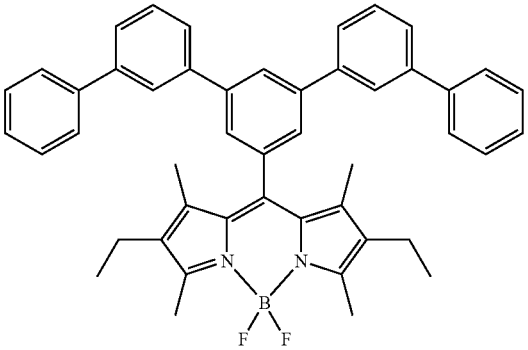
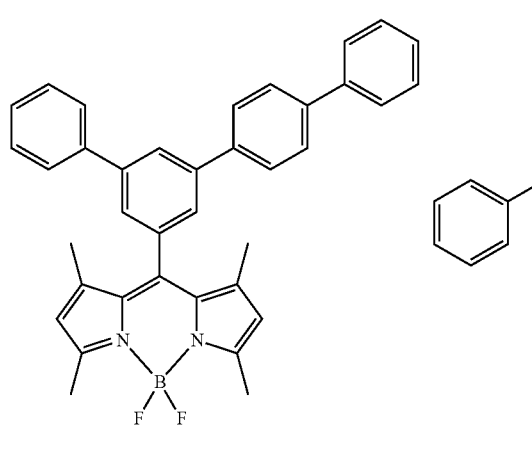
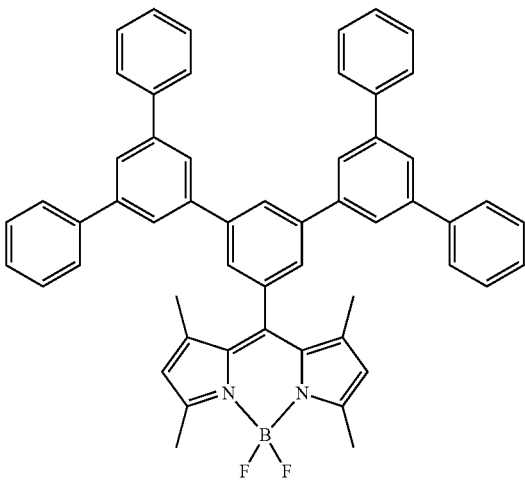
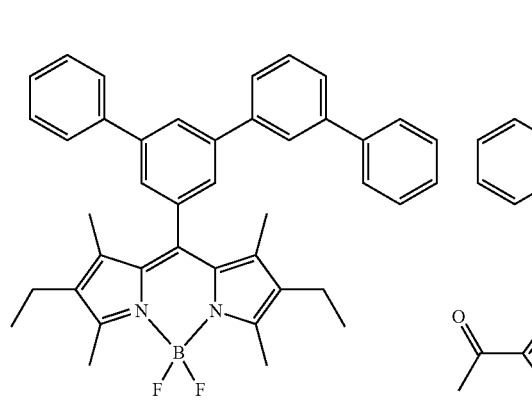
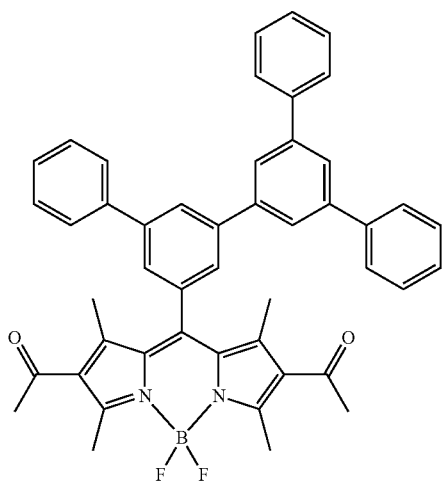

-continued
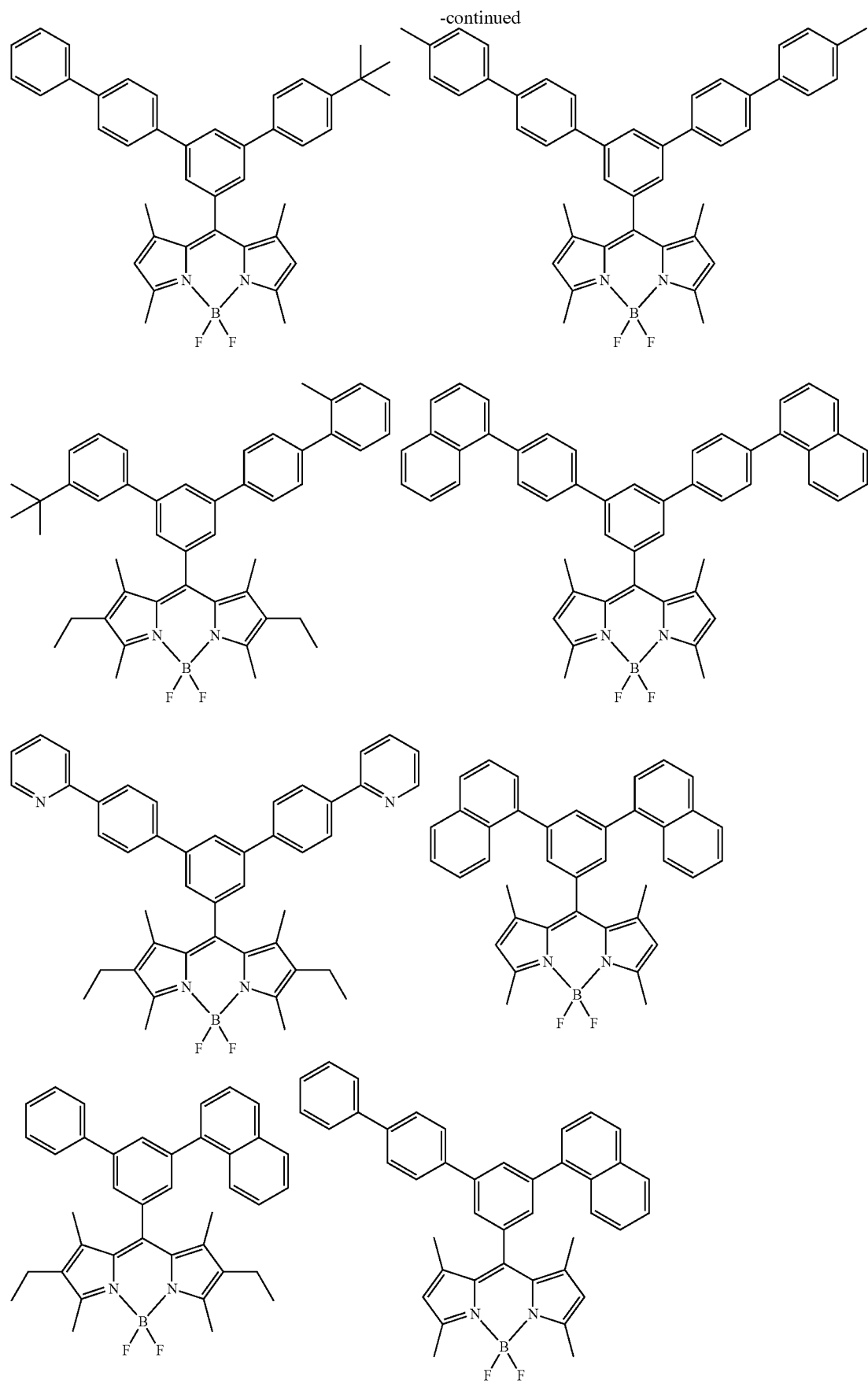

-continued
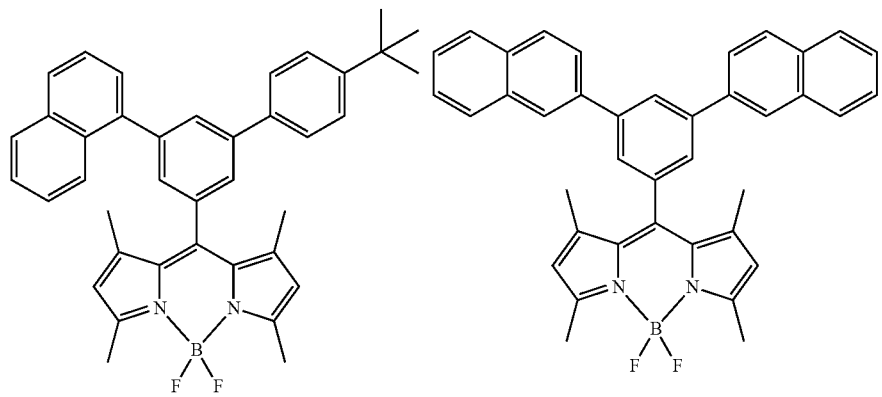
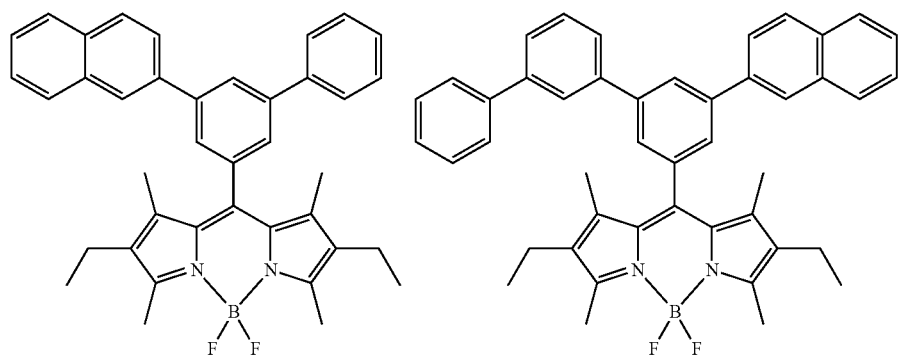
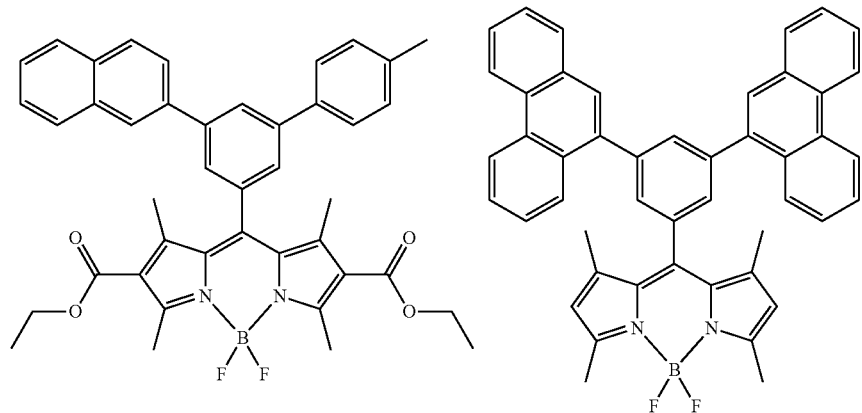
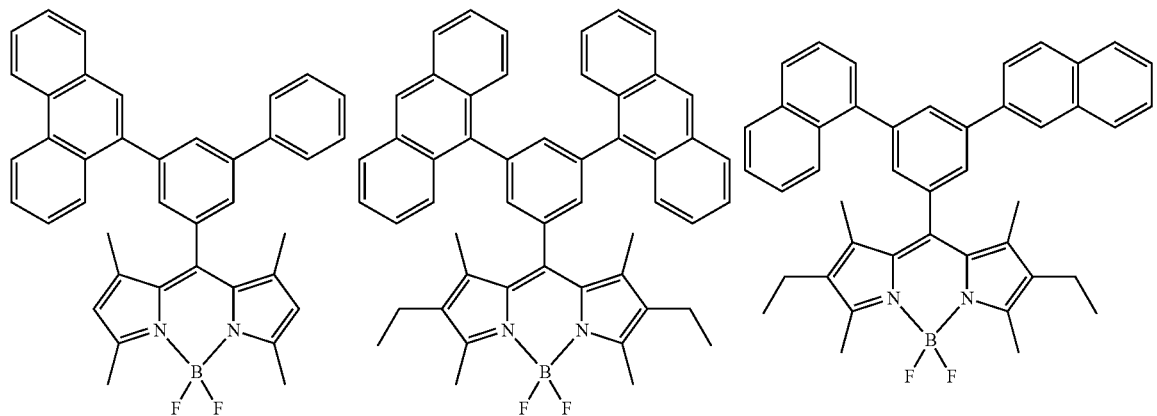

-continued
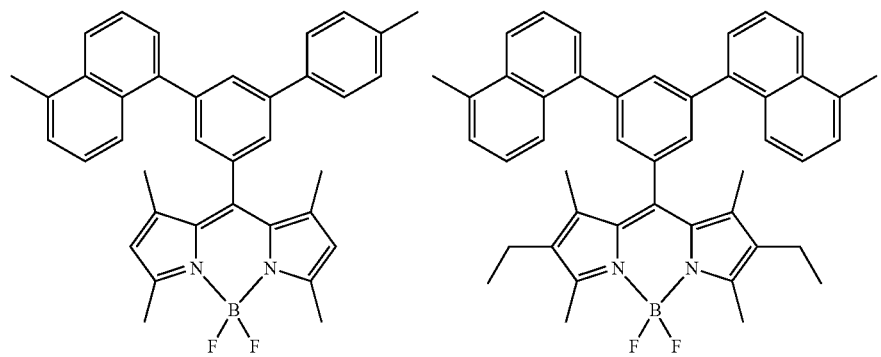
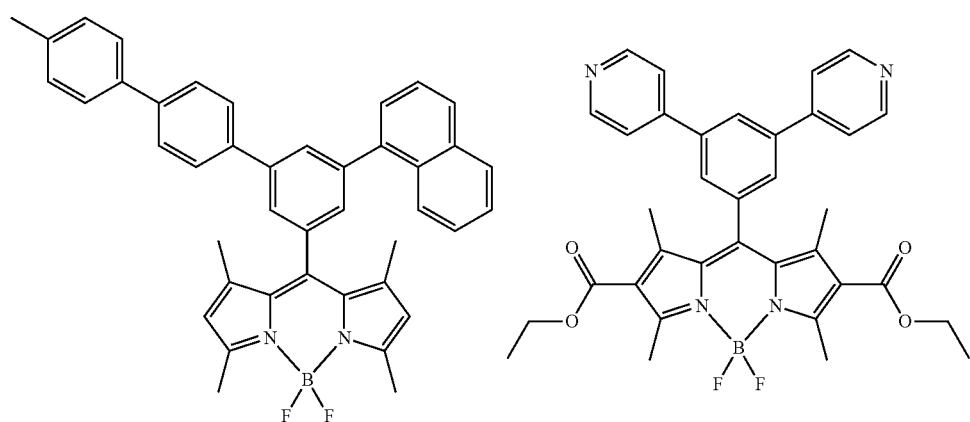
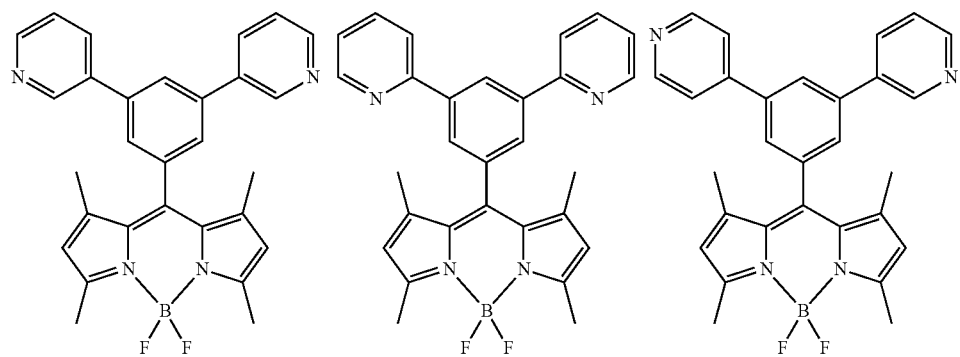
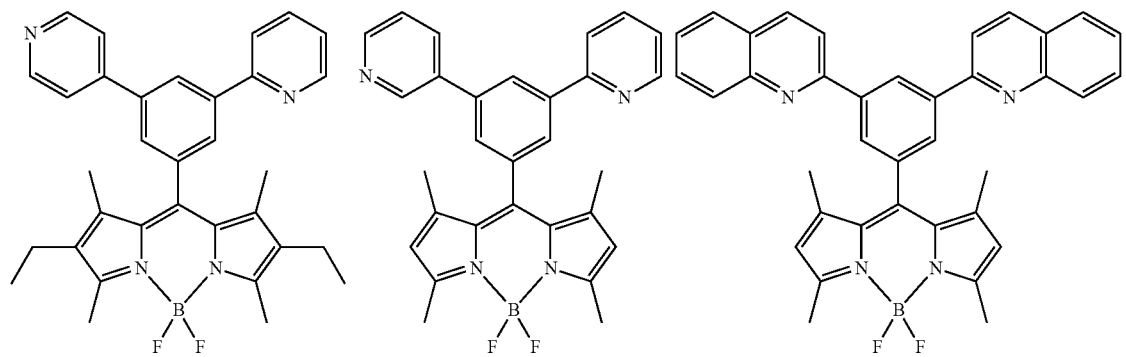

55 56
-continued
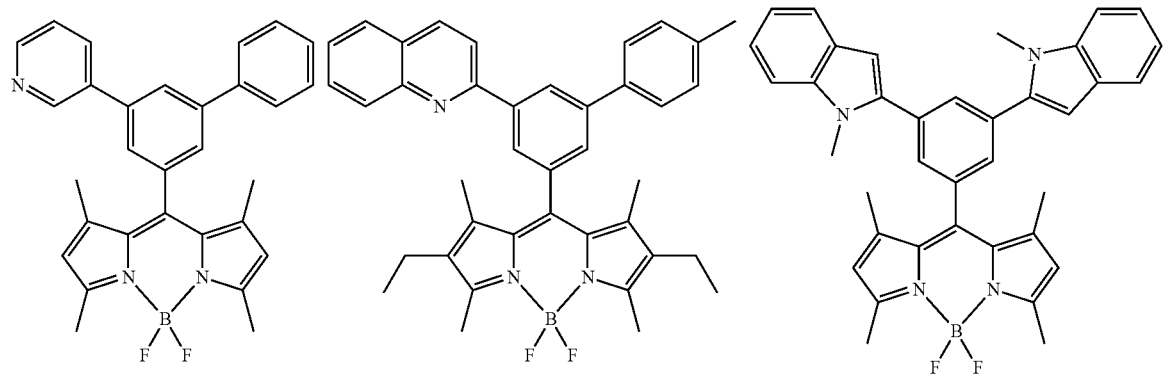
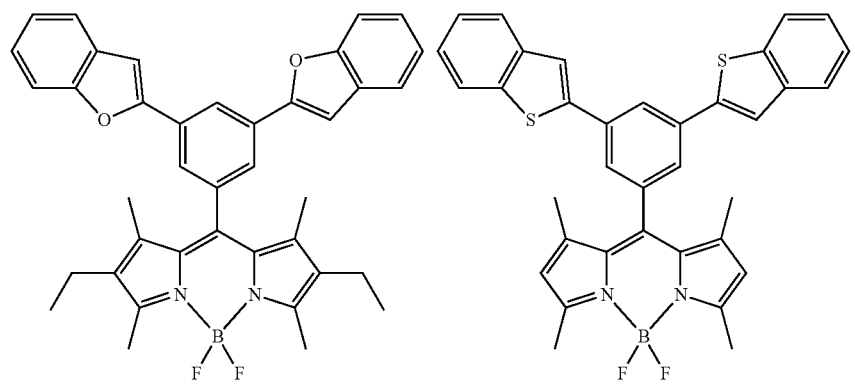
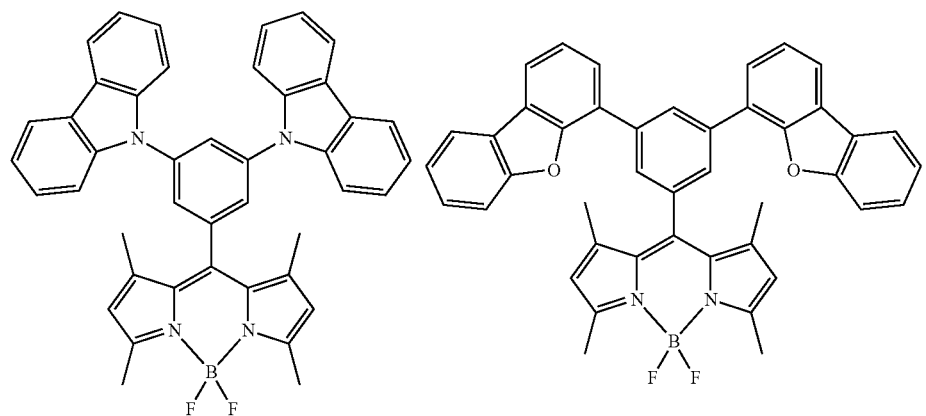
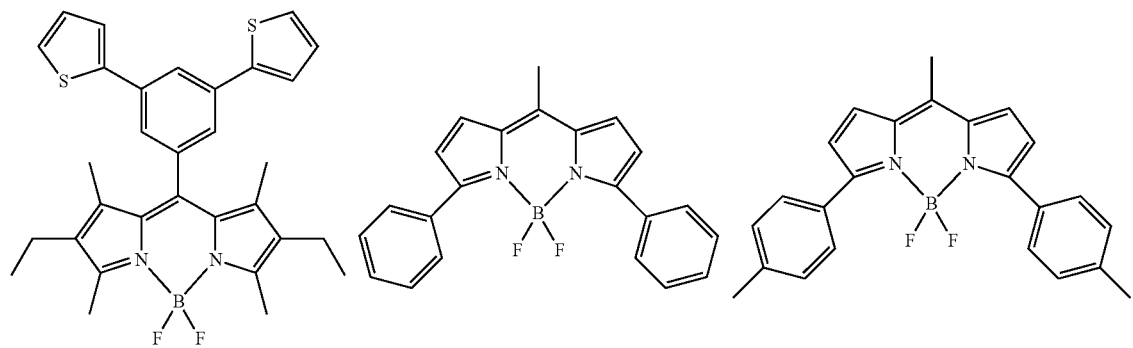

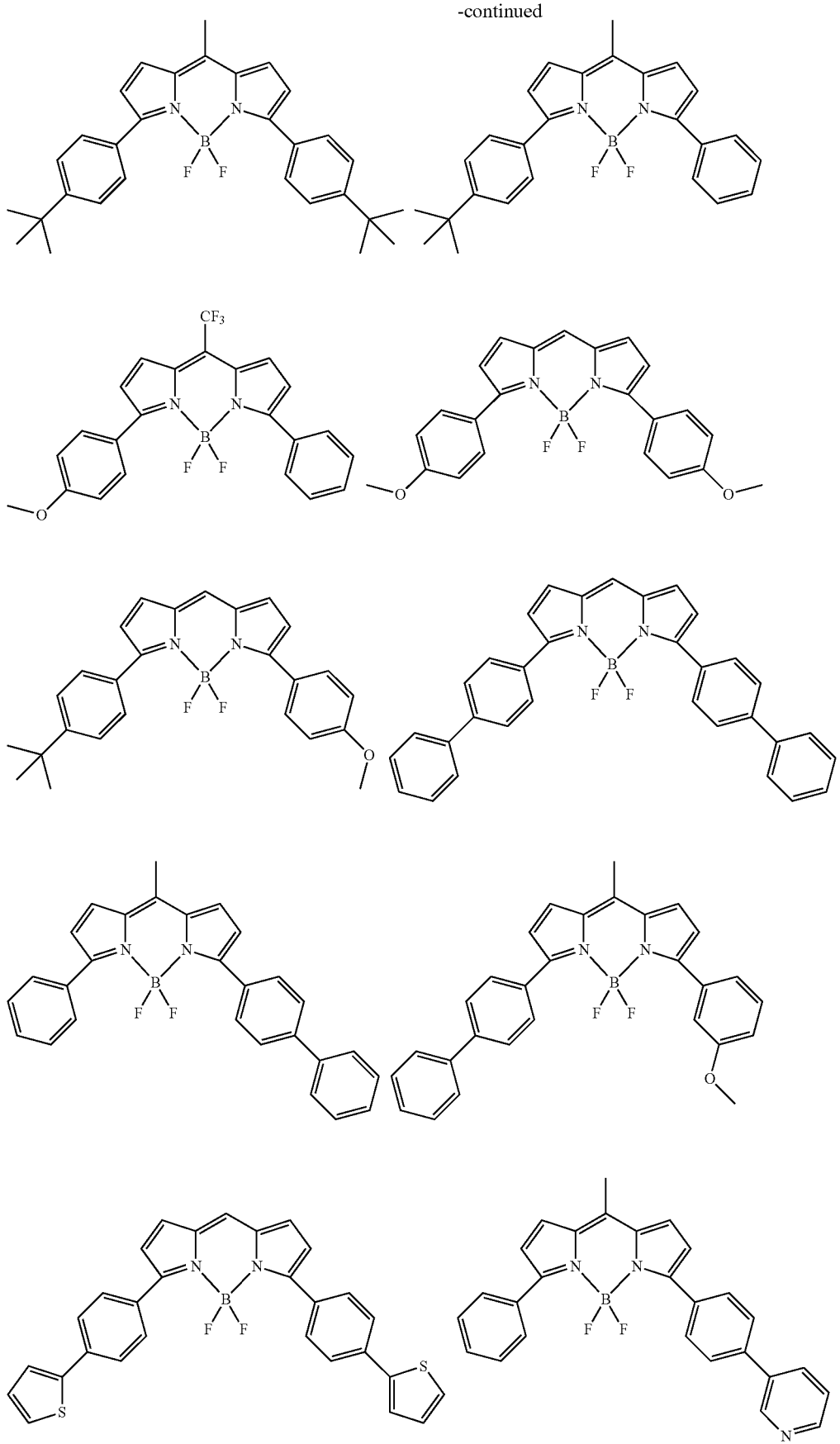

-continued
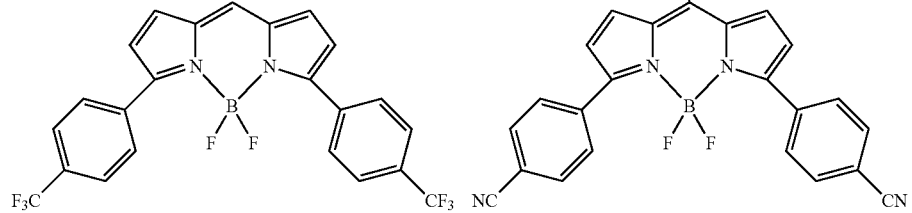
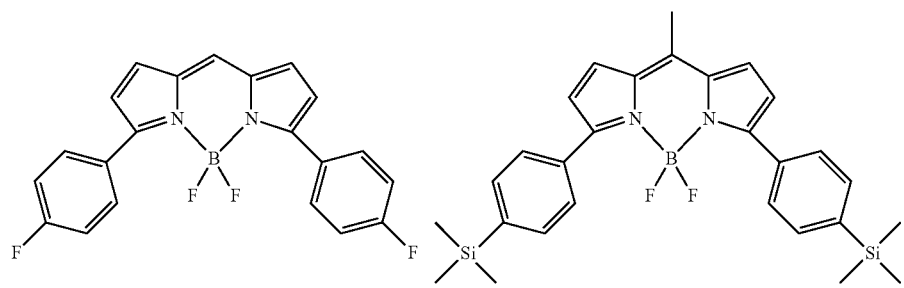
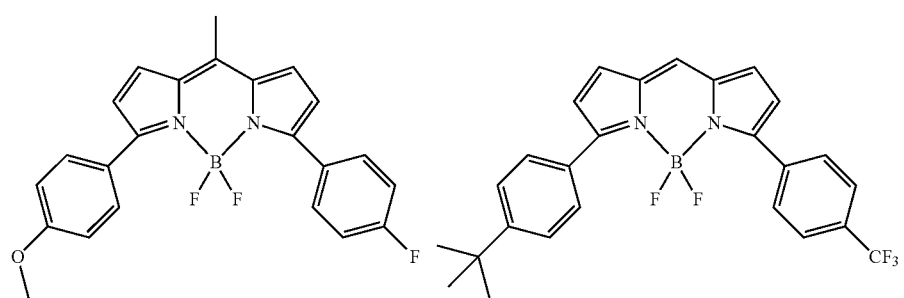
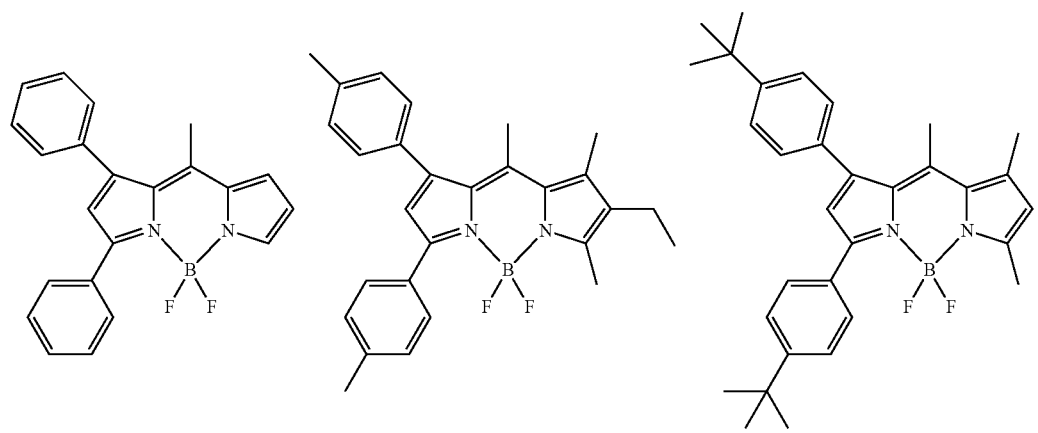
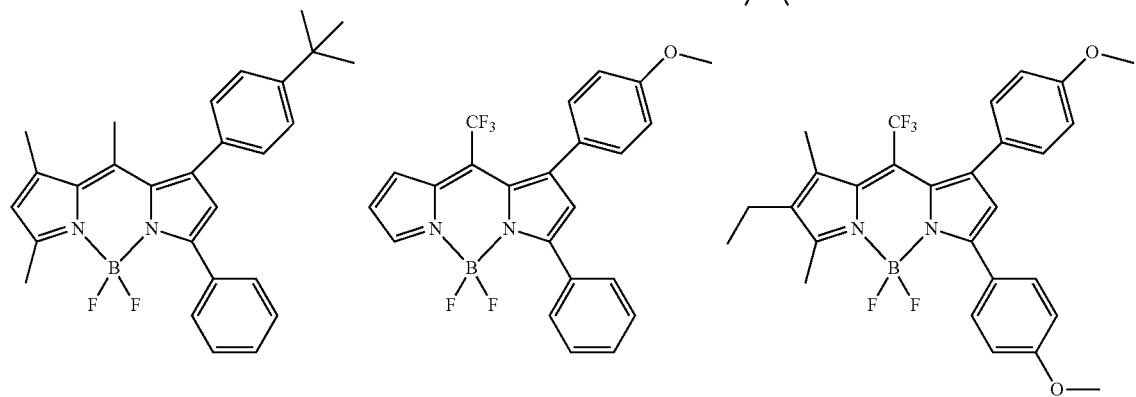

-continued
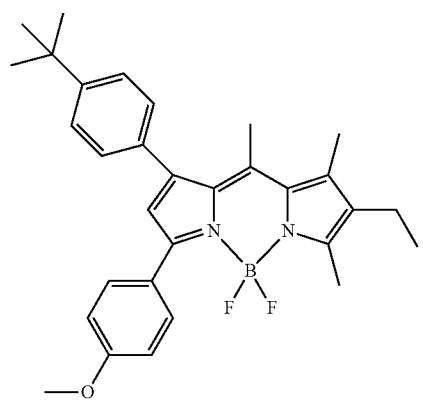
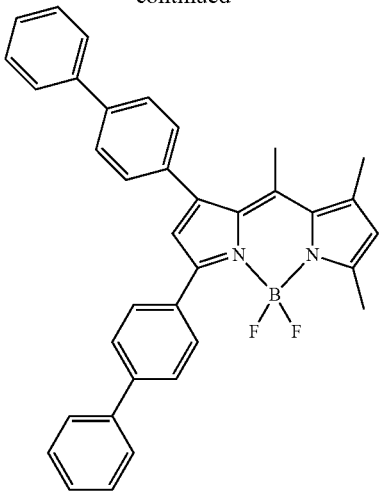
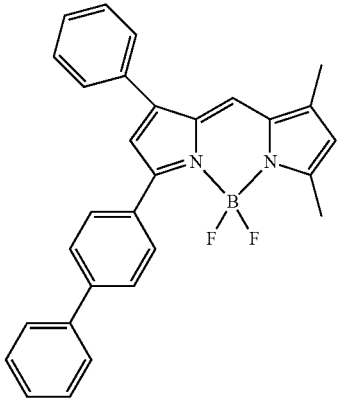
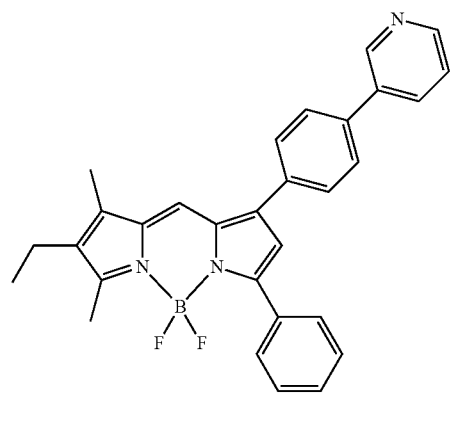
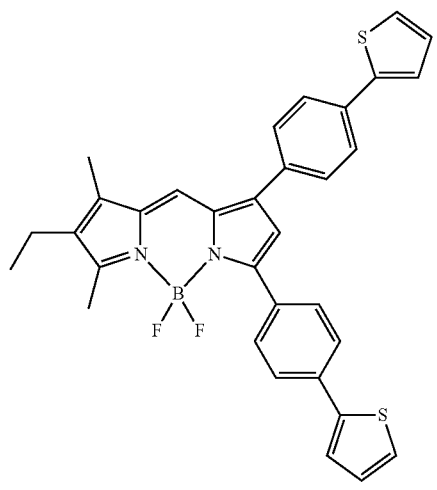
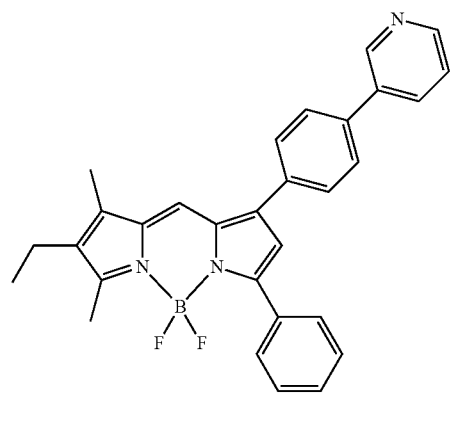
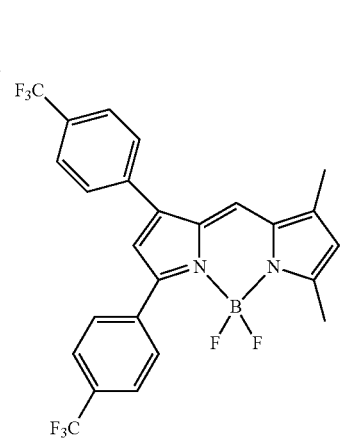
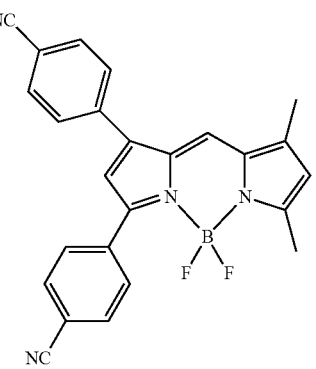

-continued
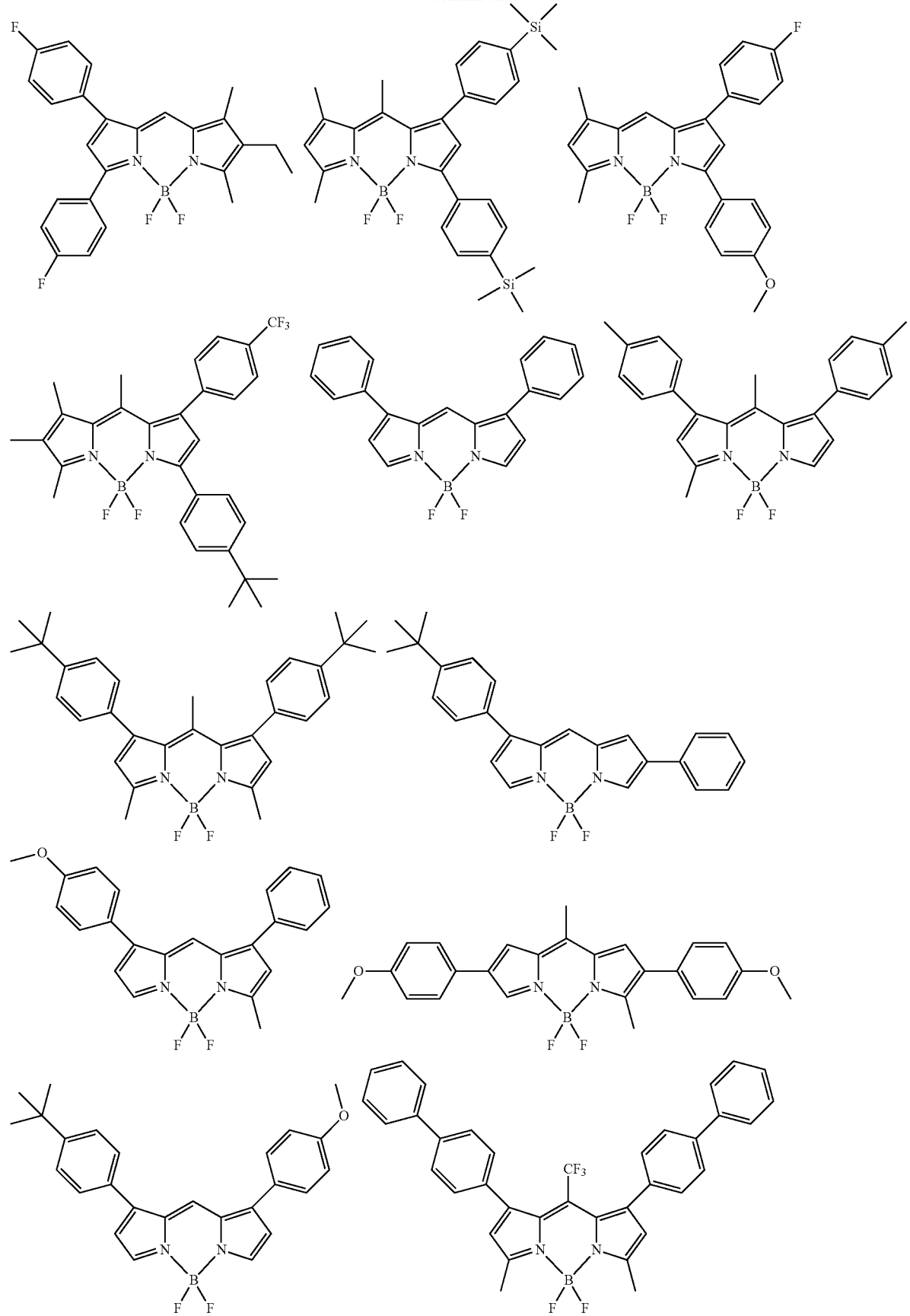

-continued
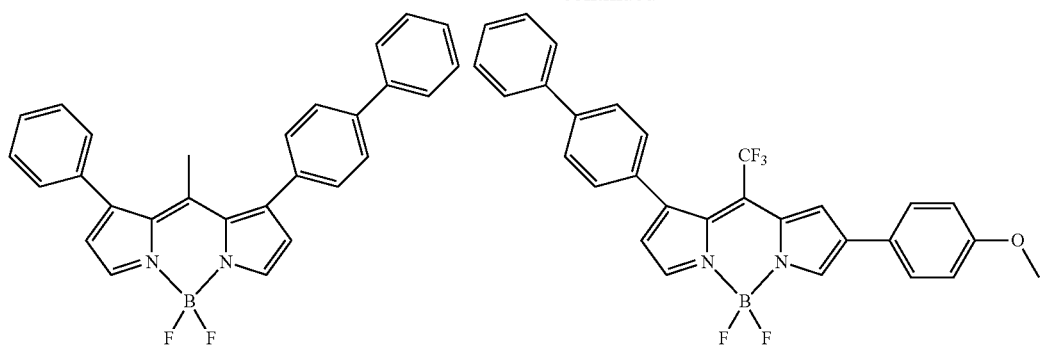
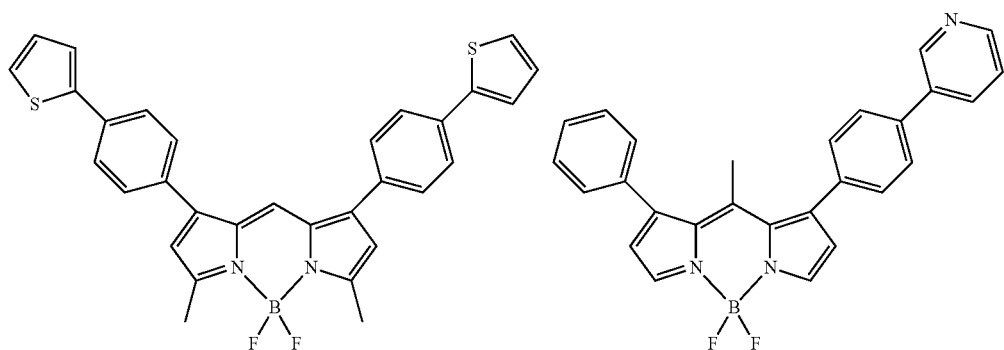
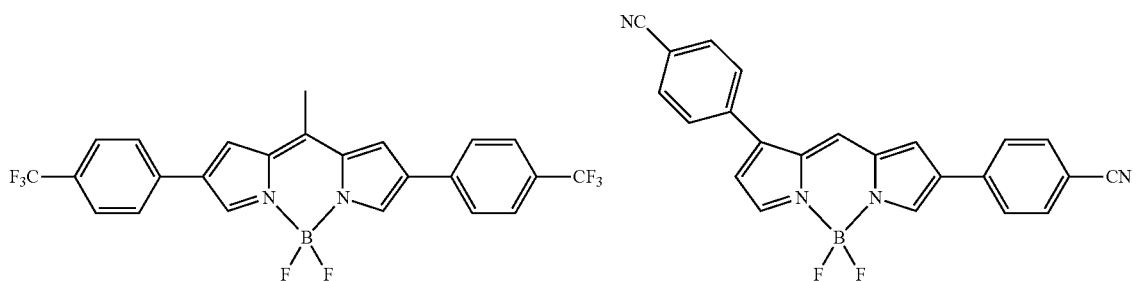
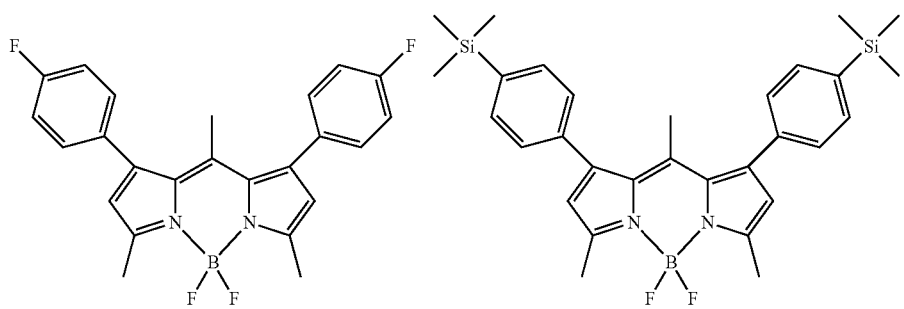
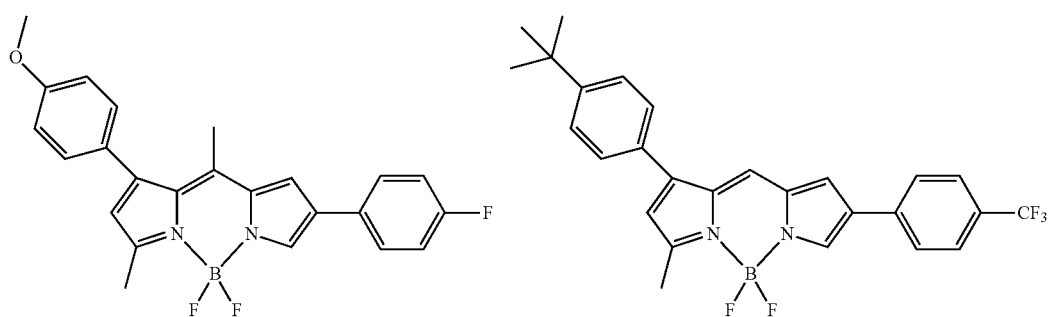

-continued
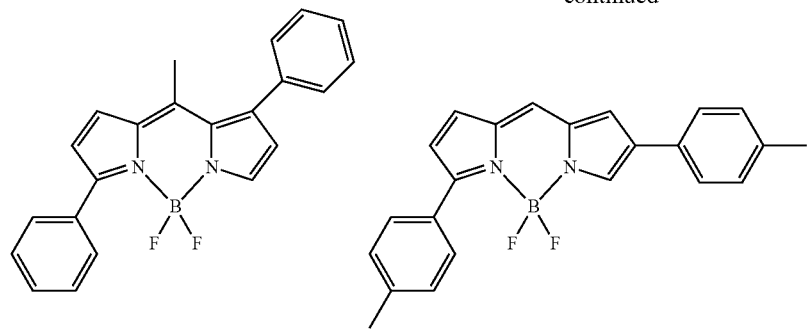
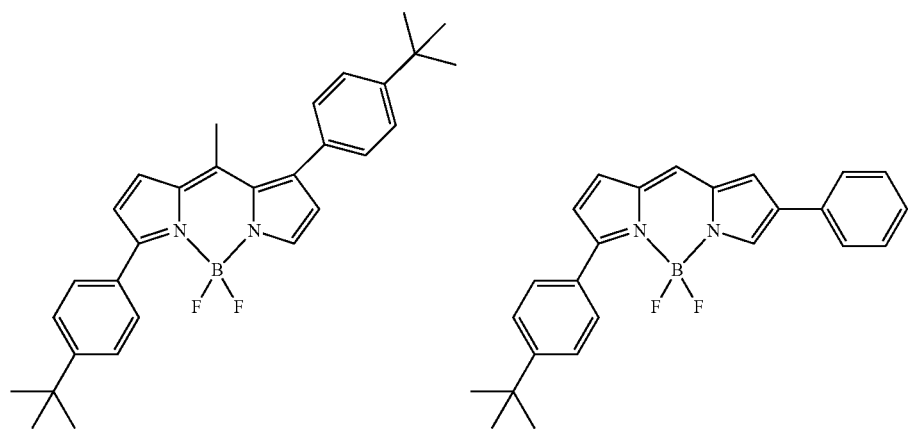
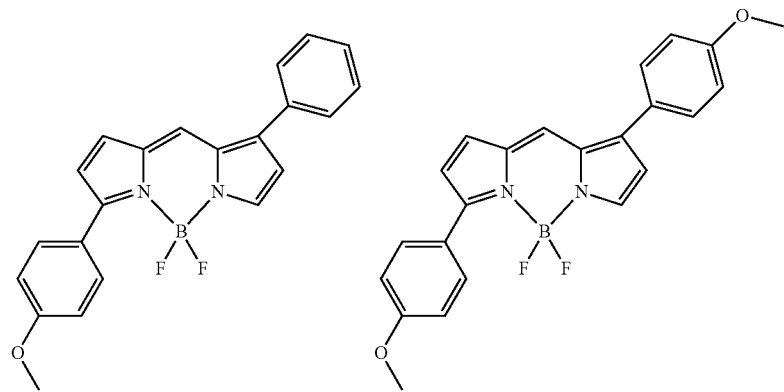
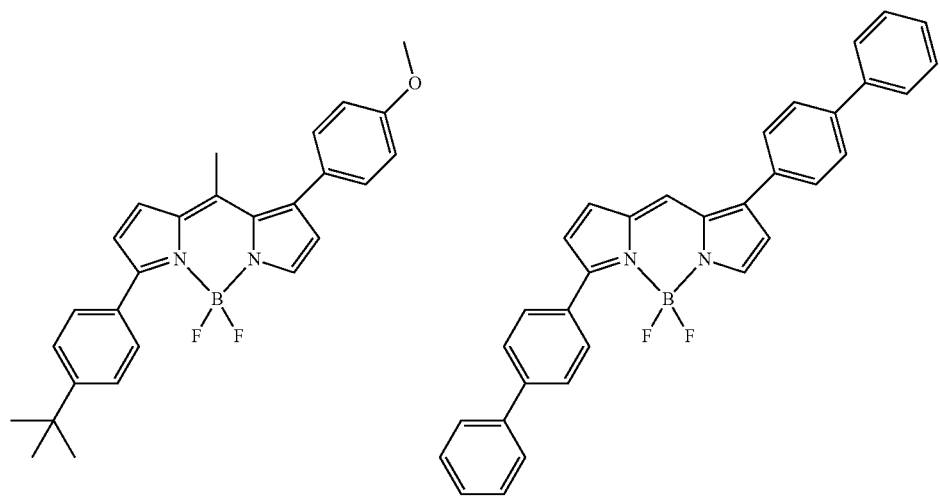

-continued
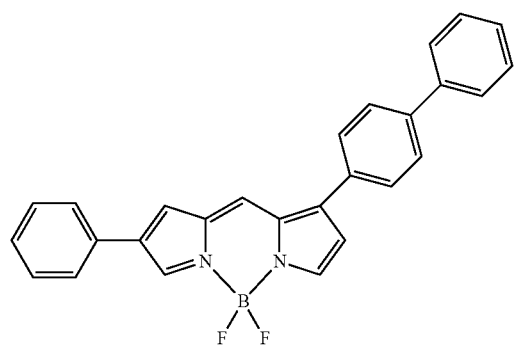
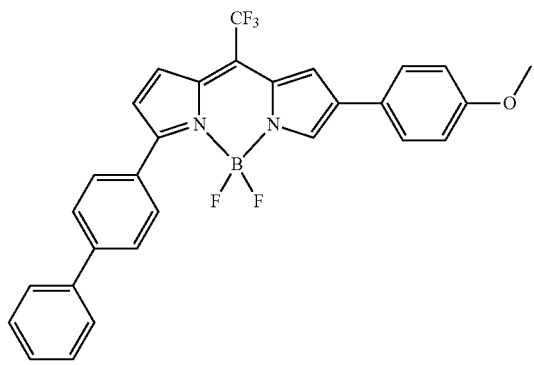
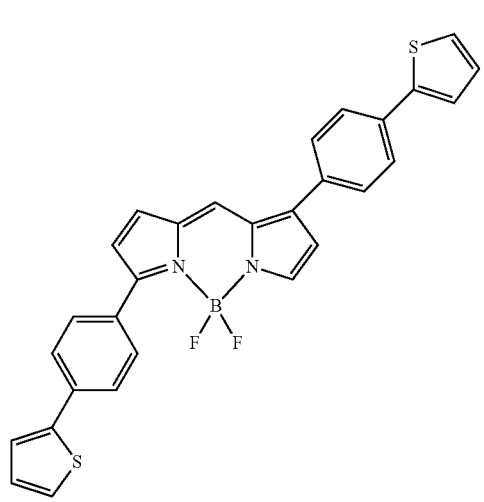
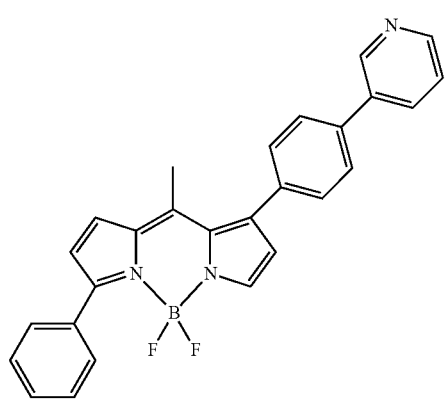
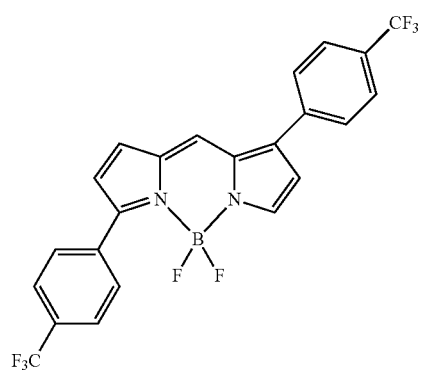
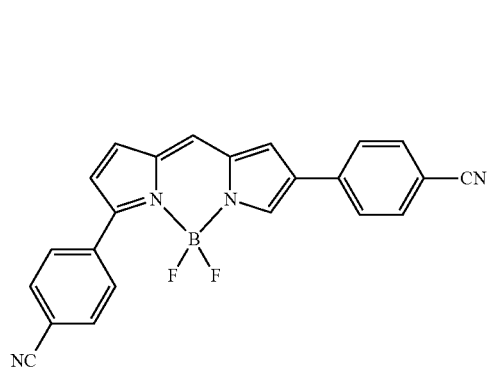

-continued
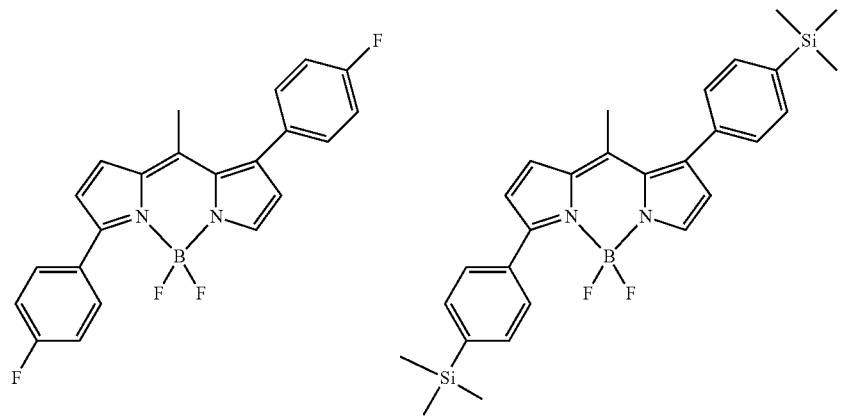
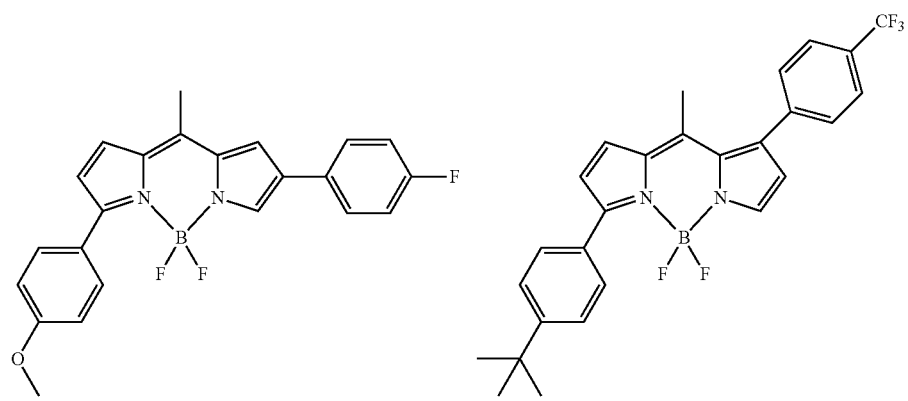
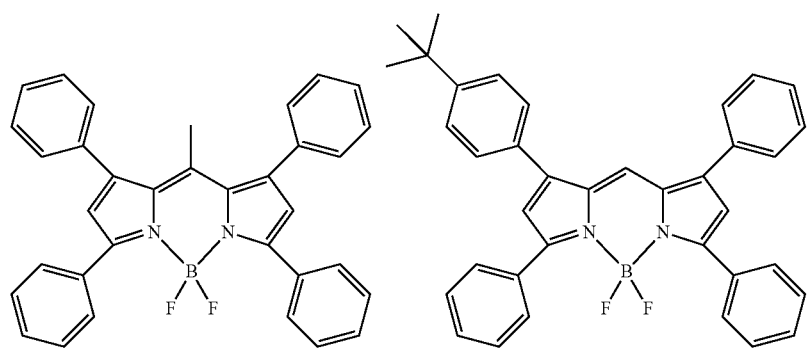
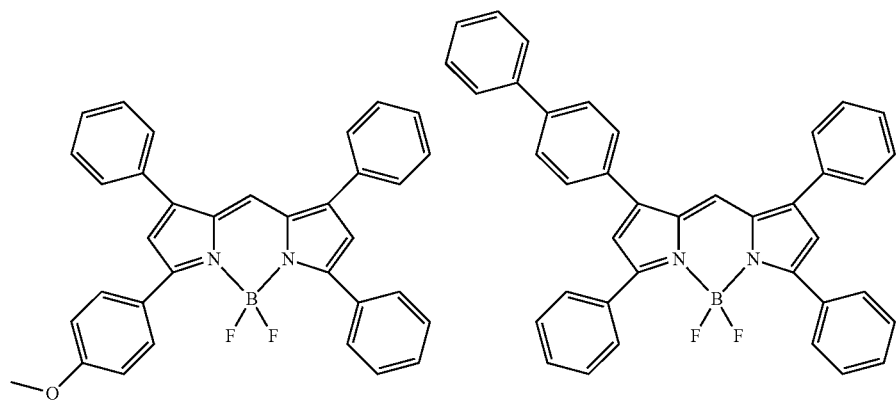

-continued
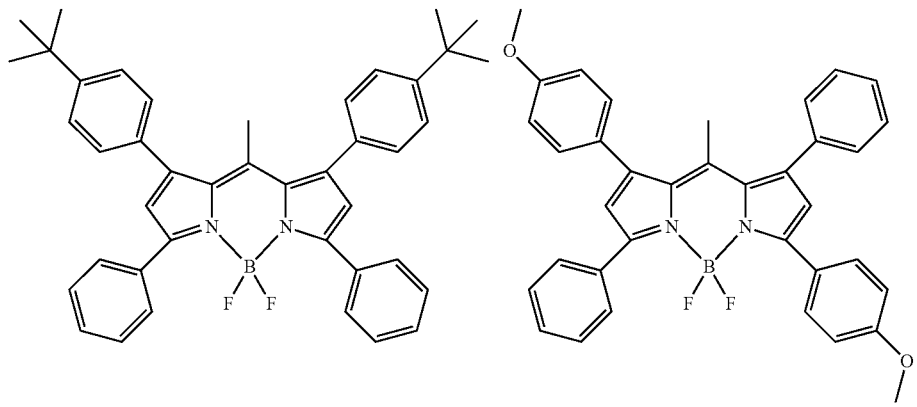
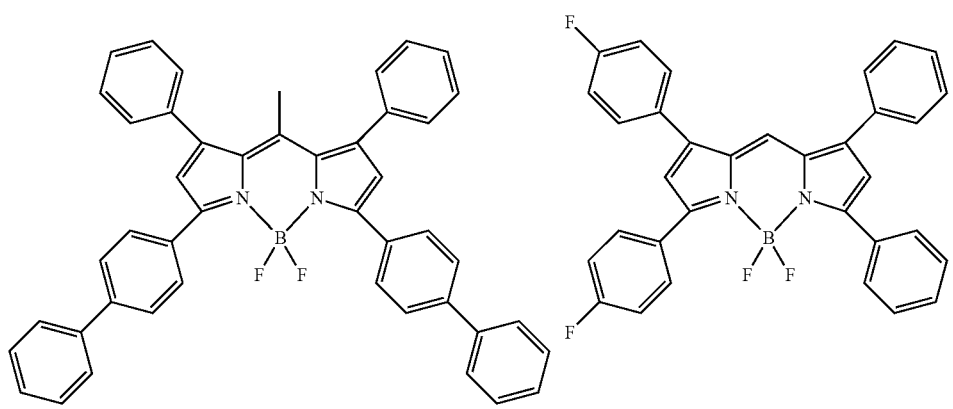
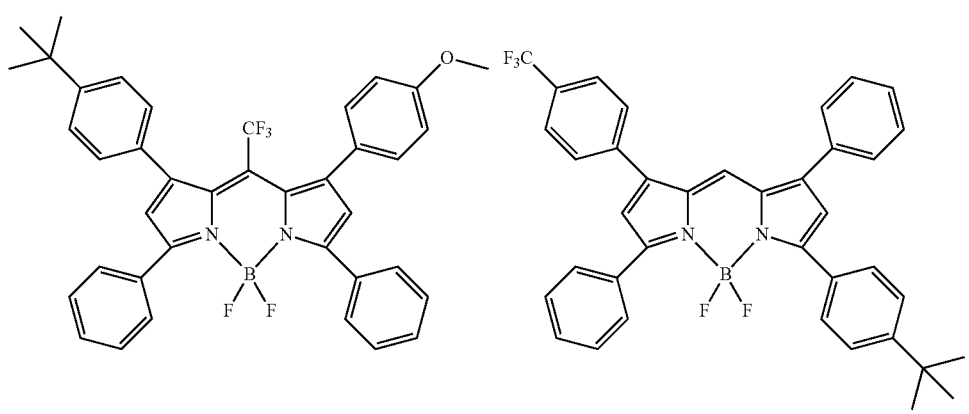
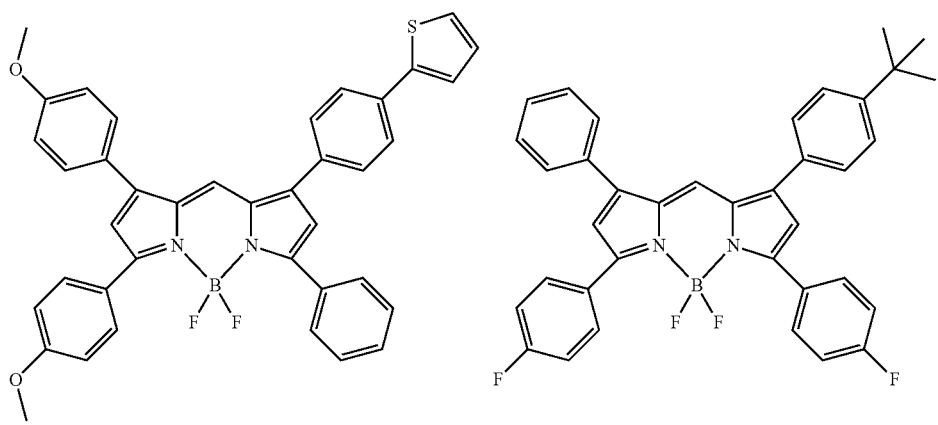

-continued
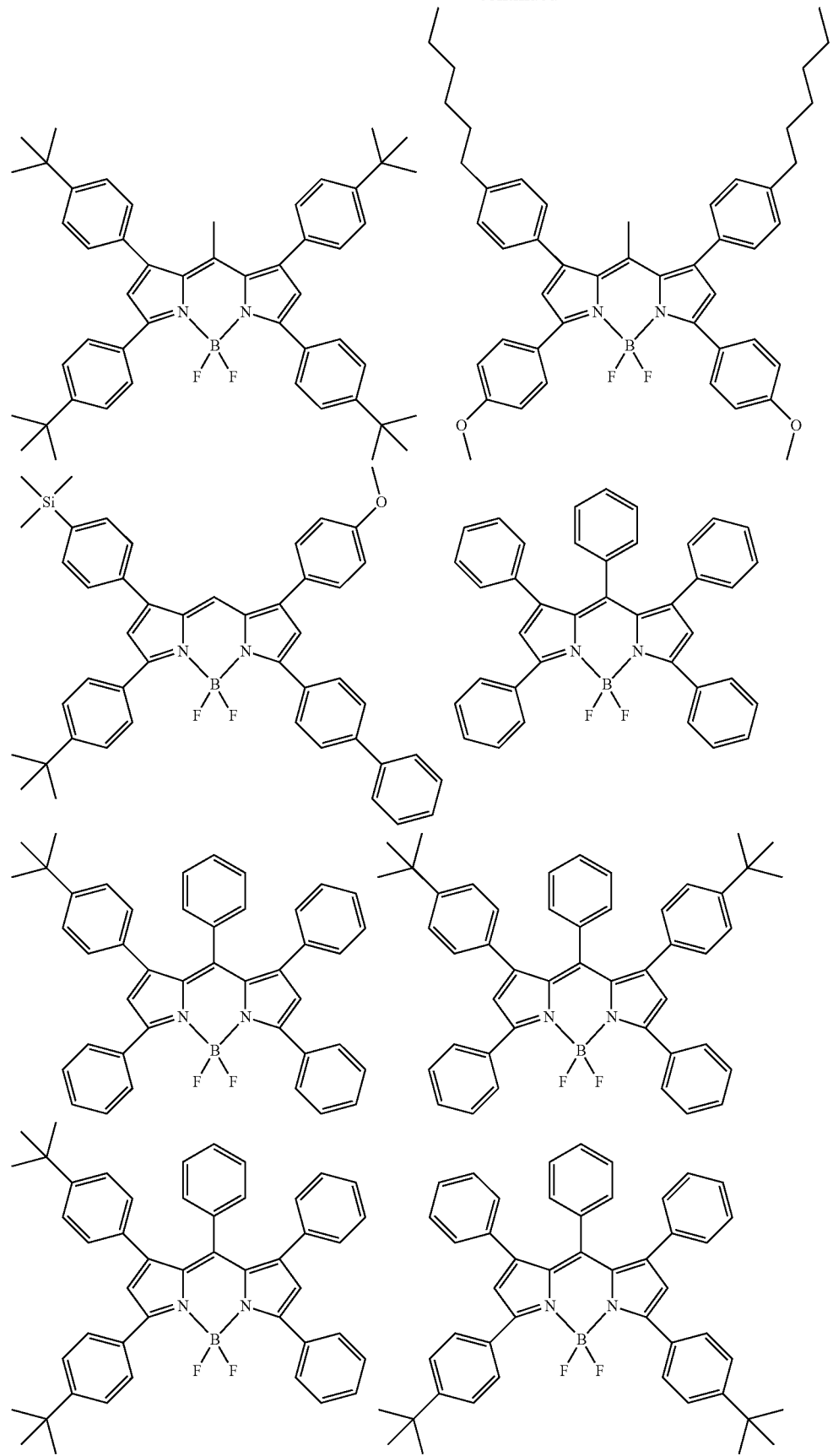

-continued
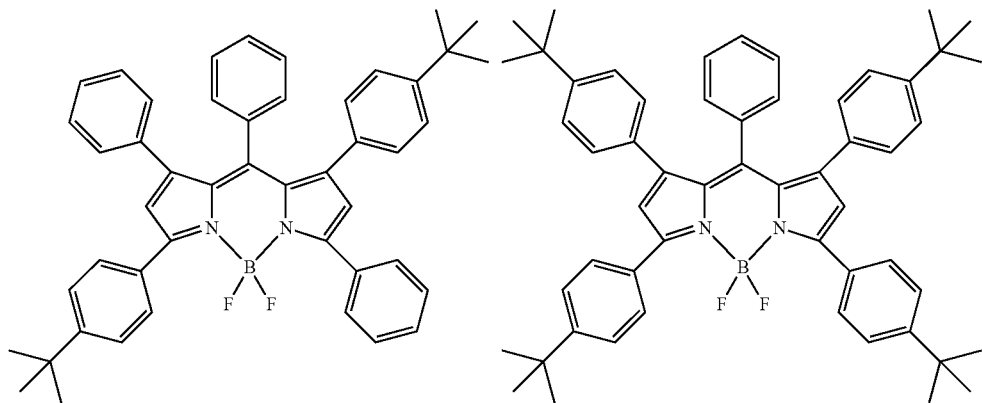
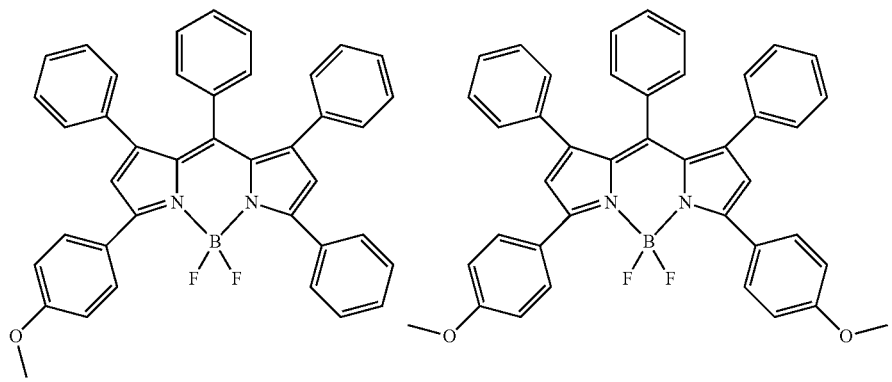
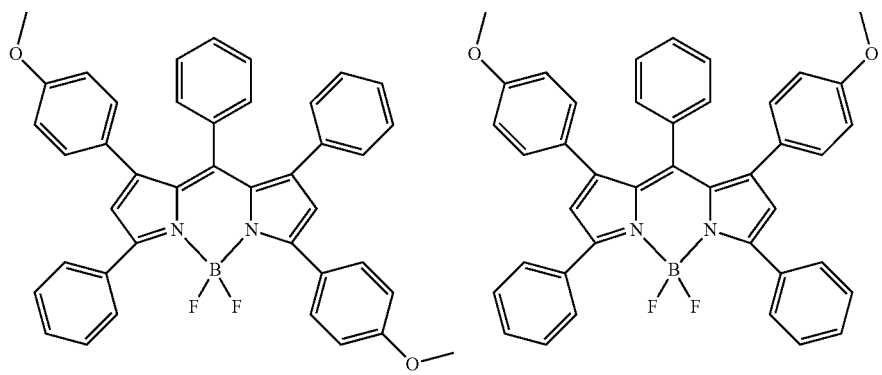
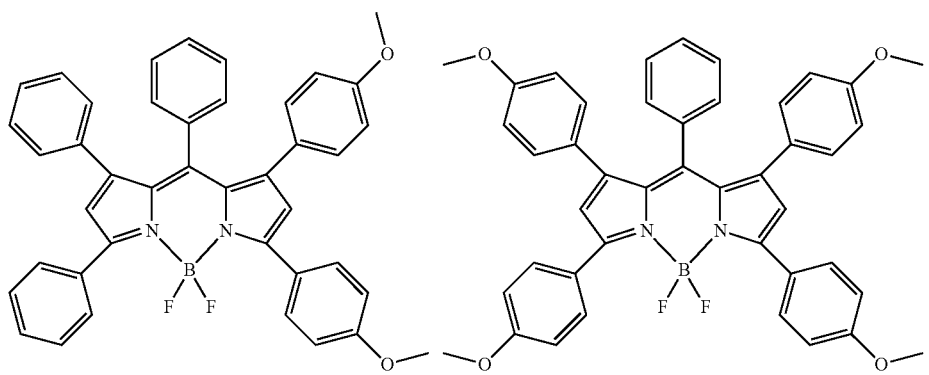

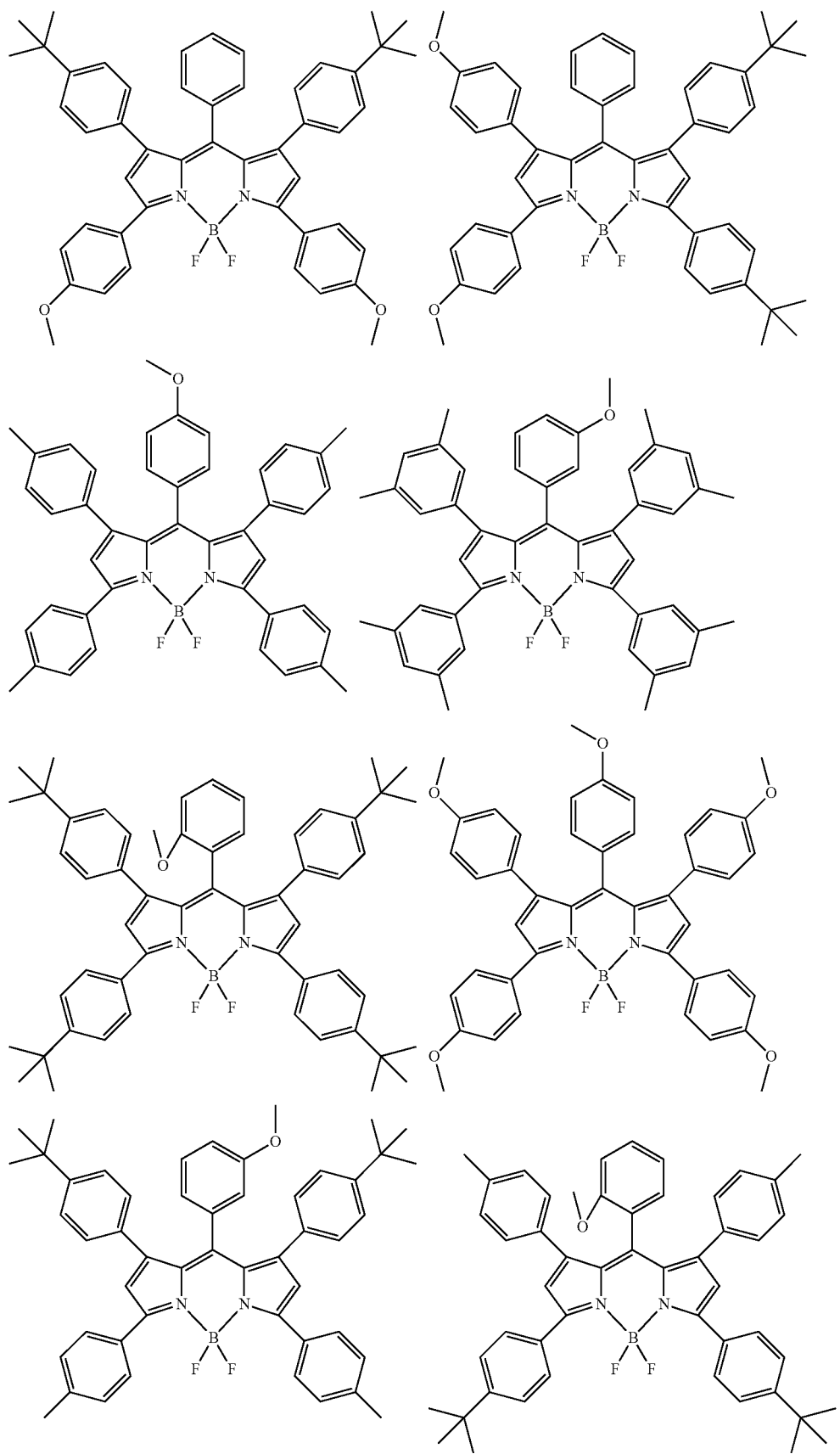

-continued
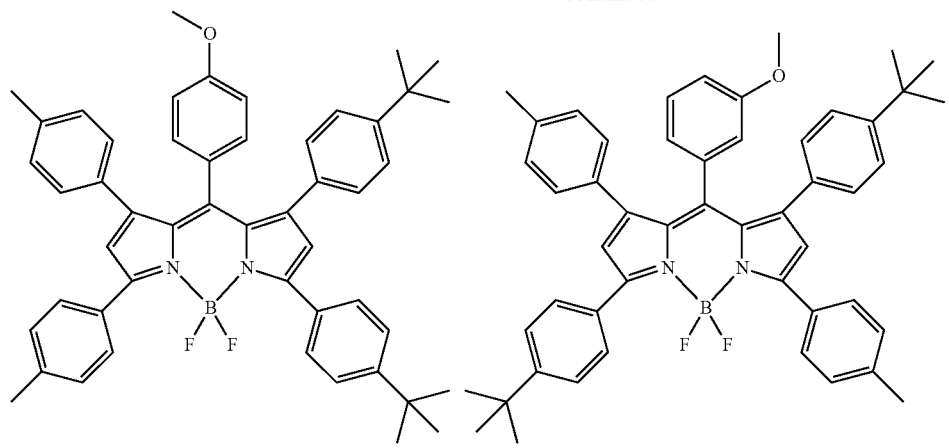
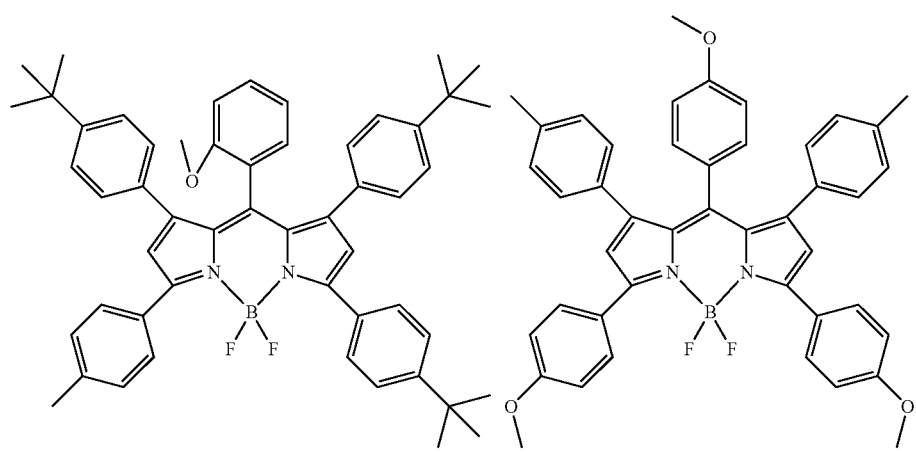
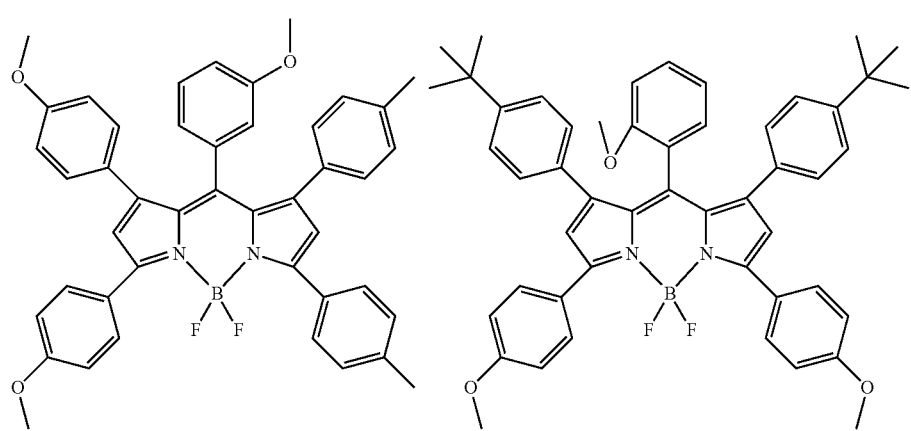

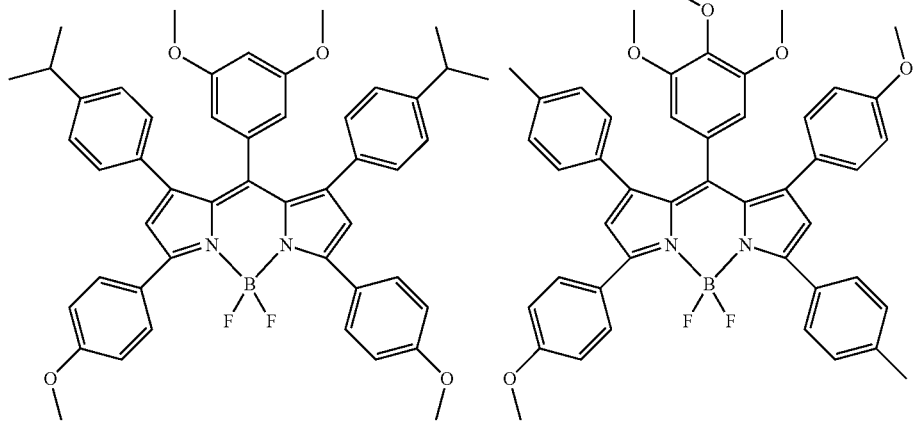
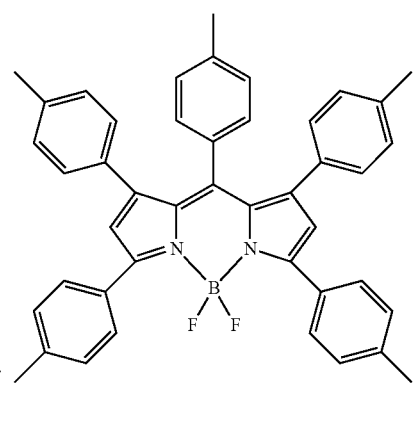
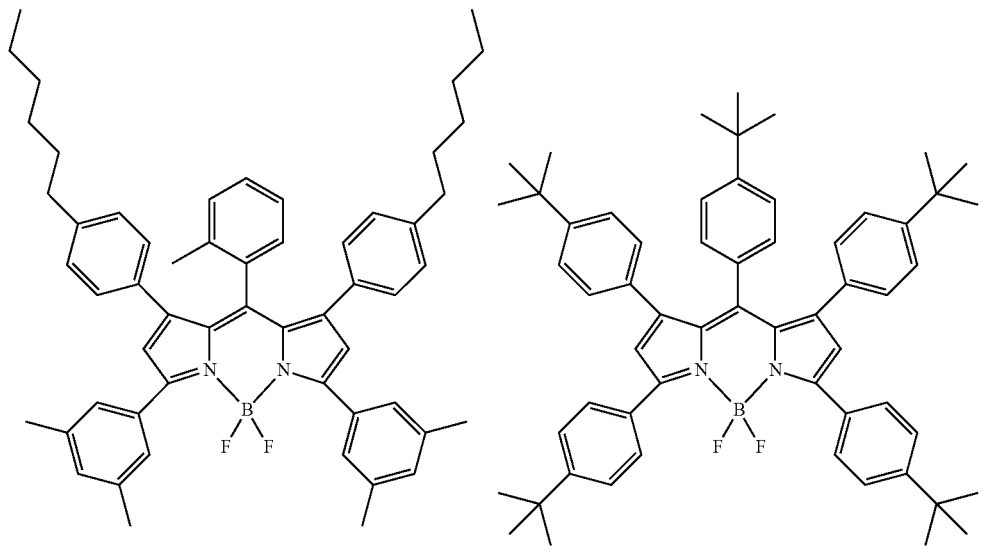

-continued
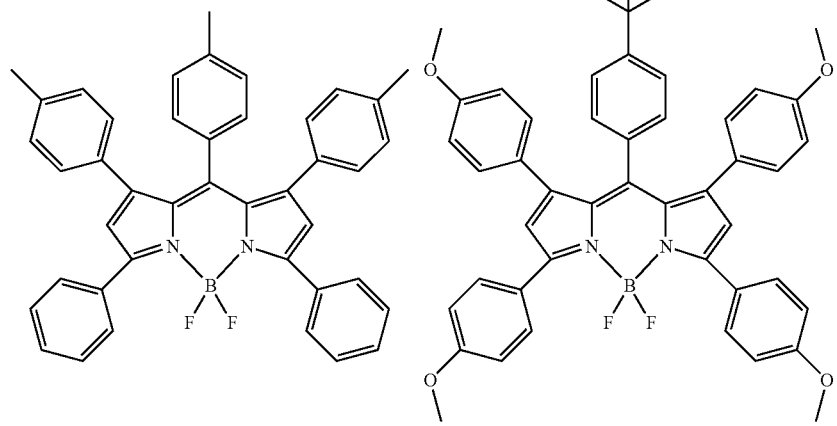
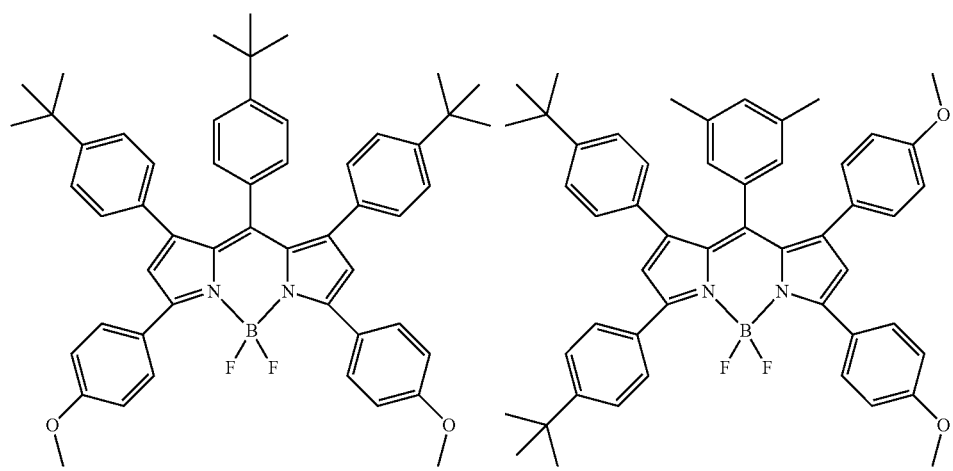
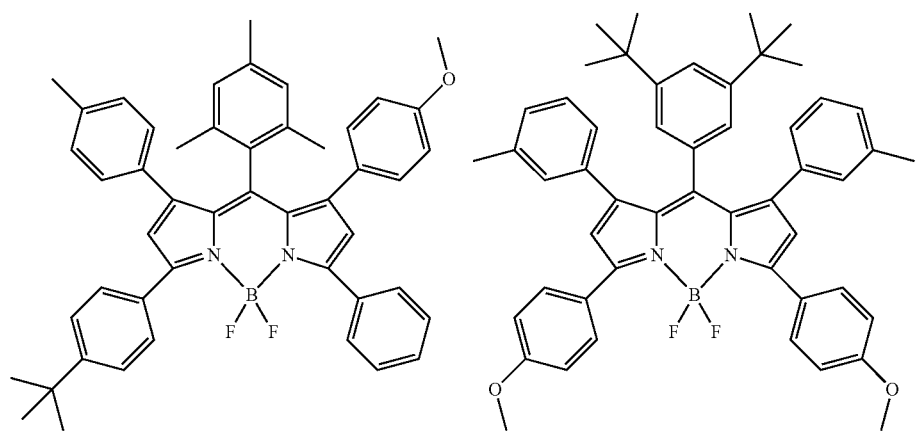

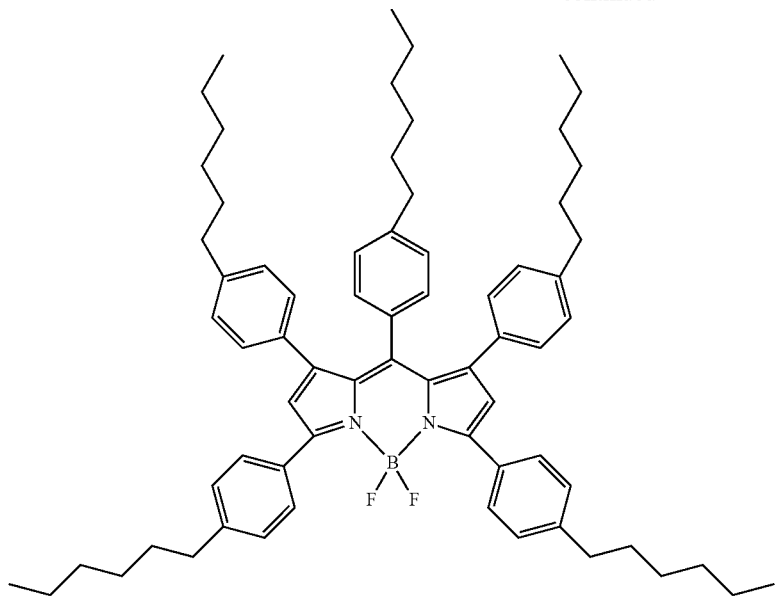
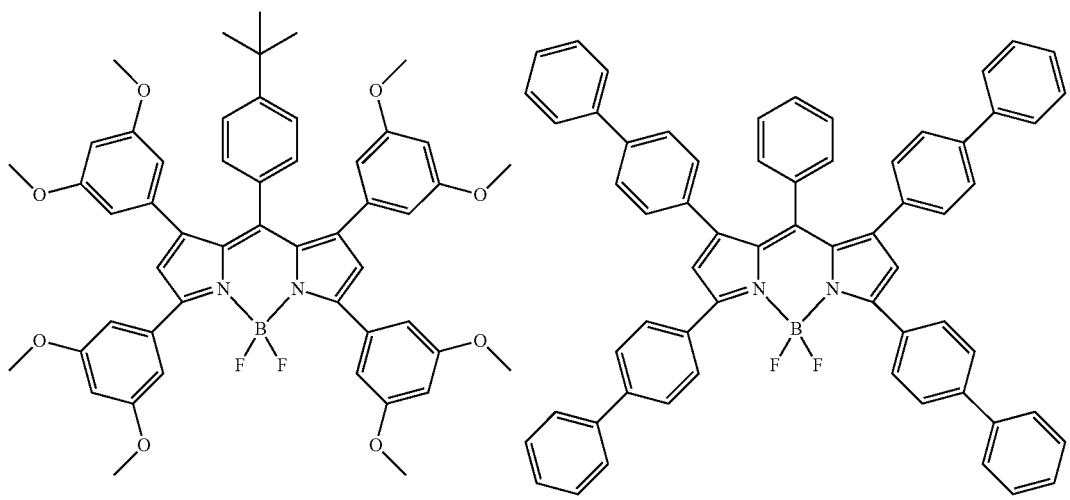
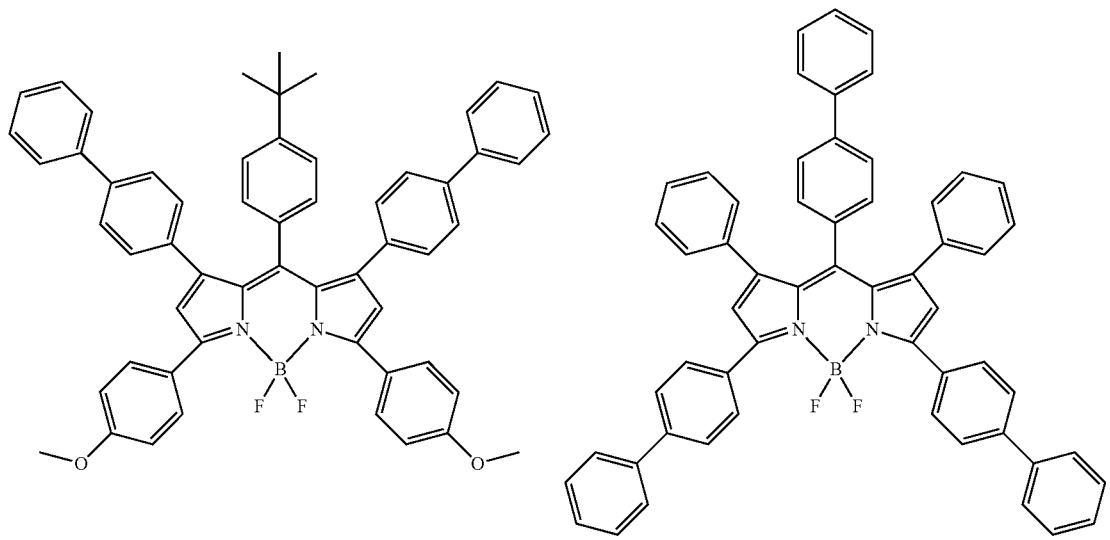

89
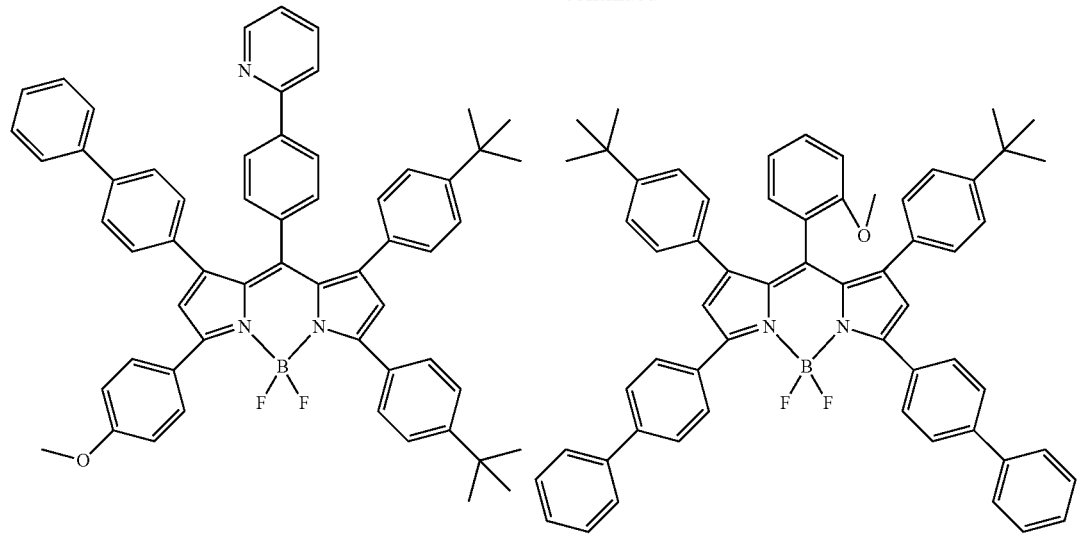
90
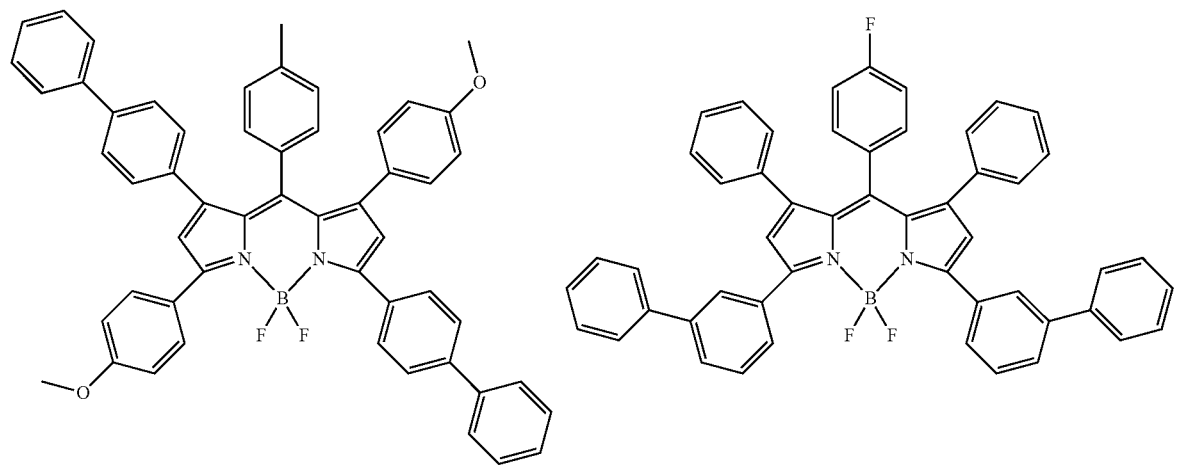
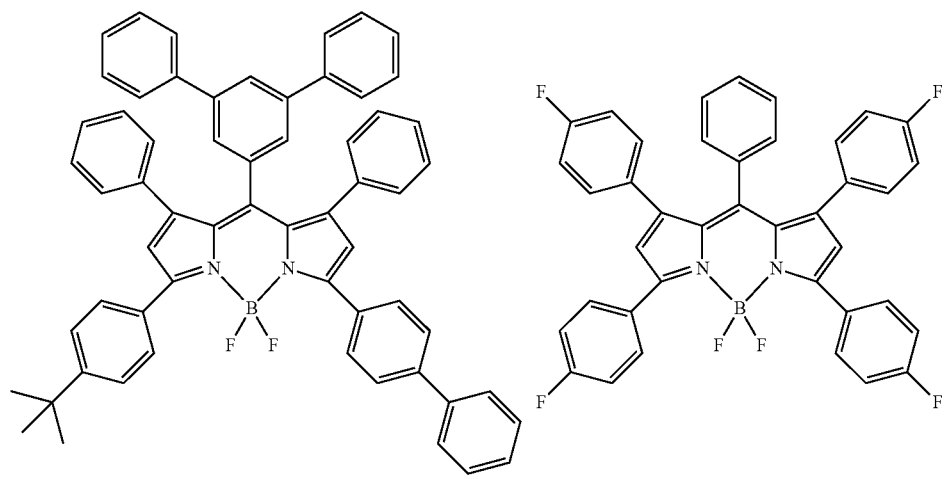

-continued
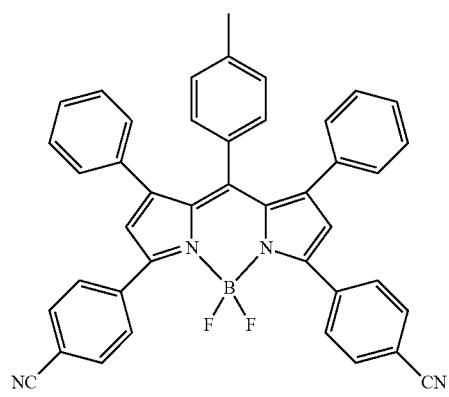
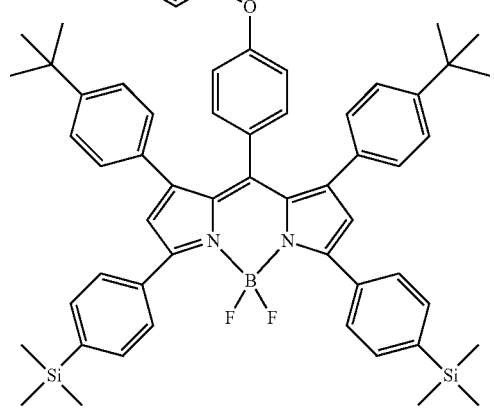
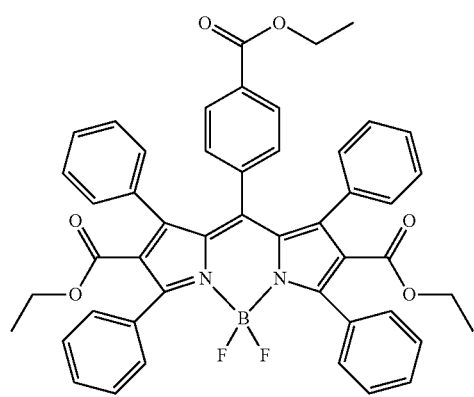
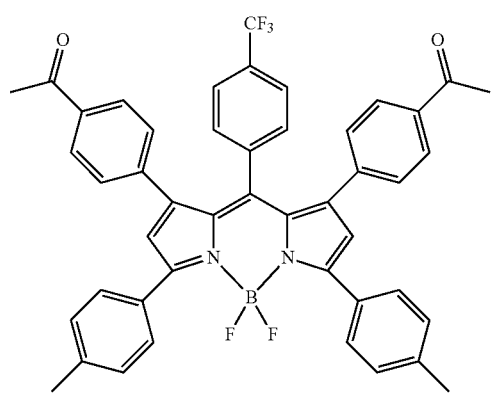
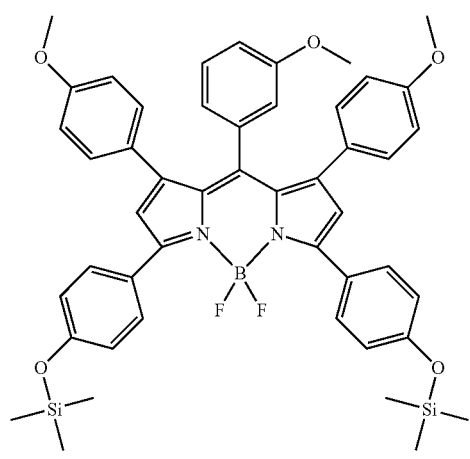
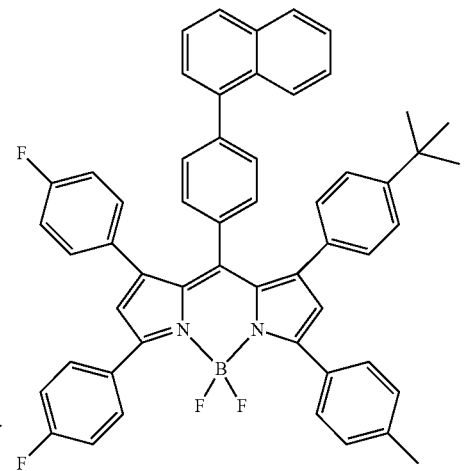

-continued
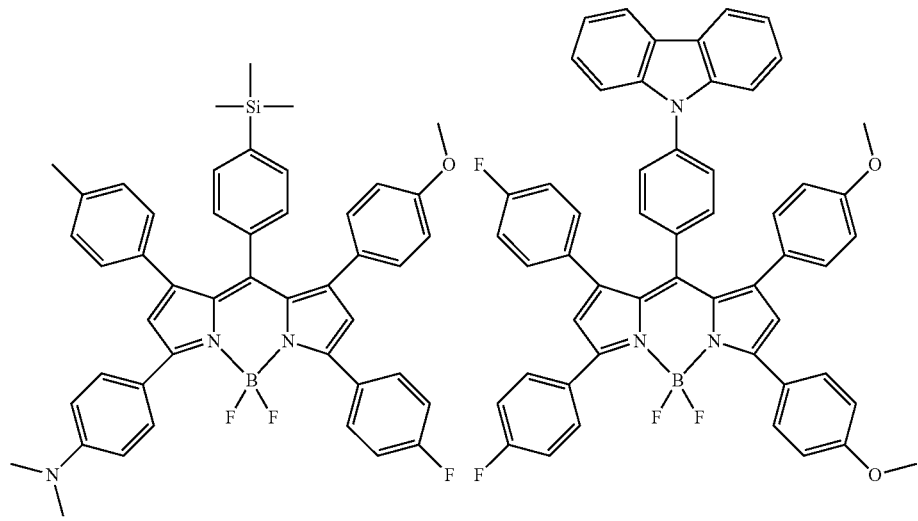
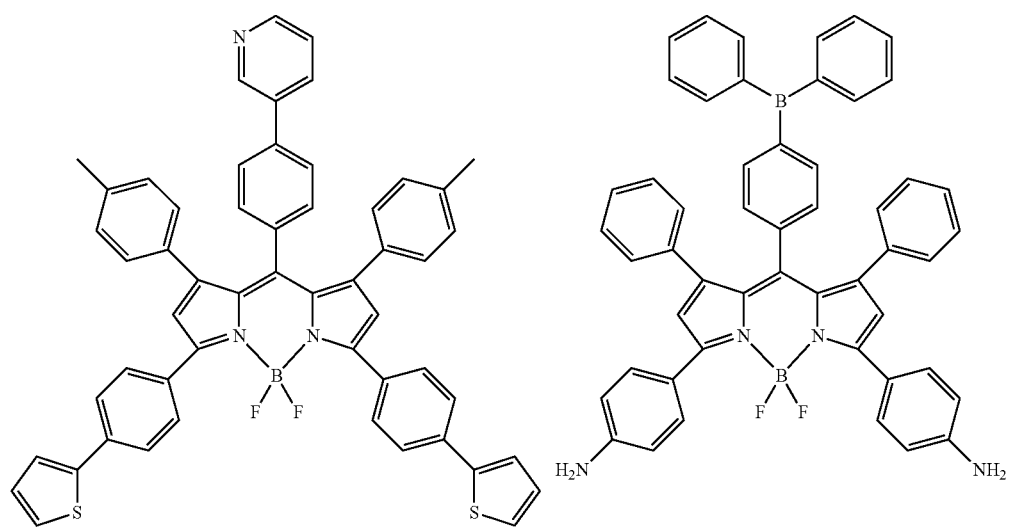
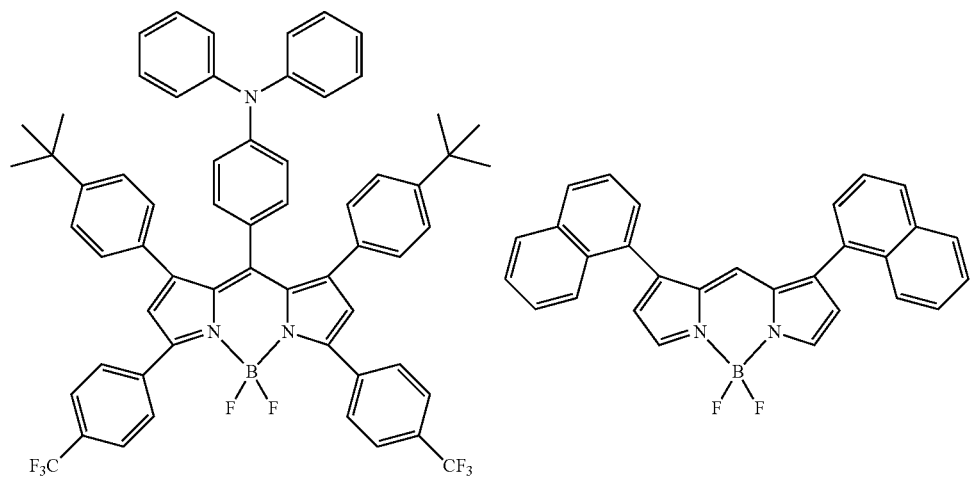

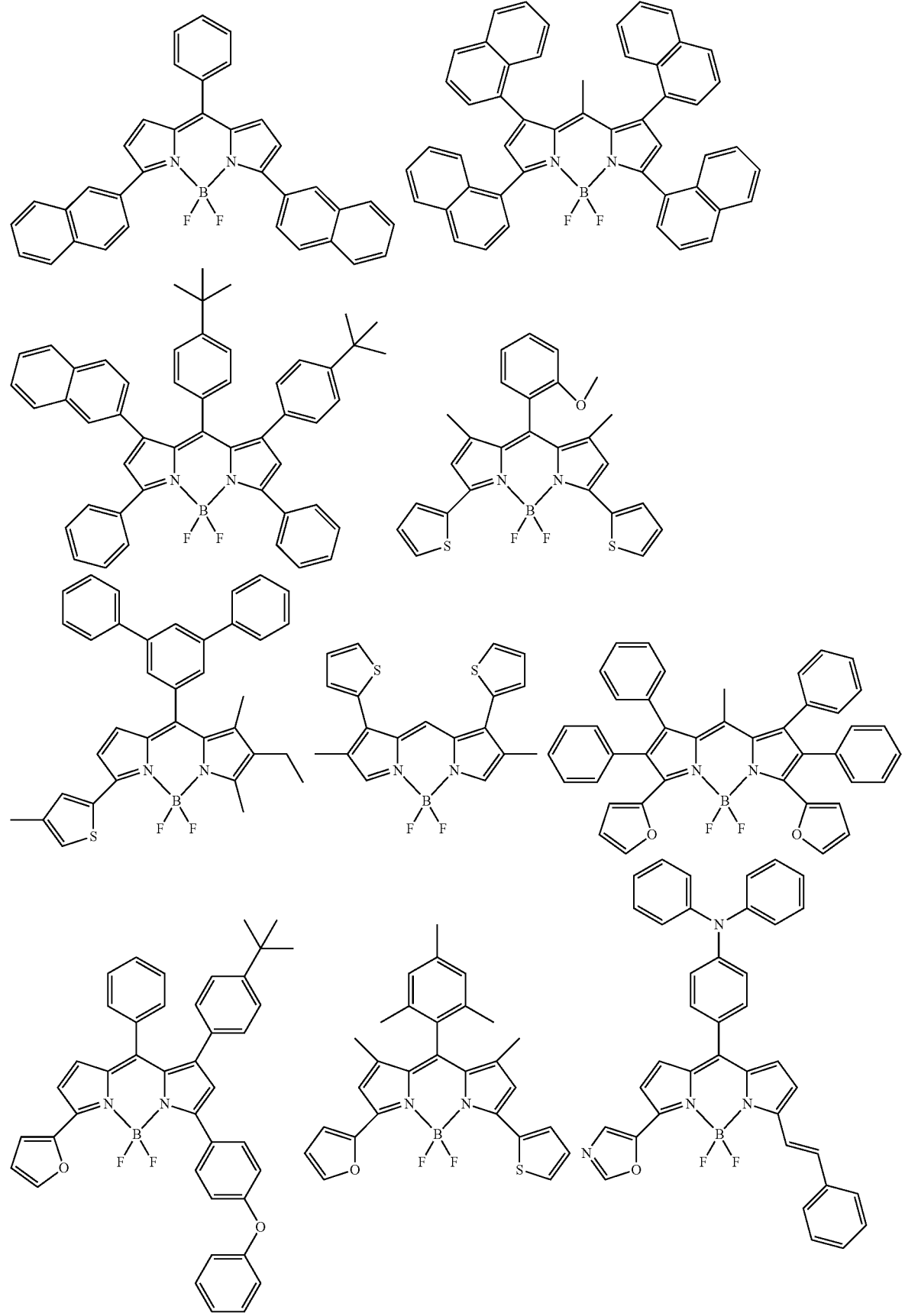

97
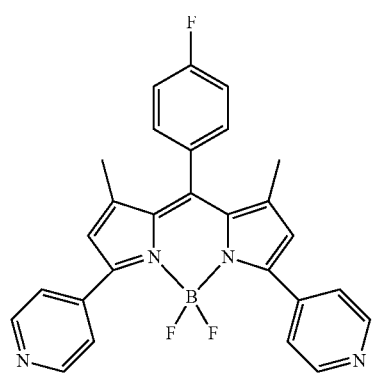
-continued
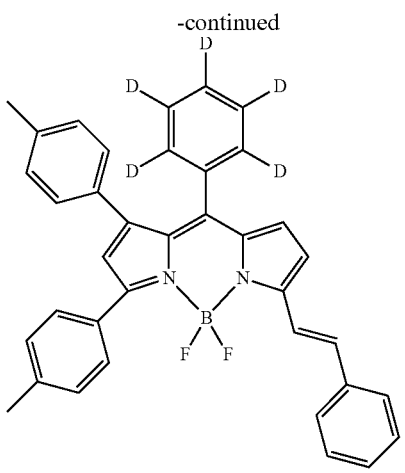
98
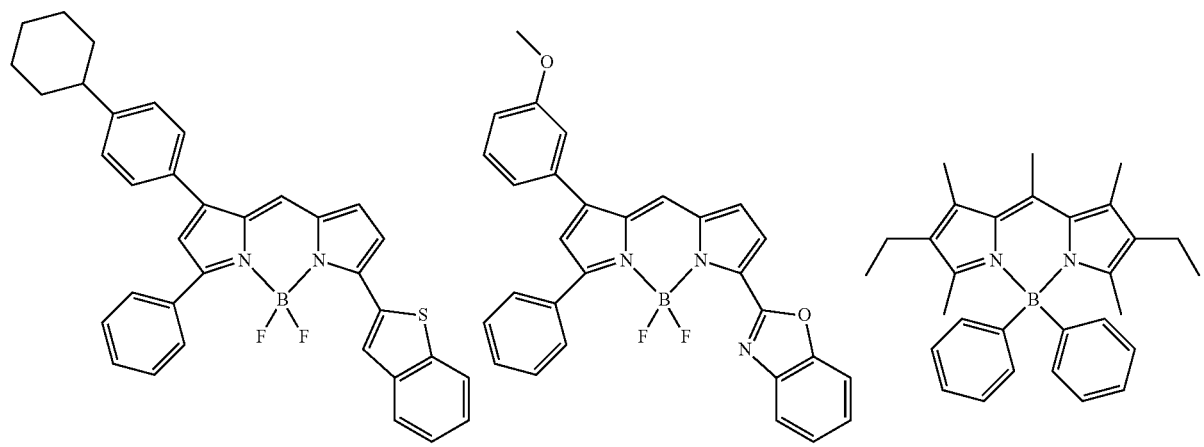
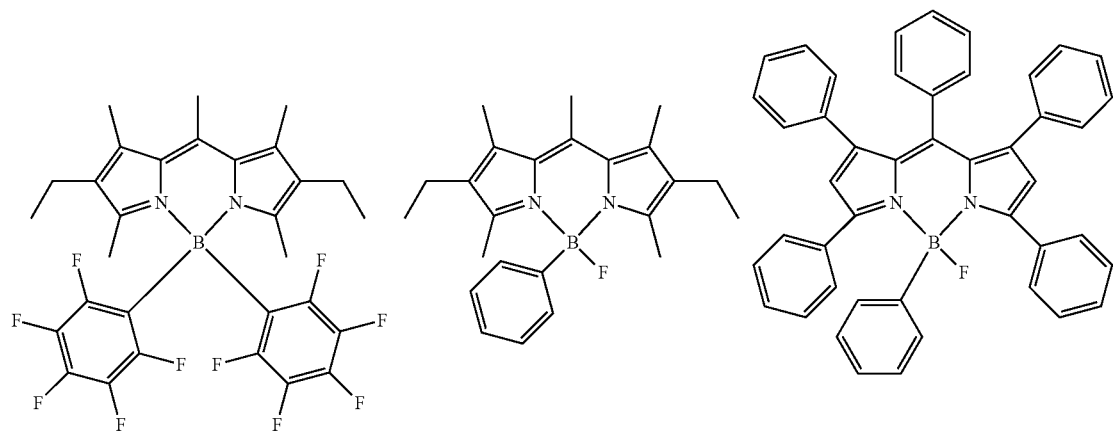

99
-continued
100
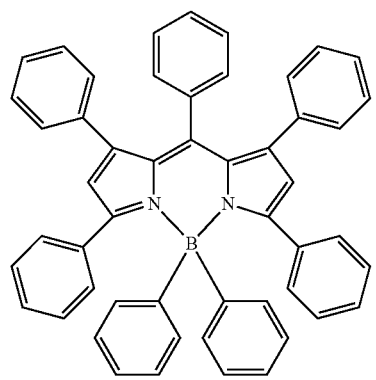
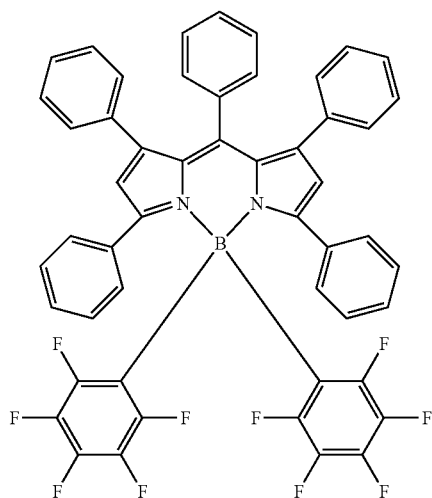
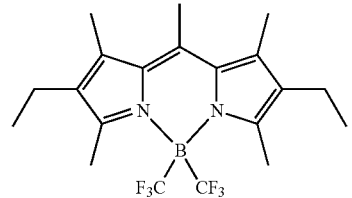
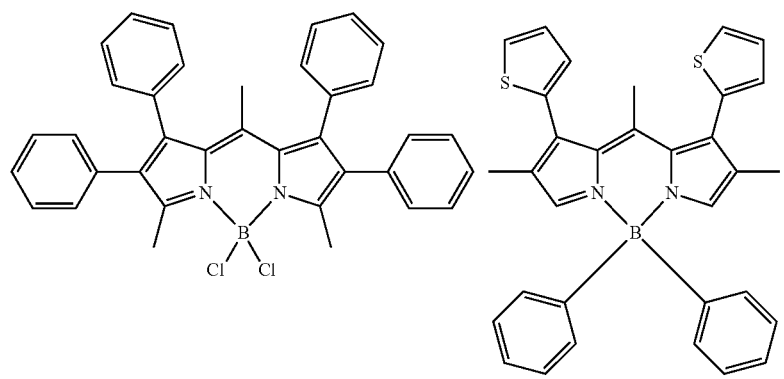
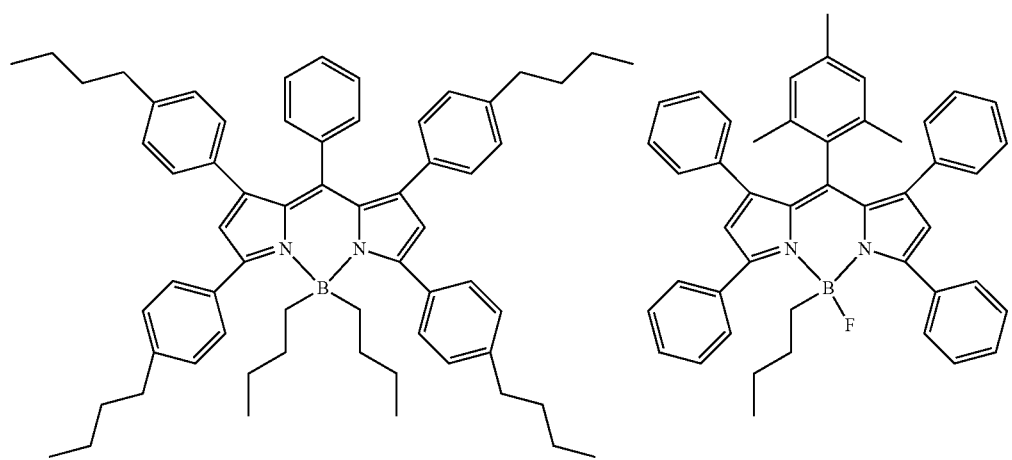

101
102
-continued
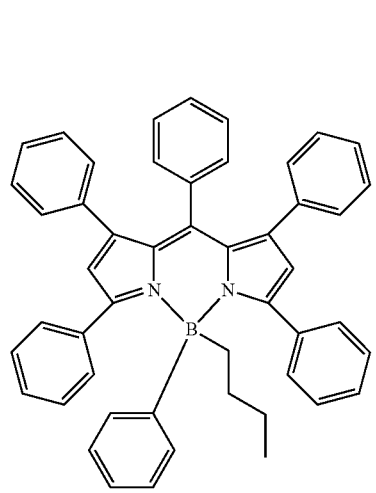
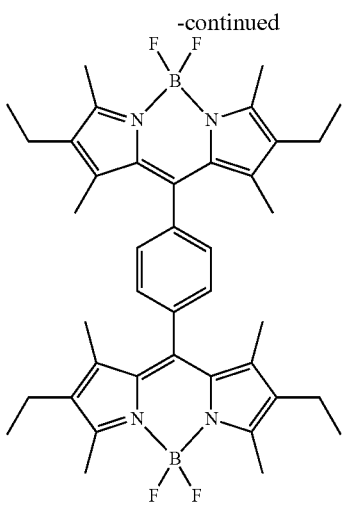
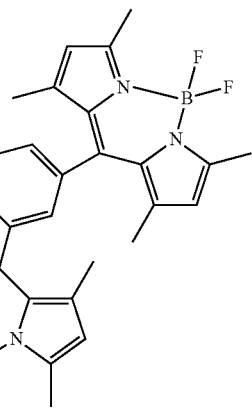
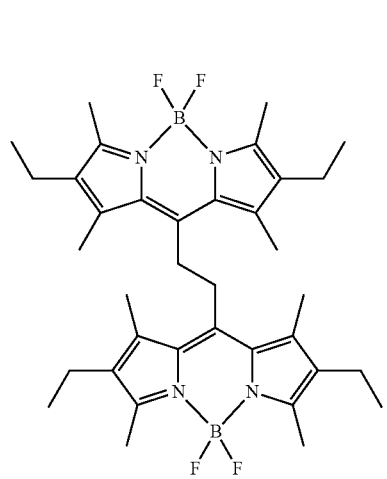
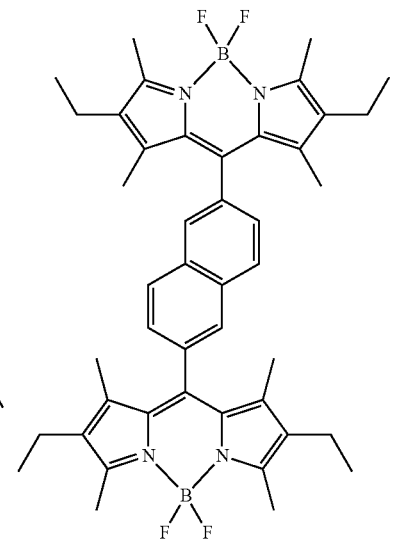
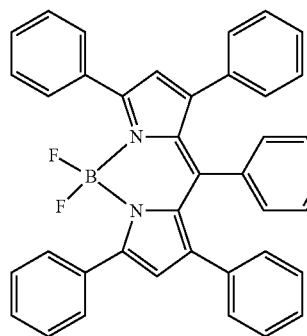
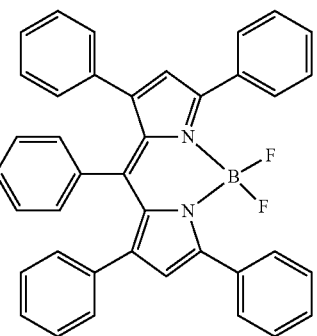
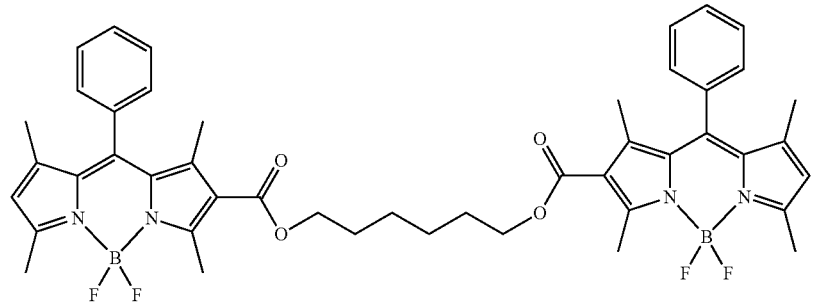

-continued
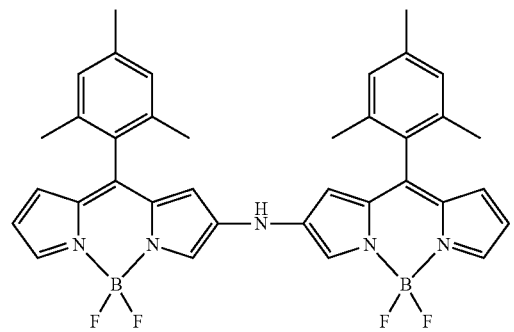
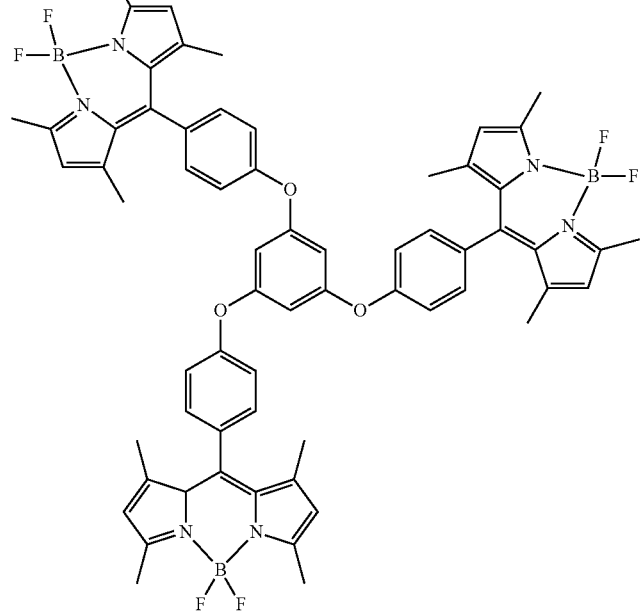
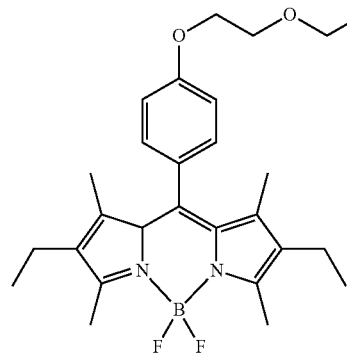
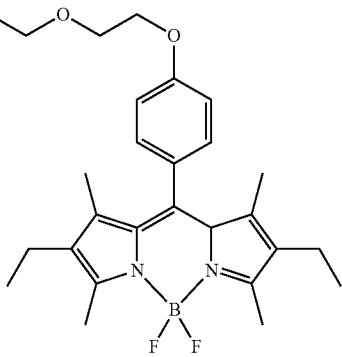
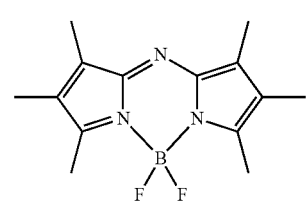
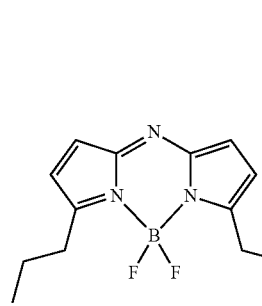
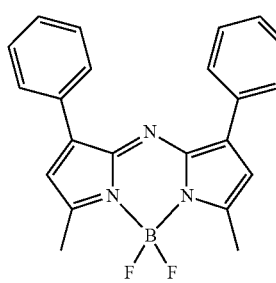
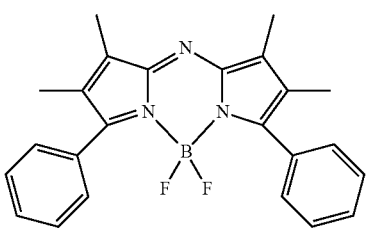
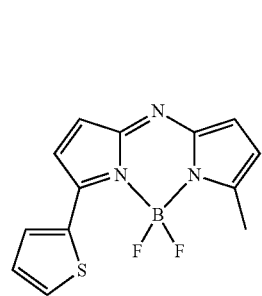
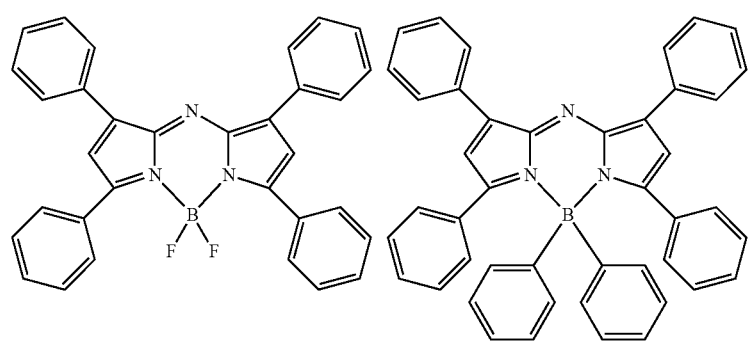

-continued
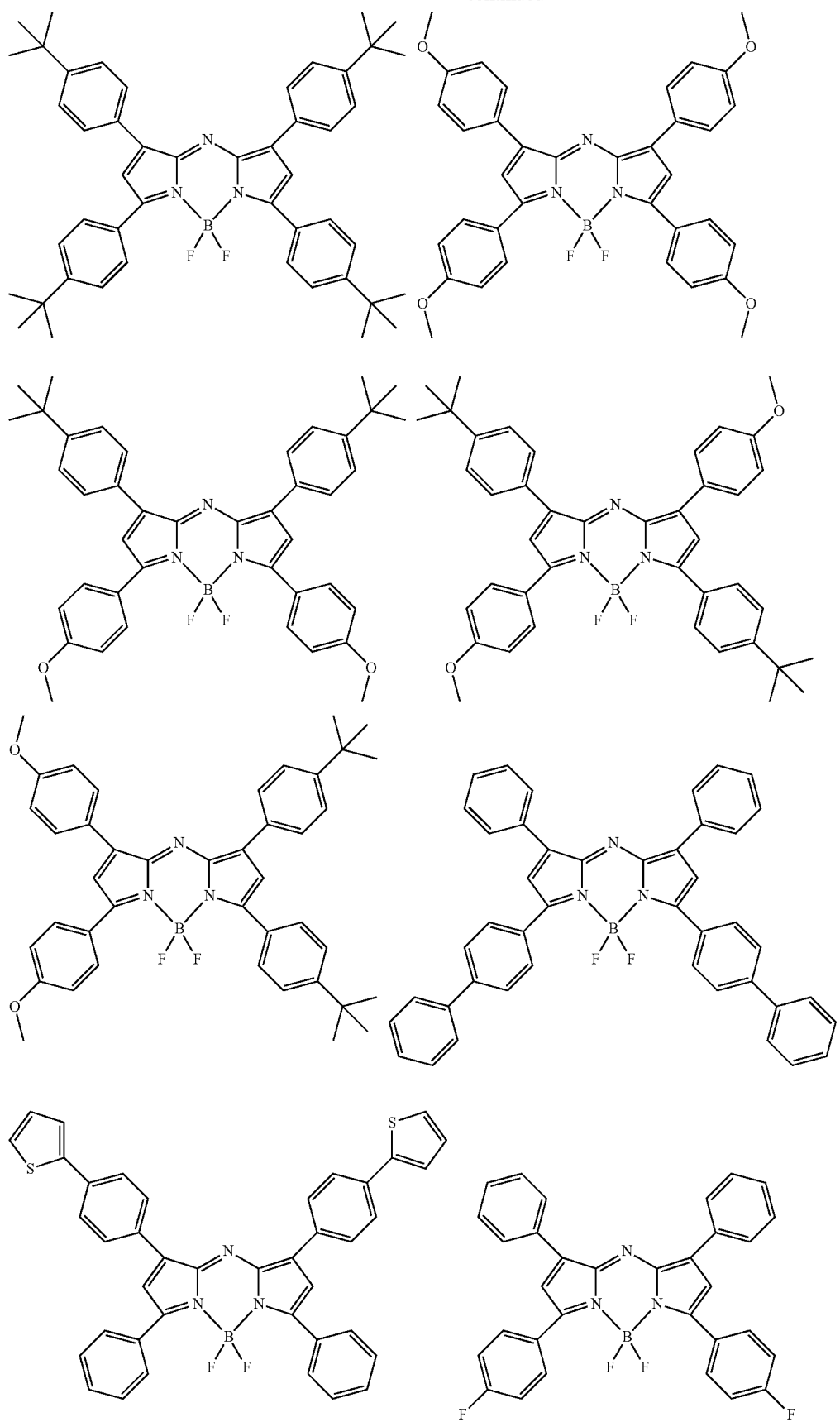

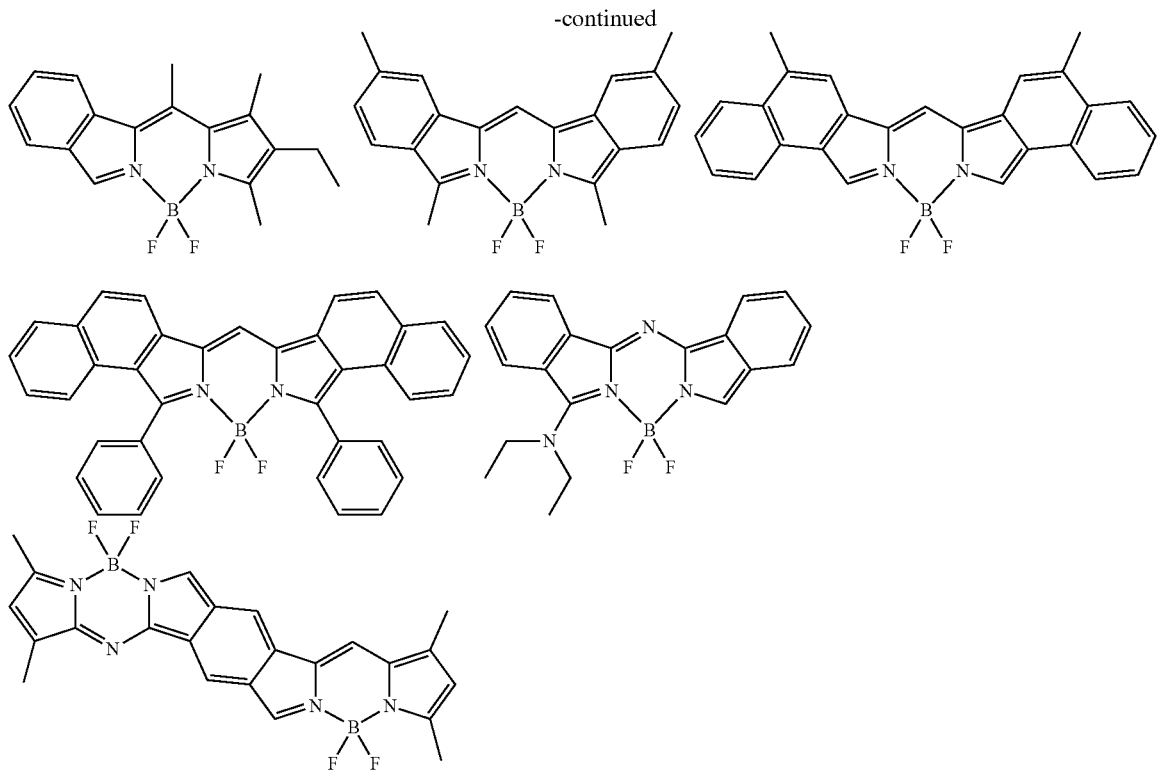

The compound represented by General Formula (8) can be manufactured by a method described in Japanese Translation of PCT Application No. H08-509471 and Japanese Patent Application Laid-open No. 2000-208262, for example. In other words, a pyrromethene compound and a metal salt are reacted with each other in the presence of a base to obtain a target pyrromethene-based metal complex.

For the synthesis of a pyrromethene-boron fluoride complex, methods described in J. Org. Chem., vol. 64, No. 21, pp. 7813-7819 (1999), Angew. Chem., Int. Ed. Engl., vol. 36, pp. 1333-1335 (1997), and the like are referred to, whereby the compound represented by General Formula (8) can be manufactured. Examples of the methods include a method that heats a compound represented by the following General Formula (10) and a compound represented by the following General Formula (11) in 1,2-dichloroethane in the presence of phosphoryl chloride and reacts them with a compound represented by the following General Formula (12) in 1,2-dichloroethane in the presence of triethylamine, thereby obtaining the compound represented by General Formula (8). However, the present invention is not limited to this method. $R^3$ to $R^{11}$ are similar to those described above. J represents halogen.

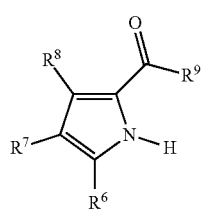

(10)

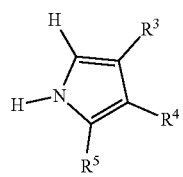

(11)

(12)

Furthermore, in introducing an aryl group or a heteroaryl group, there is a method that forms a carbon-carbon bond using a coupling reaction between a halogenated derivative and boronic acid or an esterified boronic acid derivative; the present invention is not limited to this method. Similarly, in introducing an amine group or a carbazolyl group, there is a method that forms a carbon-nitrogen bond using a coupling reaction between a halogenated derivative and an amine or a carbazole derivate in the presence of a metallic catalyst such as palladium, for example; the present invention is not limited to this method.

The color conversion composition according to the embodiment of the present invention can contain other compounds as appropriate as needed apart from the compound represented by General Formula (8). To further increase energy transfer efficiency to the compound represented by General Formula (8) from the excitation light, assist dopants such as rubrene may be contained, for example. When any light emission color other than the light emission color of the compound represented by General Formula (8) is desired to be added, the color conversion composition can add desired organic light-emitting materials, for example, compounds such as coumarin-based dyes, perylene-based dyes, phthalocyanine-based dyes, stilben-based dyes, cyanine-based dyes, polyphenylene-based dyes, rhodamine-based dyes, pyridine-based dyes, pyrromethene-based dyes, porphyrin dyes, oxazine-based dyes, and pyrazine-based dyes. Apart from these organic light-emitting materials, known light-emitting materials such as inorganic fluorescent bodies, fluorescent pigments, fluorescent dyes, and quantum dots can be added in combination.

The following shows examples of the organic light-emitting material other than the compound represented by General Formula (8); the present invention is not limited particularly to these examples.

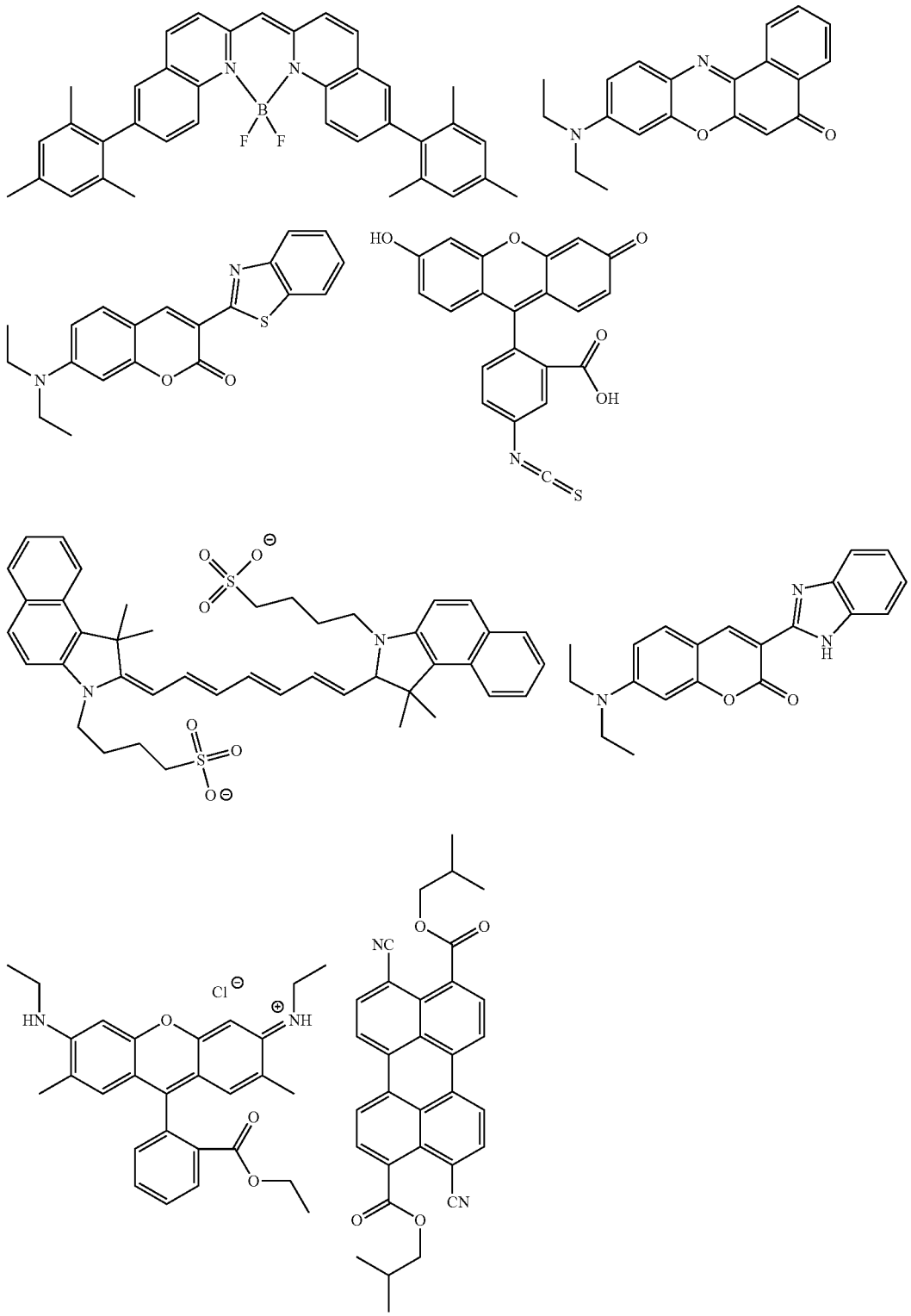

-continued
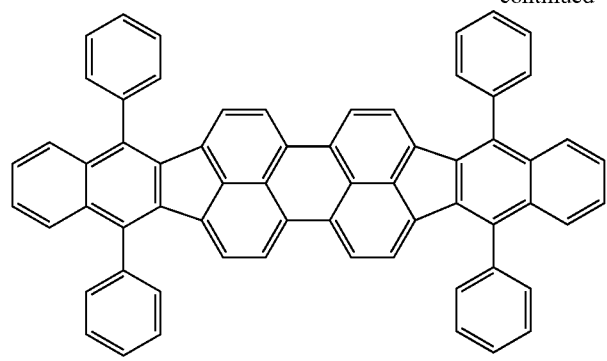
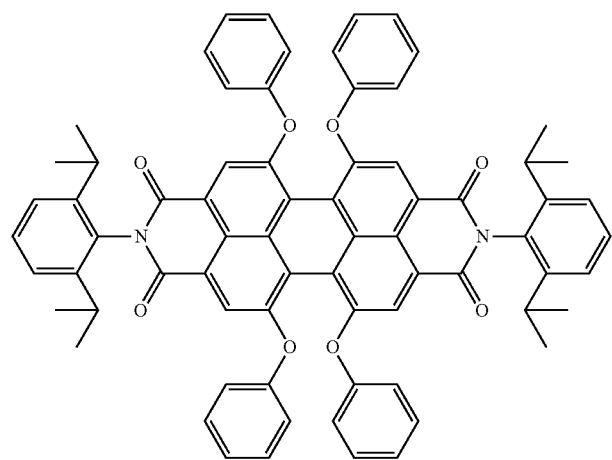
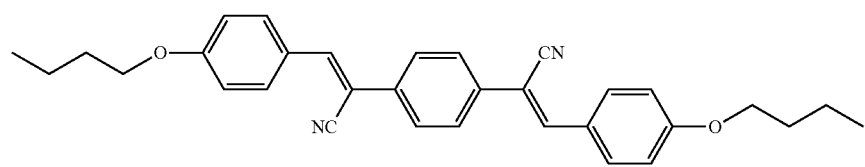
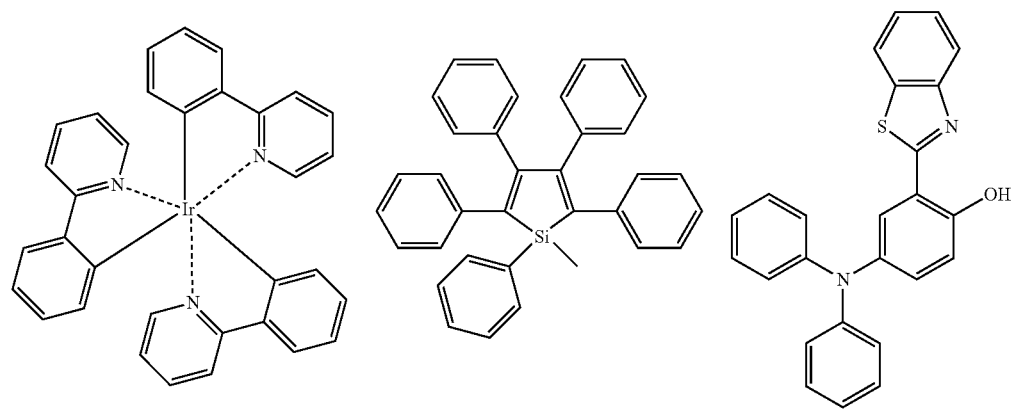

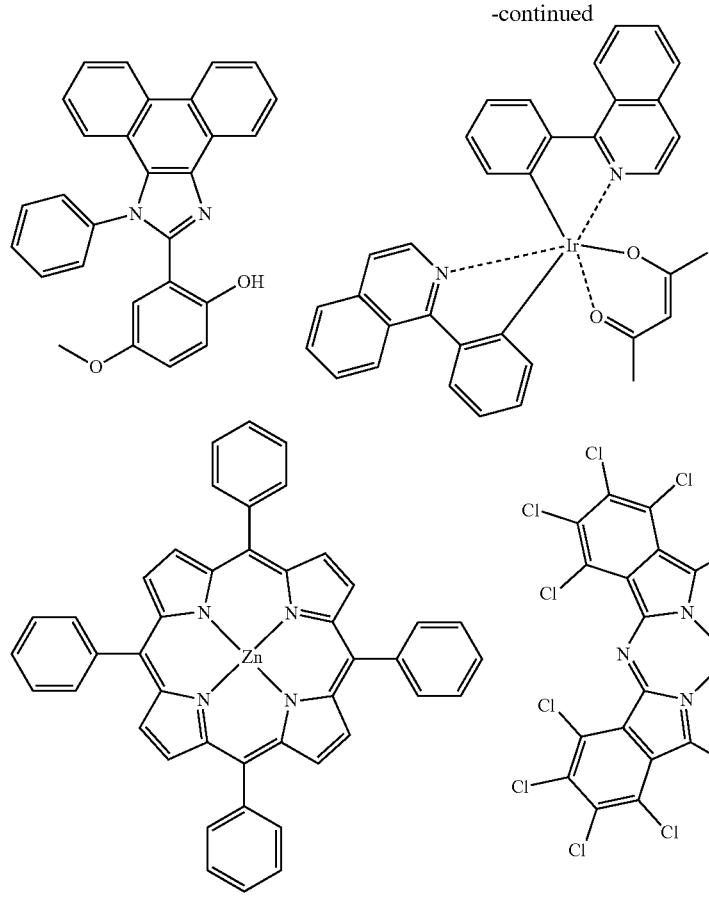
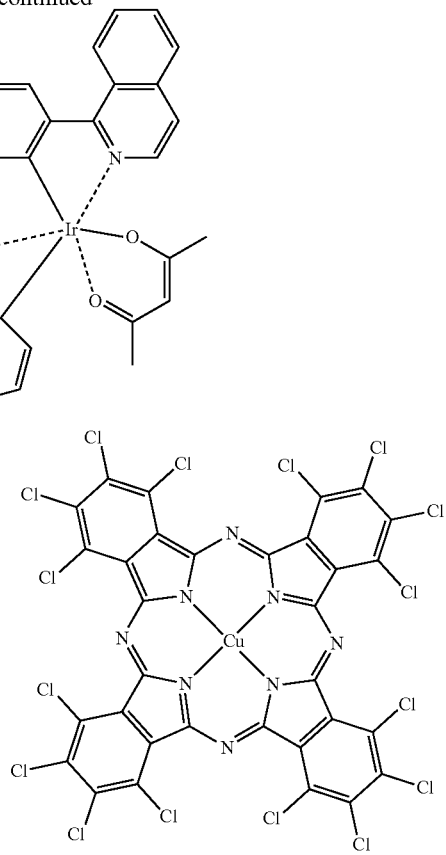

-continued

The color conversion composition according to the embodiment of the present invention preferably contains a light-emitting material (hereinafter, referred to as Light-Emitting Material (a)) that exhibits light emission with a peak wavelength observed in a region of 500 nm or more and 580 nm or less by using excitation light in a wavelength range of 400 nm or more and 500 nm or less. In the following, the light emission with a peak wavelength in the region of 500 nm or more and 580 nm or less is referred to as "green light emission." In general, excitation light with higher energy is likely to cause the decomposition of materials; the excitation light in the wavelength range of 400 nm or more and 500 nm or less has relatively low excitation energy and thus does not cause the decomposition of Light-Emitting Material (a) in the color conversion composition to obtain the green light emission with favorable color purity.

The color conversion composition according to the embodiment of the present invention preferably contains Light-Emitting Material (a) that exhibits light emission with a peak wavelength of 500 nm or more and 580 nm or less by using the excitation light in the wavelength range of 400 nm or more and 500 nm or less and a light-emitting material (hereinafter, referred to as Light-Emitting Material (b)) that exhibits light emission with a peak wavelength observed in a region of 580 nm or more and 750 nm or less by being excited by at least either the excitation light in the wavelength range of 400 nm or more and 500 nm or less or light emission from Light-Emitting Material (a). In the following, the light emission with a peak wavelength observed in the region of 580 nm or more and 750 nm or less is referred to as "red light emission."

Part of the excitation light in the wavelength range of 400 nm or more and 500 nm or less partially passes through the color conversion sheet according to the embodiment of the present invention, and when a blue LED with a sharp emission peak is used, sharp emission spectra are exhibited in the respective colors of blue, green, and red, and white light with favorable color purity can be obtained. Consequently, in displays in particular, a larger color gamut with more vivid colors can be efficiently made. In lighting use, light emission characteristics in the green region and the red region in particular are improved compared with a white LED in which a blue LED and a yellow fluorescent body are combined with each other, which is currently in the mainstream, thus improving color rendering and achieving a favorable white light source.

Preferred examples of Light-Emitting Material (a) include coumarin derivatives such as coumarin 6, coumarin 7, and coumarin 153; cyanine derivatives such as indocyanine green; fluorescein derivatives such as fluorescein, fluorescein isothiocyanate, and carboxyfluorescein diacetate; phthalocyanine derivatives such as phthalocyanine green, perylene derivatives such as diisobutyl-4,10-dicyanoperylene-3,9-dicarboxylate; pyrromethene derivatives; stilben derivatives; oxazine derivatives; naphthalimide derivatives; pyrazine derivatives; benzimidazole derivatives; benzoxazole derivatives; benzothiazole derivatives; imidazopyridine derivatives; azole derivatives; compounds having a condensed aryl ring such as anthracene and derivatives thereof; aromatic amine derivatives; and organic metal complex compounds. However, Light-Emitting Material (a) is not limited particularly to these examples. Among these compounds, pyrromethene derivatives give high fluorescence quantum yield, are favorable in durability, and are thus particularly preferred compounds; among them, the compound represented by General Formula (8) exhibits light emission with high color purity and is thus preferred.

Preferred examples of Light-Emitting Material (b) include cyanine derivatives such as 4-dicyanomethylene-2-methyl-6-(p-dimethylaminostyryl)-4H-pyran; rhodamine derivatives such as rhodamine B, rhodamine 6G, rhodamine 101, and sulforhodamine 101; pyridine derivatives such as 1-ethyl-2-(4-(p-dimethylaminophenyl)-1,3-butadienyl)-pyridinium-perchlorate; perylene derivatives such as N,N'-bis(2,6-diisopropylphenyl)-1,6,7,12-tetraphenoxyperylene-3,4:9,10-bis(dicarboimide); porphyrin derivatives; pyrromethene derivatives; oxazine derivatives; pyrazine derivatives; compounds having a condensed aryl ring such as naphthacene and dibenzodiindenoperylene and derivatives thereof; and organic metal complex compounds. However, Light-Emitting Material (b) is not limited particularly to these examples. Among these compounds, pyrromethene derivatives give high fluorescence quantum yield, are favorable in durability, and are thus particularly preferred compounds; among them, the compound represented by General Formula (8) exhibits light emission with high color purity and is thus preferred.

The content of Component (A) in the color conversion composition according to the embodiment of the present invention, which depends on the molar extinction coefficient, the fluorescence quantum yield, and the absorption intensity at an excitation wavelength of the compound and the thickness and the transmittance of a sheet to be prepared, is usually $1.0 \times 10^{-4}$ part by weight to 30 parts by weight, further preferably $1.0 \times 10^{-3}$ part by weight to 10 parts by weight, and particularly preferably $1.0 \times 10^{-2}$ part, by weight to 5 parts by weight relative to 100 parts by weight of Component (B).

When the color conversion composition contains both Light-Emitting Material (a) that exhibits the green light emission and Light-Emitting Material (b) that exhibits the red light emission, part of the green light emission is converted into the red light emission, and a content $w_a$ of Light-Emitting Material (a) and a content $w_b$ of Light-Emitting Material (b) preferably have a relation of $w_a \geq w_b$; the content ratio of the materials is $w_a:w_b=1,000:1$ to $1:1$, further preferably 500:1 to 2:1, and particularly preferably 200:1 to 3:1, where $w_a$ and $w_b$ are weight percentages relative to the weight of Component (B).

<Component (B): Resin>

The color conversion composition according to the embodiment of the present invention contains at least one of a polyester resin having a partial structure represented by General Formula (1) in its molecular structure and a resin containing a bisphenol structure represented by General Formula (2) as Component (B).

In the present invention, after intensive studies, the inventors of the present invention have found out that the degradation of the organic light-emitting material in the color conversion composition and the color conversion sheet is caused by oxidation degradation by oxygen and water vapor under light irradiation. It has been found out in particular that the compound represented by General Formula (8) is susceptible to oxidation degradation by oxygen and water vapor, while exhibiting high color purity and high fluorescence quantum yield.

Thus, to achieve both improvement in the color reproducibility and durability of the color conversion composition and the color conversion sheet, the entry of oxygen and water vapor to the organic light-emitting material (Component (A)) is required to be inhibited. However, simply covering the color conversion layer with a barrier layer, for example, cannot perfectly prevent the entry of oxygen and water vapor from a sheet end and a laminated interface, which failed to satisfactorily prevent the degradation of the organic light-emitting material.

After intensive studies, the inventors of the present invention have found out that the use of either one or both of a polyester resin having a partial structure represented by General Formula (1) in its molecular structure and a resin containing a bisphenol structure represented by General Formula (2) as components of the binder resin (Component (B)) can inhibit the degradation of the organic light-emitting material as Component (A) and greatly improve the durability of the color conversion composition and the color conversion sheet.

(1)

In General Formula (1), Y is a divalent saturated aliphatic hydrocarbon group having at least one of a tertiary carbon and a quaternary carbon.

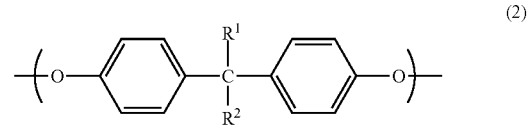
(2)

In General Formula (2), $R^1$ and $R^2$ each represent hydrogen or a $C_{1-20}$ organic group. $R^1$ and $R^2$ may be the same as or different from each other.

In the present invention, the resin as Component (B) contained in the color conversion composition may be a single component of the polyester resin having a partial structure represented by General Formula (1) or a single component of the resin containing the bisphenol structure represented by General Formula (2). The resin as Component (B) may be a mixture of a plurality kinds of resins having the partial structure represented by General Formula (1) and resins containing the bisphenol structure represented by General Formula (2). Furthermore, the resin as Component (B) may be a mixture or a copolymer of these resins or a mixture or a copolymer with other resins.

Examples of the other resins to be combined include known ones such as photocurable resist materials having a reactive vinyl group such as acrylic acid-based, methacrylic acid-based, vinyl polycinnamate-based, or cyclized rubber-based one, epoxy resins, phenoxy resins, silicone resins (including organopolysiloxane cured objects (cross-linked objects) such as silicone rubbers and silicone gels), urea resins, fluorine resins, polycarbonate resins, acrylic resins, urethane resins, melamine resins, polyvinyl resins, polyamide resins, phenol resins, polyvinyl alcohol resins, polyvinyl butyral resins, aliphatic alcohol resins, cellulose resins, aliphatic ester resins, aromatic ester resins, aliphatic polyolefin resins, and aromatic polyolefin resins. A copolymerized resin of these resins may be used. These resins are designed as appropriate, whereby the resin (Component (B))

useful for the color conversion composition and the color conversion sheet according to the embodiment of the present invention is obtained.

Among these resins, because of the easiness of the process of sheeting, thermosetting resins are further preferred. Among the thermosetting resins, in view of transparency and heat resistance in particular, preferred examples include epoxy resins, phenoxy resins, silicone resins, acrylic resins, polyvinyl alcohol resins, polyvinyl butyral resins, aliphatic alcohol resins, and mixtures thereof.

(Polyester Resin Having Partial Structure Represented by General Formula (1) in its Molecular Structure)

In the polyester resin having a partial structure represented by General Formula (1) in its molecular structure of the present invention, Y has a branched saturated aliphatic hydrocarbon, and packing of molecular chains of the polyester resin is inhibited. The entire resin thereby becomes flexible, whereby the polyester resin having a partial structure represented by General Formula (1) exhibits adhesiveness to a wide range of materials. With this adhesiveness, the color conversion composition formed into a sheet form strongly adheres to a base layer or the barrier layer, and the entry of oxygen and water vapor from the laminated interface can be prevented.

The polyester resin having a partial structure represented by General Formula (1) in its molecular structure has many ester bonds in the molecular chains. The ester bonds partially form hydrogen bonds between the molecular chains of the resin to reduce the free volume of the resin, whereby this polyester resin exhibits high gas barrier property. Consequently, the polyester resin having a partial structure represented by General Formula (1) is contained as the component of the binder resin (Component (B)), whereby the degradation of the organic light-emitting material (Component (A)) by oxygen and water vapor can be inhibited.

The polyester resin contained as Component (B) of the present invention is preferably amorphous in view of transparency. Being amorphous indicates that a melting peak appears in neither of two temperature raising processes included in temperature raising at 20° C./min from −100° C. to 300° C., subsequent temperature dropping at 50° C./min to −100° C., and subsequent temperature raising at 20° C./min from −100° C. to 300° C. using a differential scanning calorimeter (DSC). In contrast, a clear melting peak appearing in either of the temperature raising processes means crystalline. In this case, the polyester resin having a partial structure represented by General Formula (1), in which the packing of molecular chains is inhibited, is likely to exhibit amorphous property and exhibits high transparency. Consequently, the polyester resin having a partial structure represented by General Formula (1) does not hinder the light from the light source and the light emission of the light-emitting material.

When Y in General Formula (1) is at least one selected from groups of the following structures, the packing of molecular chains is strongly inhibited, and adhesiveness and transparency improve, which is preferred.

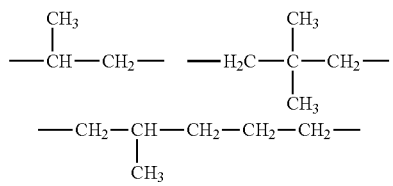

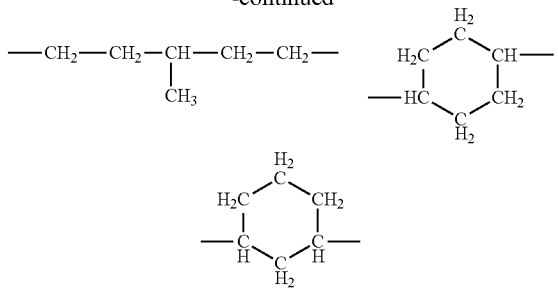

Among them, Y in General Formula (1) particularly preferably contains a group of the following structure.

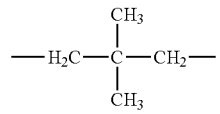

The polyester resin having a partial structure represented by General Formula (1) more preferably has at least one of a partial structure represented by General Formula (3) and a partial structure represented by General Formula (4) in its molecular structure:

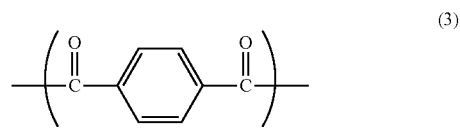

(3)

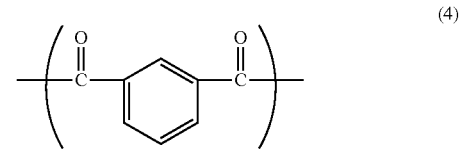

(4)

The partial structure represented by General Formula (3) or General Formula (4) has a benzene ring and causes interaction between the molecular chains of the polyester resin to form partial stacks. This partial structure thereby imparts moderate strength to the resin as Component (B). Furthermore, the free volume of the resin reduces by the interaction between the molecular chains, and the polyester resin having this partial structure exhibits higher gas barrier property. Consequently, the effect of inhibiting the degradation of the organic light-emitting material by oxygen and water vapor is enhanced.

The partial structure represented by General Formula (4) is a 1,3-substituted benzene and thus also contributes to the inhibition of packing. Consequently, the ratio of the partial structure represented by General Formula (4) in the molecular structure is adjusted, whereby a balance among the flexibility, strength, and gas barrier property of the resin as Component (B) can be adjusted.

The polyester resin having a partial structure represented by General Formula (1) further preferably has at least one of a partial structure represented by General Formula (5) and a partial structure represented by General Formula (6) in its molecular structure.

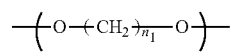

(5)

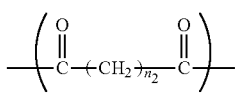

(6)

In General Formula (5) or General Formula (6), $n_1$ and $n_2$ are natural numbers, in which $2 \leq n_1 \leq 10$ and $2 \leq n_2 \leq 14$.

These parts contain a linear aliphatic hydrocarbon and can thus suppress the rigidity of the resin and increase the flexibility and dissolution stability thereof.

If the carbon number of the linear aliphatic hydrocarbon part is excessively large, the packing among molecular chains is strong, and the flexibility of the resin reduces. For this reason, $n_1$ is preferably 10 or less. Furthermore, in view of raw material costs, $n_1$ is preferably 8 or less, more preferably 6 or less, further preferably 4 or less, and particularly preferably 2. Similarly, $n_2$ is preferably 14 or less. Furthermore, in view of raw material costs, $n_2$ is preferably 12 or less, more preferably 10 or less, and further preferably 8. In other words, the case that $n_1$ is 2 and $n_2$ is 8 is particularly preferred in view of raw material costs.

The partial structures represented by General Formula (1) and General Formulae (3) to (6) are extremely small in light absorption in the visible range, and the polyester resin containing these parts is small in light absorption in the visible range and does not hinder the light from the light source and the light emission of the light-emitting material. Also, when the polyester resin as Component (B) has a partial structure other than the partial structures represented by General Formula (1) and General Formulae (3) to (6), the partial structure is preferably extremely small in light absorption in the visible range.

When the weight ratio of the partial structure represented by General Formula (1) to the total amount of the polyester resin contained as Component (B) in the color conversion composition according to the embodiment of the present invention is represented as $m_1$% by weight, the range of $m_1$ is preferably $10 \leq m_1 \leq 60$, more preferably $10 \leq m_1 \leq 50$, further preferably $10 \leq m_1 \leq 40$, and particularly preferably $15 \leq m_1 \leq 30$. When $m_1$ is the lower limit value or more, the flexibility of the resin as Component (B) can be further improved, and the adhesiveness of the resin composition can be further improved. When $m_1$ is the upper limit value or less, thermal stability when the resin composition is formed into a sheet form can be further improved.

When the weight ratio of the partial structure represented by General Formula (3) to the total amount of the polyester resin contained as Component (B) in the color conversion composition according to the embodiment of the present invention is represented as $m_2$% by weight, the range of $m_2$ is preferably $15 \leq m_2 \leq 70$, more preferably $20 \leq m_2 \leq 70$, further preferably $25 \leq m_2 \leq 60$, and particularly preferably $25 \leq m_2 \leq 50$. When $m_2$ is the lower limit value or more, the strength of the resin composition can be further improved. When $m_2$ is the upper limit value or less, the flexibility of the resin as Component (B) can be further improved, and flexibility when the resin composition is formed into a sheet form can be further improved.

When the weight ratio of the partial structure represented by General Formula (4) to the total amount of the polyester resin contained as Component (B) in the color conversion composition according to the embodiment of the present invention is represented as $m_3$% by weight, the range of $m_2+m_3$ is preferably $20 \leq m_2+m_3 \leq 70$, more preferably $30 \leq m_2+m_3 \leq 70$, and further preferably $40 \leq m_2+m_3 \leq 65$. When $m_2+m_3$ is the lower limit value or more, the glass transition temperature of the resin as Component (B) is higher, and thermal stability when the resin composition is formed into a sheet form can be further improved. When $m_2+m_3$ is the upper limit value or less, the flexibility of the resin as Component (B) can be further improved, and flexibility when the resin composition is formed into a sheet form can be further improved. When the range of $m_2+m_3$ is $50 \leq m_2+m_3 \leq 65$ in particular, Component (B) exhibits higher gas barrier property, which is preferred.

When the weight ratio of the partial structure represented by General Formula (5) to the total amount of the polyester resin contained as Component (B) in the color conversion composition according to the embodiment of the present invention is represented as $m_4$% by weight, the range of $m_4$ is preferably $0 \leq m_4 \leq 40$, more preferably $0 \leq m_4 \leq 30$, further preferably $5 \leq m_4 \leq 30$, and particularly preferably $10 \leq m_4 \leq 30$. When $m_4$ is the lower limit, value or more, the flexibility of the resin as Component (B) can be further improved, flexibility when the resin composition is formed into a sheet form can be further improved, and the strength of the resin composition can be further improved. When $m_4$ is the upper limit value or less, the packing among the resin molecular chains can be made more appropriate, and the flexibility of the resin as Component (B) can be further improved.

When the weight ratio of the partial structure represented by General Formula (6) to the total amount of the polyester resin contained as Component (B) in the color conversion composition according to the embodiment of the present invention is represented as $m_5$% by weight, the range of $m_4+m_5$ is preferably $0 \leq m_4+m_5 \leq 60$, more preferably $5 \leq m_4+m_5 \leq 50$, further preferably $10 \leq m_4+m_5 \leq 40$, and particularly preferably $10 \leq m_4+m_5 \leq 30$. When $m_5$ the lower limit value or more, the dissolution stability of Component (B) can be improved. When $m_5$ is the upper limit value or less, the glass transition temperature of the resin as Component (B) is higher, and thermal stability when the resin composition is formed into a sheet form can be further improved.

The weight average molecular weight of the polyester resin having a partial structure represented by General Formula (1) is more preferably 5,000 or more and 100,000 or less. When two or more kinds of polyester resins having a partial structure represented by General Formula (1) are contained as Component (B), only the weight average molecular weight of at least one of them is required to be within the range. When this weight average molecular weight is 5,000 or more, the mechanical strength of a cured film of the color conversion composition improves, the occurrence of cracks and the like are inhibited, and a highly reliable color conversion sheet can be obtained. When this weight average molecular weight is 100,000 or less, the fluidity of the color conversion composition is high, and the adhesiveness between the color conversion composition after being cured and the base improves.

The weight average molecular weight in the present invention is a value measured by gel permeation chromatography (GPC). Specifically, the value is a value determined in terms of polystyrene using GFC (HLC-82A manufactured by Tosoh Corporation) (developing solvent: tetrahydrofuran, developing rate: 1.0 ml/min, column: TSKgelG2000HXL manufactured by Tosoh Corporation) after a sample is filtered with a membrane filter with a pore diameter of 0.45 μm.

Examples of commercially available products of the polyester resin having a partial structure represented by General Formula (1) include "VYLON" series manufactured by Toyobo Co., Ltd. and "Nichigo-POLYESTER" series manufactured by The Nippon Synthetic Chemical Industry Co., Ltd. Specific examples thereof include VYLON270 (manufactured by Toyobo Co., Ltd.), VYLON600 (manufactured by Toyobo Co., Ltd.), VYLON630 (manufactured by Toyobo Co., Ltd.), TP-220 (manufactured by The Nippon Synthetic Chemical Industry Co., Ltd.), TP-294 manufactured by The Nippon Synthetic Chemical Industry Co., Ltd.), and LP-033 (manufactured by The Nippon Synthetic Chemical Industry Co., Ltd.).

(Resin Containing Bisphenol Structure Represented by General Formula (2))

When the resin containing a bisphenol structure is used as Component (B) (the binder resin, for example) contained in the color conversion composition according to the embodiment of the present invention, this resin is low in oxygen permeability in a sheet form after being thermoset, thus inhibits the oxidation degradation of the organic light-emitting material as Component (A), and greatly improves the durability of the color conversion sheet. The resin containing a bisphenol structure is also excellent in transparency, heat resistance, and chemical resistance and has favorable characteristics as a color conversion sheet for optical use in particular. The resin containing a bisphenol structure refers to a resin containing a bisphenol structure shown below in its molecule.

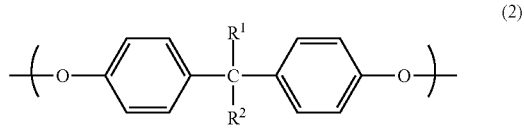

(2)

In General Formula (2), $R^1$ and $R^2$ each represent hydrogen or a $C_{1-20}$ organic group. $R^1$ and $R^2$ may be the same as or different from each other.

The resin containing the bisphenol structure may be a homopolymer containing the repetition of the bisphenol structure alone or a copolymer resin combined with other resins. Examples of the other resins to be combined include known ones such as photocurable resist materials having a reactive vinyl group such as acrylic acid-based, methacrylic acid-based, vinyl polycinnamate-based, or cyclized rubber-based one, epoxy resins, phenoxy resins, silicone resins (including organopolysiloxane cured objects (cross-linked objects) such as silicone rubbers and silicone gels), urea resins, fluorine resins, polycarbonate resins, acrylic resins, urethane resins, melamine resins, polyvinyl resins, polyamide resins, phenol resins, polyvinyl alcohol resins, polyvinyl butyral resins, aliphatic alcohol resins, cellulose resins, aliphatic ester resins, aromatic ester resins, aliphatic polyolefin resins, and aromatic polyolefin resins. A copolymerized resin of these resins may be used. These resins are designed as appropriate, whereby the resin as Component (B) useful for the color conversion composition and the color conversion sheet according to the embodiment of the present invention is obtained.

Among these resins, because of the easiness of the process of sheeting, thermosetting resins are further preferred. Among the thermosetting resins, in view of transparency and heat resistance in particular, preferred examples include epoxy resins, phenoxy resins, silicone resins, acrylic resins, polyvinyl alcohol resins, polyvinyl butyral resins, aliphatic alcohol resins, and mixtures thereof.

An aliphatic alcohol structure is further preferred as a structure to be combined with the bisphenol structure because of being particularly excellent in adhesiveness and reactivity with the base. The structure of the aliphatic alcohol structure is most preferably a 2-propanol structure represented by General Formula (7). In other words, the resin containing a bisphenol structure is preferably a resin containing a bisphenol structure and a 2-propanol structure.

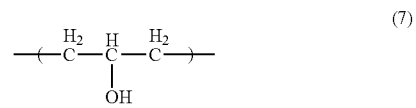

(7)

In the present invention, the resin containing a bisphenol structure preferably has an epoxy group. Examples of the epoxy group include an oxirane group, a glycidyl ether group, glycidyl amine, and glycidyl ester. With this structure, thermosettability can be imparted to the resin. Consequently, after being cured, this resin exhibits strong adhesiveness to a wide range of materials and gives strong adhesion strength to the base layer and the barrier layer in particular. In addition, this resin has an epoxy group in its molecule and thus produces an effect of being excellent in water resistance and chemical resistance after being cured and producing no shrinkage strain during being cured.

Preferred examples of the material of the resin containing an epoxy group include epoxy resins such as a bisphenol A type epoxy resin, a bisphenol F type epoxy resin, a copolymer of a bisphenol A type epoxy resin and a bisphenol F type epoxy resin, and a naphthacene type epoxy resin. These resins are low in stickiness at room temperature and can exhibit stickiness by being heated to 50° C. or more, and when the color conversion composition formed into a sheet form is stuck to the base layer or a barrier film in particular, it can be stuck thereto simply without the mixing of air bubbles by lamination by heating.

To prevent the thermal decomposition of the pyrromethene derivative in lamination by heating, a resin having a low glass transition temperature (Tg) is preferably used. Specifically, preferred examples of the resin include a bisphenol A type epoxy resin and a bisphenol F type epoxy resin.

Two or more epoxy groups are preferably contained in the molecule of the resin in view of being cured through a ring-opening reaction. The epoxy groups are preferably bonded to ends of the resin molecule, whereby flexibility occurs in the resin, and crack resistance increases.

For the resin containing a bisphenol structure, the phenoxy resin may be a commercially available phenoxy resin such as YP-50S (bisphenol A type phenoxy resin, manufactured by NSCC Epoxy Manufacturing Co., Ltd.), YP-70 (bisphenol A/F type phenoxy resin, manufactured by NSCC Epoxy Manufacturing Co., Ltd.), FX-316 (bisphenol F type phenoxy resin, manufactured by NSCC Epoxy Manufacturing Co., Ltd.), or FX-280S (cardo skeleton type phenoxy resin, manufactured by NSCC Epoxy Manufacturing Co., Ltd.).

To further enhance the adhesiveness between the resin containing a bisphenol structure and the base, the color conversion composition or the color conversion sheet may contain a curing agent such as an amine or an acid anhydride, or a surface modifier such as polyester, acrylic, or urethane may be applied to the base. In addition, an epoxy compound may be further added to the color conversion composition or the color conversion sheet; in this case, the epoxy compound preferably has an epoxy equivalent of 100 to 500. When the epoxy equivalent is 100 or more, the toughness of a cured adhesive composition can be increased. When the epoxy equivalent is 500 or less, the cross-linked density of the cured adhesive composition is high, and heat resistance can be improved.

The epoxy equivalent is a value measured by dissolving a sample in chloroform, adding acetic acid and an acetic acid solution of tetramethylammonium bromide were added thereto, and performing potentiometric titration with a 0.1 mol/l perchloric acid-acetic acid standard solution based on JIS K7236-2001.

The weight average molecular weight of the resin containing a bisphenol structure is preferably 10,000 or more and 100,000 or less. When two or more kinds of resins containing a bisphenol structure are contained as Component (B), only the weight average molecular weight of at least one of them is required to be within the range. When this weight average molecular weight is 10,000 or more, the mechanical strength of a cured film of the color conversion composition improves, the occurrence of cracks and the like are inhibited, and a highly reliable color conversion sheet can be obtained. When this weight average molecular weight is 100,000 or less the fluidity of the color conversion composition is high, an the adhesiveness between the color conversion composition after being cured and the base improves.

<Other Additives>

The color conversion composition according to the embodiment of the present invention can contain antioxidants processing-and-thermal stabilizers, lightfast stabilizers such as ultraviolet light absorbents, dispersants and leveling agents for stabilizing coatings, plasticizers, cross-linking agents such as epoxy compounds, curing agents such as amines, acid anhydrides, and imidazole, adhesive assistants such as silane coupling agents as a modifier for sheet surface, and inorganic particles such as silica particles and silicone fine particles and silane coupling agents as a color conversion material settling inhibitor, apart from Component (A) and Component (B).

Examples of the antioxidants include, but are not limited to, phenol-based antioxidants such as 2,6-di-tert-butyl-p-cresol and 2,6-di-tert-butyl-4-ethylphenol. These antioxidants may be contained singly or in combination.

Examples of the processing-and-thermal stabilizers include, but are not limited to, phosphorous-based stabilizers such as tributyl phosphite, tricyclohexyl phosphite, triethyl phosphine, and diphenylbutyl phosphine. These stabilizers may be contained singly or in combination.

Examples of the lightfast stabilizers include, but are not limited to, benzotriazoles such as 2-(5-methyl-2-hydroxyphenyl)benzotriazole and 2-[2-hydroxy-3,5-bis(α,α-dimethylbenzyl)phenyl]-2H-benzotriazole. These lightfast stabilizers may be contained singly or in combination.

In order not to hinder the light from the light source and the light emission of the light-emitting material, these additives are preferably small in an extinction coefficient in the visible range. Specifically, a molar extinction coefficient ε is preferably 1,000 or less, more preferably 500 or less, further preferably 200 or less, and particularly preferably 100 or less in the entire wavelength range of 400 nm or more and 800 nm or less.

For the lightfast stabilizers, compounds having a role as a singlet oxygen quencher can also be suitably used. The singlet oxygen quencher is a material that traps singlet oxygen produced from oxygen molecules activated through optical energy and deactivates the singlet oxygen. The singlet oxygen quencher coexisting in the composition can prevent the light-emitting material from degrading by the singlet oxygen.

It is known that the singlet oxygen is produced by the occurrence of electron and energy exchange between a triplet excited state of dye such as rose bengal or methylene blue and an oxygen molecule in the ground state.

In the color conversion composition according to the embodiment of the present invention, the contained organic light-emitting material is excited by the excitation light and emits light with a wavelength different from that of the excitation light to perform light color conversion. This excitation-emission cycle is repeated, and interaction between produced excited species and oxygen contained in the composition increases the probability of the singlet oxygen being produced. Consequently, the probability of collision of the organic light-emitting material and the singlet oxygen also increases, and the degradation of the organic light-emitting material is likely to proceed.

Organic light-emitting materials are susceptible to the influence of the singlet oxygen compared with inorganic light-emitting materials. The compound represented by General Formula (8) in particular is higher in reactivity with the singlet oxygen than compounds having a condensed aryl ring such as perylene or derivatives thereof and thus receives a large influence on durability by the singlet oxygen. Given these circumstances, the produced singlet oxygen is quickly deactivated by the singlet oxygen quencher, whereby the durability of the compound represented by General Formula (3) excellent in quantum yield and color purity can be improved.

Examples of the compounds having a role as a singlet oxygen quencher include, but are not limited to, specific tertiary amines, catechol derivatives, and nickel compounds. These lightfast stabilizers may be contained singly or in combination.

The tertiary amines refer to compounds having a structure in which all the N—H bonds of ammonia are replaced with N—C bonds. The substituent on the nitrogen atom is selected from an alkyl group, a cycloalkyl group, a heterocyclic group, an alkenyl group, a cycloalkenyl group, an alkynyl group, an aryl group, a heteroaryl group, an aldehyde group, a carbonyl group, a carboxy group, an oxycarbonyl group, a carbamoyl group, and a condensed ring and an aliphatic ring formed between adjacent substituents. These substituents may be further substituted by the substituents described above.

The substituent on the nitrogen atom of the tertiary amines is preferably a substituted or unsubstituted alkyl group, a substituted or unsubstituted cycloalkyl group, a substituted or unsubstituted aryl group, or a substituted or unsubstituted heteroaryl group in view of photostability and more preferably a substituted or unsubstituted alkyl group, a substituted or unsubstituted cycloalkyl group, or a substituted or unsubstituted aryl group.

The aryl group in this case is preferably a phenyl group or a naphthyl group and more preferably a phenyl group, because it does not hinder the light from the light source and the light emission of the light-emitting material. An increased number of aryl groups on the nitrogen atom causes concern about an increase in light absorption in the visible range, and among the three substituents on the nitrogen atom, the number of the aryl groups is preferably two or less and more preferably one or less. When at least one of the three substituents on the nitrogen atom is a substituted or unsubstituted alkyl group, the singlet oxygen can be trapped more efficiently, which is preferred. In particular, two or more of the three substituents are preferably substituted or unsubstituted alkyl groups.

Preferred examples of the tertiary amine include, but are not limited to, triethylamine, 1,4-diazabicyclo[2.2.2]octane, tri-n-butylamine, N,N-diethylaniline, and 2,2,6,6-tetramethylpiperidine.

The catechol derivatives refer to compounds having two or more hydroxy groups on a benzene ring including isomers such as resorcinol and hydroquinone. These compounds can trap the singlet oxygen more efficiently than phenol derivatives, in which one hydroxy group is on the benzene ring.

The substituent on the benzene ring is selected from hydrogen, an alkyl group, a cycloalkyl group, a heterocyclic group, an alkenyl group, a cycloalkenyl group, an alkynyl group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a boryl group, a phosphine oxide group, and a condensed ring and an aliphatic ring formed between adjacent substituents other than a hydroxy group. These substituents may be further substituted by the substituents described above.

Among them, preferred are a substituted or unsubstituted alkyl group, a substituted or unsubstituted cycloalkyl group, a substituted or unsubstituted aryl group, a substituted or unsubstituted heteroaryl group, or halogen in view of photostability, and more preferred are a substituted or unsubstituted alkyl group, a substituted or unsubstituted cycloalkyl group, a substituted or unsubstituted aryl group, or halogen. Furthermore, because of being less in discoloration after reaction with the singlet oxygen quencher, more preferred are a substituted or unsubstituted alkyl group, a substituted or unsubstituted cycloalkyl group, or halogen. Particularly preferred is a substituted or unsubstituted alkyl group.

As to the position of the hydroxy groups on the benzene ring, at least two hydroxy groups are preferably adjacent to each other. This is because the compound is more resistant to photooxidation than resorcinol (1,3-substituted) and hydroquinone (1,4-substituted). Also after being oxidized, light absorption in the visible range is small, and the discoloration of the composition can be prevented.

Preferred examples of the catechol derivatives include, but are not limited to, 4-tert-butylbenzene-1,2-diol and 3,5-di-tert-butylbenzene-1,2-diol.

The nickel compounds are compounds containing nickel; examples thereof include, but are not limited to, inorganic salts such as nickel chloride, complexes such as bis(acetylacetonate)nickel, and salts of organic acids such as nickel carbamate. The organic acids refer to organic compounds having a carboxy group, a sulfonyl group, a phenolic hydroxy group, or a thiol group. Among them, in view of uniformly being dispersed in the composition, preferred are complexes and salts of organic acids.

Examples of nickel complexes and nickel salts of organic acids suitably used as the singlet oxygen quencher include, but are not limited to, acetylacetonate-based nickel complexes, bisdithio-α-diketone-based nickel complexes, dithiolate-based nickel complexes, aminothiolate-based nickel complexes, thiocatechol-based nickel complexes, salicylaldehydeoxime-based nickel complexes, thiobisphenolate-based nickel complexes, indoaniline-based nickel compounds, carboxylic acid-based nickel salts, sulfonic acid-based nickel salts, phenol-based nickel salts, carbamic acid-based nickel salts, and dithiocarbamic acid-based nickel salts.

Among them, in view of the easiness of synthesis and being low in price, nickel salts of organic acids are preferred. Furthermore, because of being small in molar extinction coefficient in the visible range and not absorbing the light emission of the light source and the light-emitting material, sulfonic acid-based nickel salts are preferred. Furthermore, in view of exhibiting a better singlet oxygen quenching effect, nickel salts of aryl sulfonic acids are more preferred; in view of solubility to a wide range of solvents, nickel salts of alkyl sulfonic acids are preferred. The aryl group of the aryl sulfonic acids is preferably a substituted or unsubstituted phenyl group and more preferably a phenyl group substituted by an alkyl group in view of solubility and dispersibility to solvents.

For the lightfast stabilizers, compounds having a role as a radical quencher can also be suitably used. Preferred examples thereof include hindered amine-based compounds. Examples of the hindered amine-based compounds include piperidine derivatives such as 2,2,6,6-tetramethylpiperidine, 4-hydroxy-2,2,6,6-tetramethylpiperidine, 4-hydroxy-1,2,2,6,6-pentamethylpiperidine, 4-methoxy-2,2,6,6-tetramethylpiperidine, 4-methoxy-1,2,2,6,6-pentamethylpiperidine, bis(2,2,6,6-tetramethyl-4-piperidyl) sebacate, bis(1,2,2,6,6-pentamethyl-4-piperidyl) sebacate, 2,2,6,6-tetramethyl-4-piperidyl methacrylate, and 1,2,2,6,6-pentamethyl-4-piperidyl methacrylate and oxides thereof.

The content of these additives in the color conversion composition according to the embodiment of the present invention, which depends on the molar extinction coefficient, the fluorescence quantum yield, and the absorption intensity at an excitation wavelength of the compound and the thickness and the transmittance of a sheet to be prepared, is usually preferably $1.0 \times 10^{-3}$ part by weight or more, more preferably $1.0 \times 10^{-2}$ part by weight or more, and further preferably $1.0 \times 10^{-1}$ part by weight or more relative to 100 parts by weight of Component (B). The content of the additives is preferably 30 parts by weight or less, more preferably 15 parts by weight or less, and further preferably 10 parts by weight or less relative to 100 parts by weight of Component (B).

<Solvent>

The color conversion composition according to the embodiment of the present invention may contain a solvent. The solvent is not limited to a particular solvent so long as it can adjust the viscosity of a resin in a fluid state and does not have an excessive influence on the emission and durability of a light-emitting substance. Examples of the solvent include water, 2-propanol, ethanol, toluene, methyl ethyl ketone, methyl isobutyl ketone, cyclohexanone, hexane, acetone, terpineol, texanol, methyl cellosolve, butyl carbitol, butyl carbitol acetate, and propylene glycol monomethyl ether acetate. Two or more of these solvents can be contained in combination. Toluene among these solvents in particular is suitably contained in view of not having any influence on the degradation of the compound represented by General Formula (8) and giving a less amount of a residual solvent after being dried.

<Method for Manufacturing Color Conversion Composition>

The following describes an example of a method for manufacturing the color conversion composition according to the embodiment of the present invention. In this method of manufacture, certain amounts of the light-emitting material (Component (A)), the binder resin (Component (B)), and the solvent described above are mixed with each other. The components are mixed with each other so as to give a certain composition and are then uniformly mixed and dispersed by a stirring and kneading machine such as a homogenizer, a rotary-and-revolutionary stirring machine, a triple roll mill, a ball mill, a planetary ball mill, or a beads mill to obtain the color conversion composition. After being mixed and dispersed or during being mixed and dispersed, defoaming in a vacuum or under a reduced pressure is also preferably performed. In addition, a specific component may be mixed in advance, or treatment such as aging may be performed. A desired solid content can be obtained by removing the solvent by an evaporator.

<Method for Preparing Color Conversion Sheet>

In the present embodiment, the color conversion sheet is not limited in its structure so long as it includes a layer of the color conversion composition described above or a layer of its cured object. There are three representative structural examples of the color conversion sheet, for example.

FIG. 1 is a schematic sectional view of an example of the color conversion sheet according to the embodiment of the present invention. This color conversion sheet 1 exemplified in FIG. 1 is a laminate of a base layer 10 and a color conversion layer 11. This color conversion layer 11 is a layer containing the color conversion composition described above (a color conversion composition layer) and is preferably a layer obtained by curing the color conversion composition described above (a cured object layer). In this structural example of the color conversion sheet 1, the color conversion layer 11 is laminated on the base layer 10.

Figure 2:
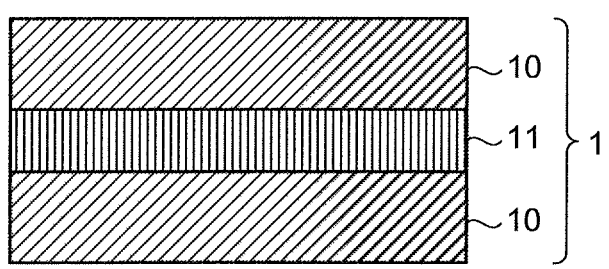
FIG. 2 is a schematic sectional view of another example of the color conversion sheet according to the embodiment of the present invention.

FIG. 2 is a schematic sectional view of another example of the color conversion sheet according to the embodiment of the present invention. The color conversion sheet 1 exemplified in FIG. 2 is a laminate of a plurality of base layers 10 and the color conversion layer 11. In this structural example of the color conversion sheet 1, the color conversion layer 11 is placed between the base layers 10.

Figure 3:
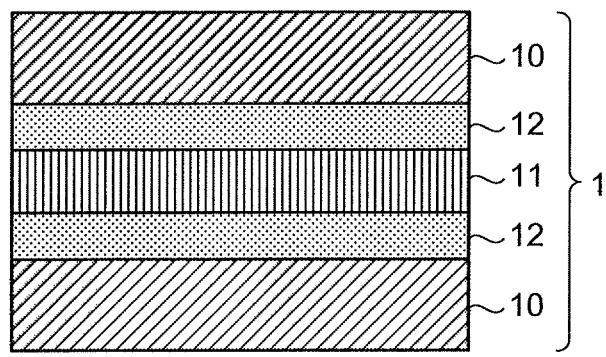
FIG. 3 is a schematic sectional view of still another example of the color conversion sheet according to the embodiment of the present invention.

FIG. 3 is a schematic sectional view of still another example of the color conversion sheet according to the embodiment of the present invention. The color conversion sheet 1 exemplified in FIG. 3 is a laminate of a plurality of base layers 10, the color conversion layer 11, and a plurality of barrier films 12. In this structural example of the color conversion sheet 1, the color conversion layer 11 is placed between the barrier films 12, and a laminate of the color conversion layer 11 and the barrier films 12 is further placed between the base layers 10. Thus, the color conversion sheet 1 may be provided with the barrier films 12 as exemplified in FIG. 3 in order to prevent the degradation of the color conversion layer 11 by oxygen, water, or heat.

(Base Layer)

For the base layer (the base layer 10 illustrated in FIGS. 1 to 3, for example), known metals, films, glasses, ceramics, papers, and the like can be used without any particular limitation. Specifically, examples of the base layer include metal plates and foils of aluminum (including aluminum alloys), zinc, copper, iron, and the like; films of plastics such as cellulose acetate, polyethylene terephthalate (PET), polyethylene, polyester, polyamide, polyimide, polyphenylene sulfide, polystyrene, polypropylene, polycarbonate, polyvinyl acetal, aramids, silicones, polyolefins, thermoplastic fluororesins, a copolymer of tetrafluoroethylene and ethylene (ETFE); films of plastics of α-polyolefin resins, polycaprolactone resins, acrylic resins, silicone resins, and copolymerized resins of theses resins and ethylene; papers laminated with the plastics and papers coated with the plastics; papers laminated or deposited with the metals; and plastic films laminated or deposited with the metals. When the base layer is a metal plate, the surface thereof may be subjected to chromium-based or nickel-based plating treatment or ceramic treatment.

Among these materials, in view of the easiness of preparing the color conversion sheet and the easiness of shaping the color conversion sheet, glasses and resin films are preferably used. To exclude the possibility of breakage or the like when a film-shaped base layer is handled, films having high strength are preferred. In view of those required characteristics and economy, resin films are preferred; among them, in view of economy and handleability, preferred are plastic films selected from the group consisting of PET, polyphenylene sulfide, polycarbonate, and polypropylene. When the color conversion sheet is dried or when the color conversion sheet is shaped under pressure at a high temperature of 200° C. or more by an extruder, a polyimide film is preferred in view of heat resistance. In view of the easiness of peeling off the sheet, the surface of the base layer may be subjected to mold releasing treatment in advance.

The thickness of the base layer is not limited to a particular thickness; the lower limit thereof is preferably 25 μm or more and more preferably 38 μm or more. The upper limit thereof is preferably 5,000 μm or less and more preferably 3,000 μm or less.

<Color Conversion Layer>

The following describes an example of a method for manufacturing the color conversion layer of the color conversion sheet according to the embodiment of the present invention. In this method for manufacturing the color conversion layer, the color conversion composition prepared by the method described above is applied to a substrate such as the base layer or a barrier film layer and is dried. The color conversion layer (the color conversion layer 11 illustrated in FIGS. 1 to 3, for example) is thus prepared. The application can be performed by a reverse roll coater, a blade coater, a slit die coater, a direct gravure coater, an offset gravure coater, a kiss coater, a natural roll coater, an air knife coater, a roll blade coater, a Vari-Bar roll blade coater, a two-stream coater, a rod coater, a wire bar coater, an applicator, a dip coater, a curtain coater, a spin coater, a knife coater, or the like. To obtain the uniformity of the film thickness of the color conversion layer, the application is preferably performed by a slit die coater.

The drying of the color conversion layer can be performed using a general heating apparatus such as a hot air drier or an infrared drier. For the heating of the color conversion sheet, a general heating apparatus such as a hot air drier or an infrared drier is used. In this case, heating condition include usually 1 minute to 5 hours at 40° C. to 250° C. and preferably 2 minutes to 4 hours at 60° C. to 200° C. Stepwise heating and curing such as step cure is also available.

After the color conversion layer is prepared, the base layer can be changed as needed. In this case, examples of a simple method include, but are not limited to, a method that performs the change using a hot plate and a method that uses a vacuum laminator or a dry film laminator.

The thickness of the color conversion layer, which is not limited to a particular thickness, is preferably 1 to 1,000 μm. If the thickness of the color conversion layer is smaller than 1 μm, the toughness of the color conversion sheet unfortunately reduces. If the thickness of the color conversion layer exceeds 1,000 μm, cracks are likely to occur, and the shaping of the color conversion sheet is difficult. The thickness of the color conversion layer is more preferably 5 to 100 μm or less.

In view of increasing the heat resistance of the color conversion sheet, the film thickness of the color conversion sheet is preferably 200 μm or less, more preferably 100 μm or less, and further preferably 50 μm or less.

The film thickness of the color conversion sheet in the present invention refers to a film thickness (an average film thickness) measured based on JIS K 7130 (1999) Plastics—Film and sheeting—Method A for measuring thickness by mechanical scanning in method for measuring thickness.

(Barrier Film)

The barrier film (the barrier film 12 illustrated in FIG. 3, for example) is included as appropriate when gas barrier property is increased for the color conversion layer, for example. Examples of this barrier film include metal oxide thin films and metal nitride thin films of inorganic oxides such as silicon oxide, aluminum oxide, titanium oxide, tantalum oxide, zinc oxide, tin oxide, indium oxide, yttrium oxide, and magnesium oxide, inorganic nitrides such as silicon nitride, aluminum nitride, titanium nitride, and silicon carbide nitride, mixtures thereof, and with other elements added thereto; and films formed of various kinds of resins such as polyvinyl chloride-based resins, acrylic-based resins, silicone-based resins, melamine-based resins, urethane-based resins, fluorine-based resins, and polyvinyl alcohol-based resins such as a saponified product of vinyl acetate.

Example of a barrier resin suitably used for the barrier film of the present invention include resins such as polyester, poly vinyl chloride, nylon, polyvinyl fluoride, polyvinylidene chloride, polyacrylonitrile, polyvinyl alcohol, and an ethylene-vinyl alcohol copolymer and mixtures of these resins. Among them, polyvinylidene chloride, polyacrylonitrile, an ethylene-vinyl alcohol copolymer, and polyvinyl alcohol are extremely small in oxygen permeability coefficient, and these resins are preferably contained. In view of resistance to discoloration, further preferably contained is polyvinylylidene chloride, polyvinyl alcohol, or an ethylene-vinyl alcohol copolymer; in view of being low in environmental loads, particularly preferably contained is polyvinyl alcohol or an ethylene-vinyl alcohol copolymer. These resins may be contained singly or mixed with different resins; in view of the uniformity of the barrier film and cost, a barrier film formed of a single resin is more preferred.

For polyvinyl alcohol, a saponified product of polyvinyl acetate in which the acetyl group is saponified in 98 mol % or more can be used, for example. For the ethylene-vinyl alcohol copolymer, a saponified product of an ethylene-vinyl alcohol copolymer with an ethylene content of 20 to 50% in which the acetyl group is saponified in 98 mol % or more can be used, for example.

Commercially available resins and films can also be used. Specific examples thereof include polyvinyl alcohol resin PVA117 manufactured by Kuraray Co., Ltd. and ethylene-vinyl alcohol copolymer ("EVAL" (registered trademark)) resins L171B and F171B and film EF-XL manufactured by Kuraray Co., Ltd.

To the barrier film, antioxidants, curing agents, cross-linking agents, processing-and-thermal stabilizers, lightfast stabilizers such as ultraviolet light absorbents, and the like may be added as needed to the extent that they do not have an excessive influence on the light emission and durability of the color conversion layer.

The thickness of the barrier film, which is not limited to a particular thickness, is preferably 100 μm or less in view of the flexibility of the entire color conversion sheet and cost. The thickness of the barrier film is more preferably 50 μm or less, further preferably 20 μm or less, particularly preferably 10 μm or less, and may be 1 μm or less. In view of the easiness of layer formation, the thickness of the barrier film is preferably 0.01 μm or more.

The barrier film may be provided on both faces of the color conversion layer 11 as in the barrier film 12 exemplified in FIG. 3 or provided on only one face of the color conversion layer 11. In accordance with functions required for the color conversion sheet, an auxiliary layer may be further provided having an anti-reflection function, an anti-glare function, an anti-reflection-and-anti-glare function, a hard coating function (an abrasion-resistant function), an antistatic function, a soil-resistant function, an electromagnetic shielding function, an infrared cutting function, an ultraviolet cutting function, a polarizing function, or a toning function.

<Adhesive Layer>

In the color conversion sheet according to the embodiment of the present invention, an adhesive layer may be provided between the layers as needed. For the adhesive layer, known materials can be used without particular limitation so long as they do not have an excessive influence on the light emission and durability of the color conversion sheet. When strong adhesion is required, preferably used are photocurable materials, thermocurable materials, anaerobic curable materials, and thermoplastic materials; among them, thermocurable materials are more preferred, and in particular, a material that is curable at 0° C. to 150° C. is preferred.

The thickness of the adhesive layer, which is not limited a particular thickness, is preferably 0.01 to 100 μm, more preferably 0.01 to 25 μm, further preferably 0.05 to 5 μm, and particularly preferably 0.05 to 1 μm.

<Excitation Light>

As to the type of the excitation light, any excitation light can be used so long as it exhibits light emission in a wavelength range that can be absorbed by the light-emitting substance to be mixed such as the compound represented by General Formula (8). Examples thereof include hot-cathode tubes, cold-cathode tubes, fluorescent light sources such as inorganic EL, organic electroluminescence element light sources, LED light sources, incandescent light sources, and sunlight; any of the excitation light can be used in principle. In particular, light from an LED light source is preferred excitation light. For display and lighting uses, further preferred excitation light is light from a blue LED light source having excitation light in the wavelength range of 400 to 500 nm in view of the capability of increasing the color purity of blue light. If the wavelength range of the excitation light is on the longer wavelength side thereof, the blue light is lacking, and white light cannot be formed; if the wavelength range of the excitation light is on the shorter wavelength side thereof, the light-emitting substance such as the compound represented by General Formula (8) or an organic compound such as the binder resin is likely to photodegrade, which are not preferred.

The excitation light may have one emission peak or have two or more emission peaks; to increase color purity, preferred is one having one emission peak. A plurality of excitation light sources having different emission peaks can be freely combined with each other.

<Light Source Unit>

The light source unit according to the embodiment of the present invention includes a light source and the color conversion composition or the color conversion sheet described above, when the color conversion composition is included, the arrangement of the light source and the color conversion composition is not limited to particular arrangement; the color conversion composition may be directly applied to the light source, or the color conversion composition may be applied to film or glass separate from the light source. When the color conversion sheet is included, the arrangement of the light source and the color conversion sheet is not limited to particular arrangement; the light source and the color conversion sheet may adhere closely to each other, or the remote phosphor method, in which the light source and the color conversion sheet are separate from each other, may be used. The light source unit may further include a color filter for the purpose of increasing color purity.

As described above, the excitation light in the wavelength range of 400 or more and 500 nm or less has relatively low excitation energy and can thus prevent the decomposition of the light-emitting substance such as the compound represented by General Formula (8). Consequently, the light source for use in the light source unit is preferably a light-emitting diode having its maximum emission in the wavelength range of 400 or more and 500 nm or less. The light source unit of the present invention can be used for displays, lighting, the interior design, signs, signboards, and the like, and is suitably used for displays and lighting in particular.

<Display and Lighting Apparatus>

The display according to the embodiment of the present invention includes the light source unit including the light source, the color conversion sheet, or the like as described above. For a display such as a liquid crystal display, for example, the light source unit described above is used as a backlight unit. The lighting apparatus according to the embodiment of the present invention includes the light source unit including the light source, the color conversion sheet, or the like as described above. This lighting apparatus is configured to emit white light by combining a blue LED light source as the light source unit and the color conversion composition or the color conversion sheet that converts blue light, from this blue LED light; source into light with a wavelength longer than the blue light with each other, for example.

<LED Chip and LED Package>

The color conversion sheet according to the embodiment of the present invention is preferably stuck to a light-emitting face of an LED chip of a general structure such as lateral, vertical, or flip chip type. With this structure, an LED chip with a color conversion sheet in which the color conversion sheet is laminated on the surface of the LED chip can be formed. The color conversion sheet can be suitably used in particular for a vertical or flip chip type LED chip having a large light-emitting area. The light-emitting face refers to a face through which light from the LED chip is extracted.

The light-emitting face from the LED chip may be a single plane or a non-single plane. Examples of the single plane include an LED chip having mainly only an upper light-emitting face. Specific examples thereof include vertical type LED chips and LED chips in which a side face is covered with a reflective layer to cause light to be extracted only from the upper face. Examples of the non-single plane include LED chips having an upper light-emitting face and a side light-emitting face and LED chips having a curved light-emitting face.

As to the LED chip, the light-emitting face is preferably the non-single plane, because light emission from the side can be used to achieve higher brightness. In particular, because a light-emitting area can be made larger, and a chip manufacturing process is simple, preferred is a flip chip type LED chip having an upper light-emitting face and a side light-emitting face. To improve light emission efficiency, in the LED chip, a light-emitting surface may be processed into a texture or the like based on optical design.

The color conversion sheet according to the embodiment of the present invention can also be stuck using an adhesive such as a transparent resin without being directly stuck to the LED chip. Covering the light-emitting face of the LED chip with the color conversion sheet can cause the light from the LED chip to directly enter the color conversion sheet as the color conversion layer without being lost by reflection and the like, which is preferred. With this structure, white light that has small variations in color, is high in efficiency, and is uniform can be obtained. The color conversion layer referred to here represents a layer that absorbs light emitted from the LED chip, performs wavelength conversion, and emits light with a wavelength different from that of the light of the LED chip.

The LED chip with the color conversion sheet obtained by these methods can be formed into an LED package packaged by performing metal wiring and sealing. This LED package is then incorporated into a module whereby the LED chip with the color conversion sheet according to the embodiment of the present invention can be suitably used for various LED light-emitting apparatuses including various kinds of lighting, liquid crystal backlight, and head lamps.

Figure 4A:
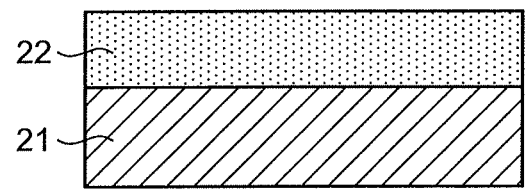
FIG. 4A is a diagram of an example of an LED chip with a color conversion sheet prepared with the color conversion sheet, according to the embodiment of the present invention.
Figure 4B:
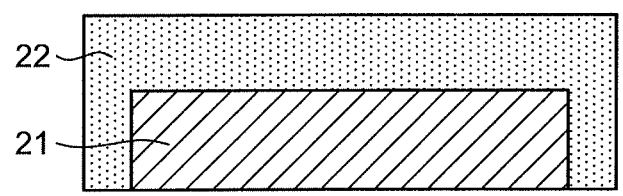
FIG. 4B is a diagram of another example of the LED chip with the color conversion sheet prepared with the color conversion sheet according to the embodiment of the present invention.
Figure 4C:
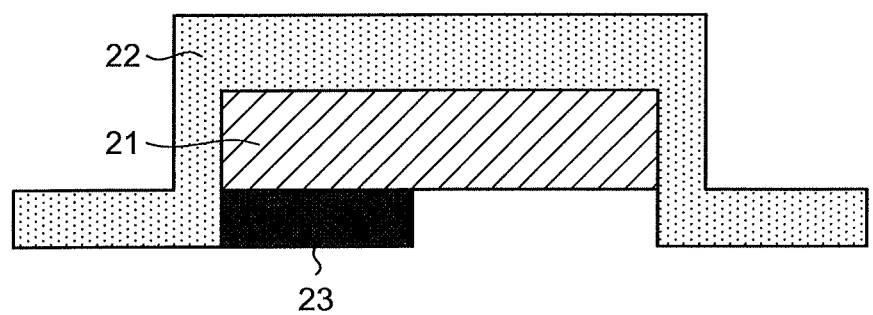
FIG. 4C is a diagram of still another example of the LED chip with the color conversion sheet prepared with the color conversion sheet according to the embodiment of the present invention.

FIG. 4A to FIG. 4C are diagrams of preferred examples of an LED chip with a color conversion sheet according to the embodiment of the present invention. FIG. 4A is a diagram of an example of the LED chip with the color conversion sheet prepared with the color conversion sheet according to the embodiment of the present invention. In this LED chip 21 with the color conversion sheet exemplified in FIG. 4A, a color conversion sheet 22 is stuck and placed on an upper face (a light-emitting face) of the LED chip 21. FIG. 4B is a diagram of another example of the LED chip with the color conversion sheet prepared with the color conversion sheet according to the embodiment of the present invention. In the LED chip 21 with the color conversion sheet exemplified in FIG. 4B, the color conversion sheet 22 is stuck and placed on not only the upper face (an upper light-emitting face) but also a side face (a side light-emitting face) of the LED chip 21. This type of LED chip 21 with the color conversion sheet can perform color conversion also on light emission from the side face of the LED chip 21, which is preferred. FIG. 4C is a diagram of still another example of the LED chip with the color conversion sheet prepared with the color conversion sheet according to the embodiment of the present invention. The LED chip 21 with the color conversion sheet exemplified in FIG. 4C is obtained by including the LED chip 21 of the flip chip type having an electrode 23 on its lower face and covering the upper face and the side face as the light-emitting faces of this LED chip 21 with the color conversion sheet 22.

Figure 5A:
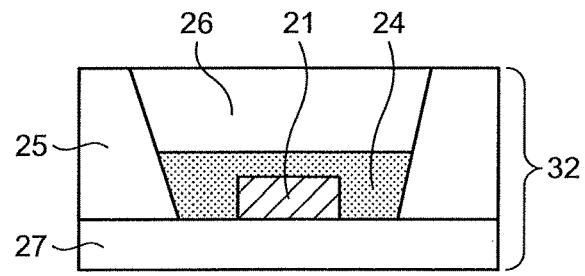
FIG. 5A is a diagram of an example of an LED package containing a color conversion composition according to the embodiment of the present invention.

FIG. 5A to FIG. 5J are diagrams of preferred examples of an LED package according to the embodiment of the present invention. FIG. 5A is a diagram of an example of the LED package containing the color conversion composition according to the embodiment of the present invention. This LED package 32 exemplified in FIG. 5A is obtained by injecting a color conversion composition 24 into a mounting substrate 27 with a reflector 25 on which the LED chip 21 is placed and then sealing this LED chip 21 with a transparent sealant 26. This LED package 32 is a preferred example including a cured object of the color conversion composition 24.

Figure 5B:
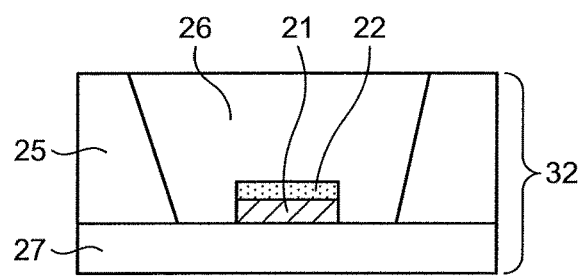
FIG. 5B is a diagram of Example 1 of the LED package including the color conversion sheet according to the embodiment of the present invention.
Figure 5C:
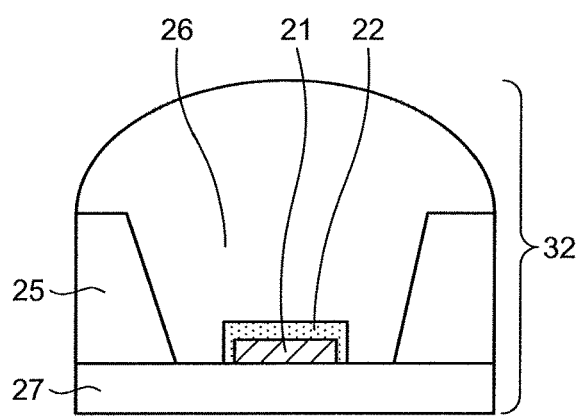
FIG. 5C is a diagram of Example 2 of the LED package including the color conversion sheet according to the embodiment of the present invention.

FIG. 5B is a diagram of Example 1 of the LED package including the color conversion sheet according to the embodiment of the present invention. The LED package 32 exemplified in FIG. 5B is obtained by sticking the color conversion sheet 22 on the LED chip 21 placed on the mounting substrate 27 with the reflector 25 and then sealing this LED chip 21 together with the color conversion sheet 22 with the transparent sealant 26. FIG. 5C is a diagram of Example 2 of the LED package including the color conversion sheet according to the embodiment of the present invention. The LED package 32 exemplified in FIG. 5C is obtained by sticking the color conversion sheet 22 on not only the upper face but also side face of the LED chip 21 placed on the mounting substrate 27 with the reflector 25 and further mounting a lens formed of the transparent sealant 26 thereon. This type of LED package 32 can perform color conversion by the color conversion sheet 22 also on light, emission from the side face of the LED chip 21, which is preferred.

Figure 5D:
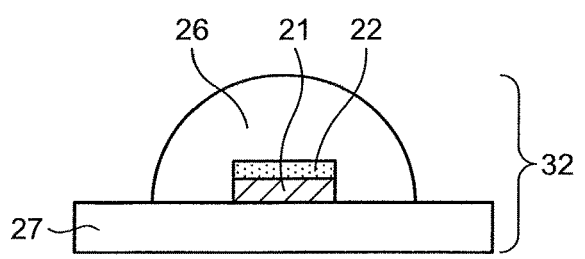
FIG. 5D is a diagram of Example 3 of the LED package including the color conversion sheet according to the embodiment of the present invention.
Figure 5E:
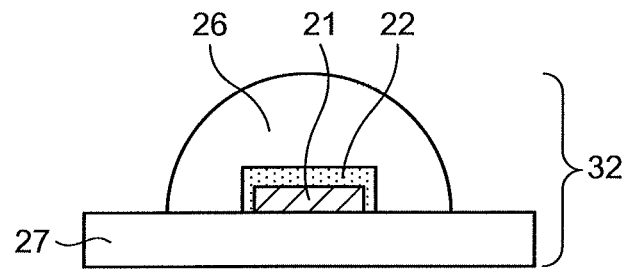
FIG. 5E is a diagram of Example 4 of the LED package including the color conversion sheet according to the embodiment of the present invention.

FIG. 5D is a diagram of Example 3 of the LED package including the color conversion sheet according to the embodiment of the present invention. The LED package 32 exemplified in FIG. 5D is obtained by sealing the LED chip 21 together with the color conversion sheet 22 with the lens formed body of the transparent sealant 26 without including the reflector 25. Except this point, the LED package 32 exemplified in FIG. 5D is similar to the LED package 32 exemplified in FIG. 5B. FIG. 5E is a diagram of Example 4 of the LED package including the color conversion sheet according to the embodiment of the present invention. The LED package 32 exemplified in FIG. 5E is similar to the LED package 32 exemplified in FIG. 5C except that the reflector 25 is not included.

Figure 5F:
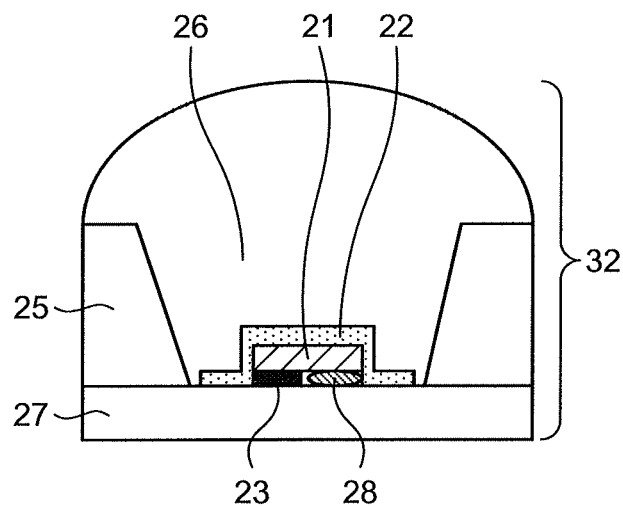
FIG. 5F is a diagram of Example 5 of the LED package including the color conversion sheet according to the embodiment of the present invention.
Figure 5G:
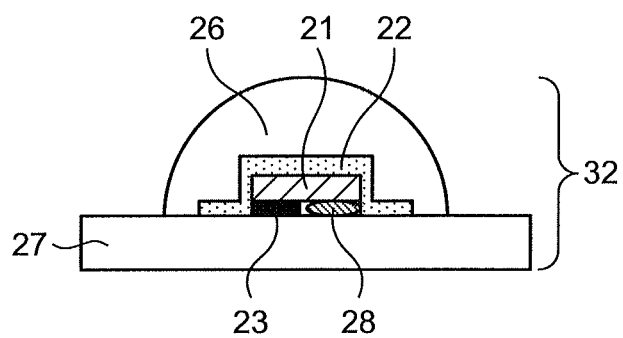
FIG. 5G is a diagram of Example 6 of the LED package including the color conversion sheet according to the embodiment of the present invention.

FIG. 5F is a diagram of Example 5 of the LED package including the color conversion sheet according to the embodiment of the present invention. The LED package 32 exemplified in FIG. 5F is obtained by including the LSD chip 21 of the flip chip type having the electrode 23 and a gold bump 28 on its lower face and covering the upper face and the side face as the light-emitting faces of this LED chip 21 with the color conversion sheet 22. Except this point, the LED package 32 exemplified in FIG. 5F is similar to the LED package 32 exemplified in FIG. 5C. When the side face of the LED chip 21 is covered with the color conversion sheet 22, the color conversion sheet 22 may reach the upper face of the mounting substrate 27 as illustrated in FIG. 5F. FIG. 5G is a diagram of Example 6 of the LED package including the color conversion sheet according to the embodiment of the present invention. The LED package 32 exemplified in FIG. 5G is obtained by sealing the LED chip 21 of the flip chip type (refer to FIG. 5F) together with the color conversion sheet 22 with the lens formed body of the transparent sealant 26 without including the reflector 25. Except this point, the LED package 32 exemplified in FIG. 5G is similar to the LSD package 32 exemplified in FIG. 5E.

Figure 5H:
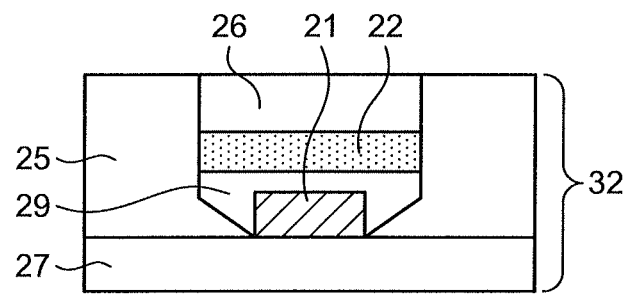
FIG. 5H is a diagram of Example 7 of the LED package including the color conversion sheet according to the embodiment of the present invention.
Figure 5I:
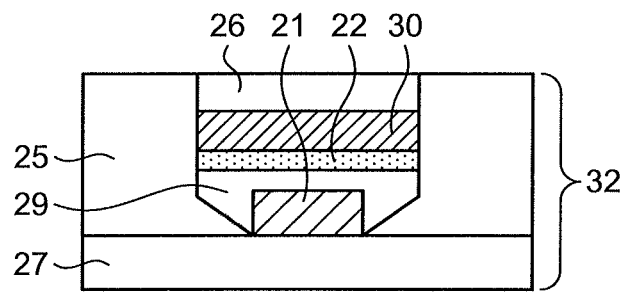
FIG. 5I is a diagram of Example 8 of the LED package including the color conversion sheet according to the embodiment of the present invention.

FIG. 5H is a diagram of Example 7 of the LED package including the color conversion sheet according to the embodiment of the present invention. The LED package 32 exemplified in FIG. 5H is obtained by sticking the LED chip 21 and the color conversion sheet 22 to each other with a transparent adhesive 29. Except this point, the LED package 32 exemplified in FIG. 5B is similar to the LED package 32 exemplified in FIG. 5B. FIG. 5I is a diagram of Example 8 of the LED package including the color conversion sheet according to the embodiment of the present invention. The LED package 32 exemplified in FIG. 5I includes the color conversion sheet 22 with a base 30 prepared in advance. This type of LED package 32 is used without separating the base 30 from the color conversion sheet 22. Except this point, the LED package 32 exemplified in FIG. 5I is similar to the LED package 32 exemplified in FIG. 5H. The material of the base 30 is preferably glass. The LED packages 32 exemplified in FIG. 5B to FIG. 5I are preferred examples including the color conversion sheet 22 or a cured object thereof.

Figure 5J:
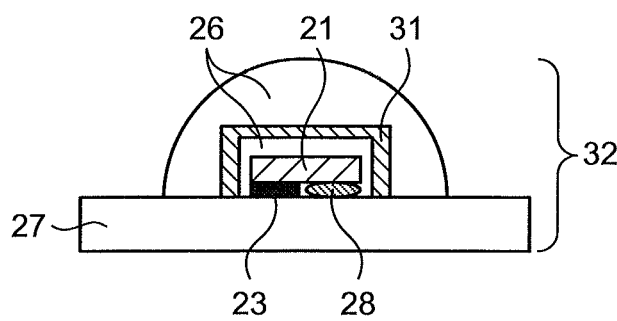
FIG. 5J is a diagram of an example of the LED package including a formed object prepared with the color conversion composition according to the embodiment of the present invention.

FIG. 5J is a diagram of an example of the LED package including a formed object prepared with the color conversion composition according to the embodiment of the present invention. The LED package 32 exemplified in FIG. 5J is obtained by including the LED chip 21 of the flip chip type (refer to FIG. 5F), covering the upper face and the side as the light-emitting faces of this LED chip 21 with the transparent sealant 26, and further covering this transparent sealant 26 with a formed object 31 containing the color conversion composition. Except this point, the LED package 32 exemplified in FIG. 5J is similar to the LED package 32 exemplified in FIG. 5G. This LED package 32 is a preferred example including the formed object 31 containing the color conversion composition 24 or a cured object thereof.

The LED package to which the present invention can be applied is not limited to these examples. In the LED package 32 illustrated in FIG. 5B, for example, the transparent sealant 26 may have a shape as illustrated in FIG. 5C, and the color conversion sheet 22 may be stuck to not only the upper face but also the side face of the LED chip 21. Thus, the structures of the respective parts of the LED packages 32 exemplified in FIG. 5A to 5J can be combined with each other as appropriate. The parts of the LED package 32 may be replaced with known parts other than those or combined with each other.

For the transparent sealant 26, known materials can be used so long as they are excellent in shaping processability, transparency, heat resistance, adhesiveness, and the like; examples thereof include epoxy resins, silicone resins (including organopolysiloxane cured objects (cross-linked objects) such as silicone rubbers and silicone gels), urea resins, fluorine resins, and polycarbonate resins. For the transparent adhesive 29, the transparent sealant 26 described above may be used.

The LED package of the present invention can be used for displays, lighting, the interior design, signs, signboards, and the like, and is suitably used for displays and lighting in particular. The display of the present invention includes a backlight unit including the LED package described above, for example. The lighting apparatus of the present invention includes the LED package described above.

EXAMPLES

The following describes the present invention with reference to examples; these examples do not limit the present invention. In the following examples and comparative examples. Compounds G-1 to G-5 and R-1 to R-4 are compounds shown below.

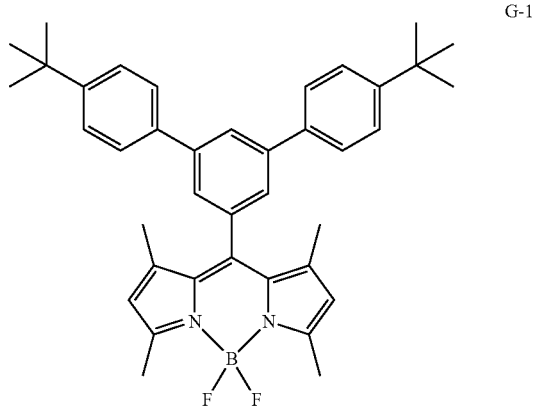

G-1

G-2
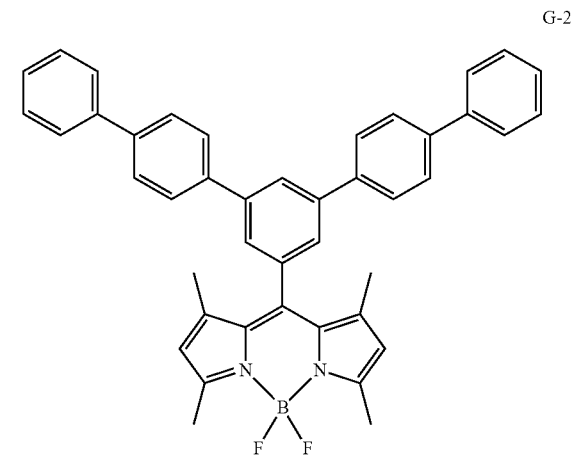
G-3
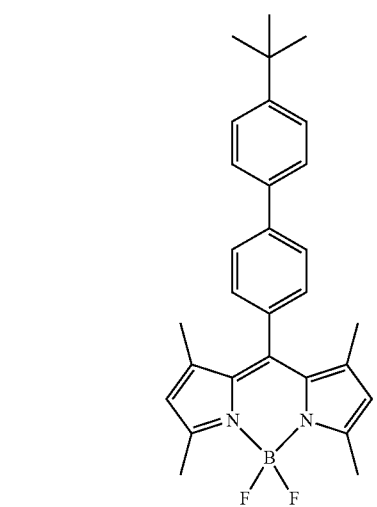
G-4
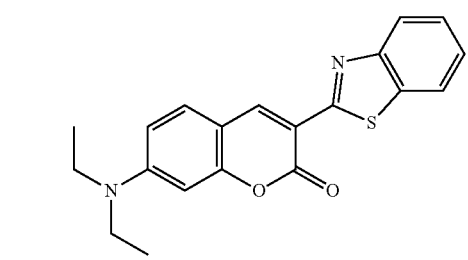
G-5
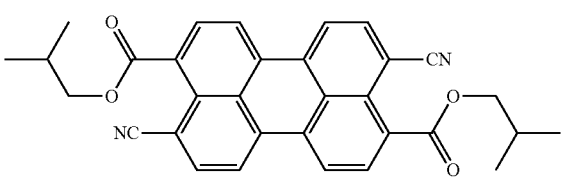
R-1
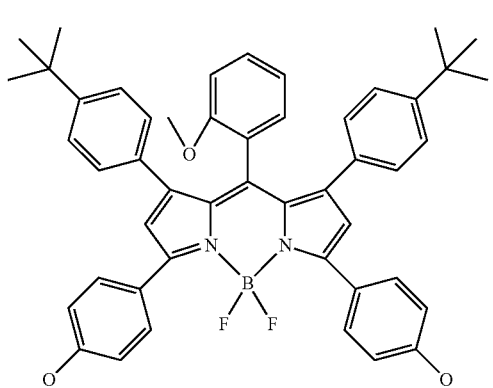
R-2
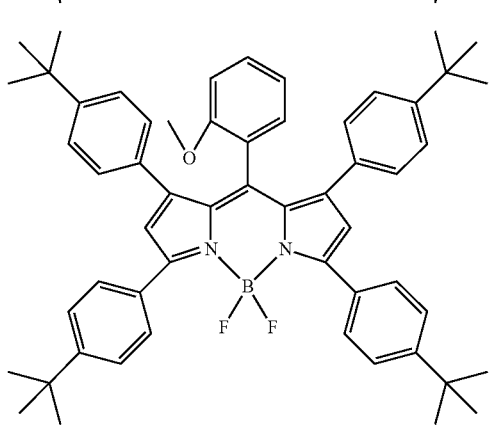
R-3
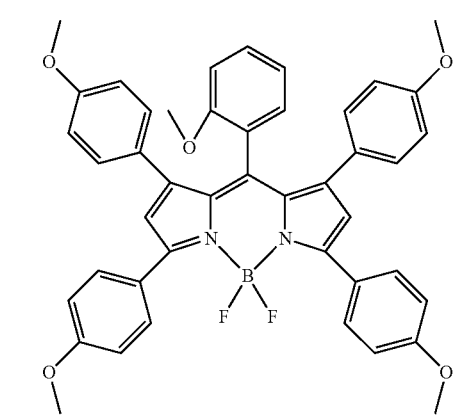
R-4
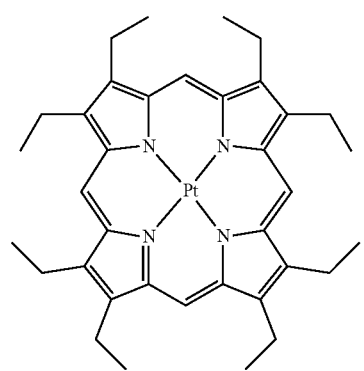
In polyester resins of the following examples and comparative examples, the used resins were synthesized by a known esterification reaction. Table 2 below lists the values of Y and $n_1$, $n_2$, $m_1$, $m_2$, $m_3$, $m_4$, and $m_5$, the molecular weight, and the adhesive strength with the base layer of the used resins. The values of $m_1$, $m_2$, $m_3$, $m_4$, and $m_5$ were obtained as the weight ratios of the respective partial structures by performing $^1$H-NMR measurement and determining the component composition of the resin by its integral ratio.

In resins containing a bisphenol structure of the following examples, the used resins were bisphenol A type epoxy resin "YP-50" (manufactured by Nippon Steel & Sumikin Chemical Co., Ltd., weight average molecular weight: 80,000) and bisphenol A/bisphenol F copolymerization type epoxy resin "YP-70" (manufactured by Nippon Steel & Sumikin Chemical Co., Ltd., weight, average molecular weight: 55,000). In the following, "YP-50" is denoted by Bisphenol Resin F11, whereas "YP-70" is denoted by Bisphenol Resin F12. In the following comparative examples, Acrylic Resins F21 and F22 listed in Table 2 are used as appropriate.

The adhesive strength between the resin and the base layer was carried out in accordance with the cross-cut method in JIS K5600-5-6 (1999). Specifically, on a coating (10 μm) formed by applying a resin liquid to the surface of a base layer (PET) and drying the resin liquid at temperature of 100° C. for 1 hour, six cuts each were made longitudinally and latitudinally at intervals of 2 mm to form 25 squares, and cellophane adhesive tape was stuck thereto from above and was then peeled off. The number of squares remaining on the base layer was determined. Evaluation criteria are as follows: "A" means that "20 or more squares per the 25 squares remained." "B" means that "15 or more and less than 20 squares per the 25 squares remained." "C" means that less than 15 squares per the 25 squares remained."

<Measurement of Color Conversion Characteristics>

A current of 10 mA was passed through a light-emitting apparatus having each of the color conversion sheets and a blue LSD element (manufactured by ProLight; type PM2B-3LBE-SD, emission peak wavelength: 460 nm) to light an LED chip, and an emission spectrum, emission intensity at a peak wavelength, and chromaticity were measured using a spectral radiance meter (CS-1000 manufactured by Konica Minolta, Inc.). The distance between each of the color conversion sheets and the blue LED element was set to 3 cm.

<Test of Lightfastness>

A current of 10 mA was passed through a light-emitting apparatus having each of the color conversion sheets and a blue LED element (manufactured by ProLight; type PM2B-3LBE-SD, emission peak wavelength: 460 nm) to light an LED chip, and initial luminance was measured using a spectral radiance meter (CS-1000 manufactured by Konica Minolta, Inc.). The distance between each of the color conversion sheets and the blue LED element was set to 3 cm. After that, each of the color conversion sheets was continuously irradiated with the light from the blue LED element at room temperature, and the time elapsed until the luminance decreased by a predetermined amount was observed to evaluate lightfastness.

Synthesis Example 1

The following describes a method for synthesizing Compound G-1 of Synthesis Example 1 of the present invention. In the method for synthesizing Compound G-1, 3,5-dibromobenzaldehyde (3.0 g), 4-t-butylphenylboronic acid (5.3 g), tetrakis(triphenylphosphine)palladium (0) (0.4 g), and

TABLE 2

| Binder resin | Polyester Resin F1 | Polyester Resin F2 | Polyester Resin F3 | Polyester Resin F4 | Polyester Resin F5 | Bisphenol Resin F11 | Bisphenol Resin F12 | Acrylic Resin F21 | Acrylic Resin F22 |
|---|---|---|---|---|---|---|---|---|---|
| Y | Neopentyl | Neopentyl | Neopentyl | Neopentyl | — | — | — | — | — |
| $n_1$ | 2 | 2 | 2 | 2 | 2 | — | — | — | — |
| $n_2$ | — | 8 | 8 | 8 | 8 | — | — | — | — |
| $m_1$ | 24 | 21 | 23 | 21 | 0 | — | — | — | — |
| $m_2$ | 31 | 39 | 30 | 20 | 0 | — | — | — | — |
| $m_3$ | 31 | 12 | 12 | 0 | 12 | — | — | — | — |
| $m_4$ | 14 | 16 | 13 | 13 | 27 | — | — | — | — |
| $m_5$ | 0 | 12 | 22 | 46 | 61 | — | — | — | — |
| Molecular weight | 22000 | 16000 | 23000 | 28000 | 1000 | 80000 | 55000 | 100000 | 30000 |
| Adhesive strength | A | A | A | B | C | A | A | C | C |

The following describes methods of evaluation about structural analysis in the examples and the comparative examples.

<Measurement of $^1$H-NMR>

$^1$H-NMR on the compounds was measured with a deuteriochloroform solution using Superconducting FTNMR EX-270 (manufactured by JEOL Ltd.).

<Measurement of Absorption Spectrum>

Absorption spectra of the compounds were measured with the compounds dissolved in toluene at a concentration of $1 \times 10^{-6}$ mol/L using U-3200 type spectrophotometer (manufactured by Hitachi, Ltd.).

<Measurement of Fluorescence Spectrum>

For fluorescence spectra of the compounds, fluorescence spectra when the compounds were dissolved in toluene at a concentration of $1 \times 10^{-6}$ mol/L and were excited at a wavelength of 460 nm were measured using F-2500 type fluorescence spectrophotometer (manufactured by Hitachi, Ltd.).

potassium carbonate (2.0 g) were put into a flask, and purged with nitrogen. Degassed toluene (30 ml) and degassed water (10 ml) were added thereto, and the resultant mixture was refluxed for 4 hours. This reaction solution was cooled to room temperature, and the organic layer was separated and was then washed with a saturated saline solution. This organic layer was dried with magnesium sulfate and was filtered, and the solvent was then distilled off therefrom. The obtained reaction product was purified by silica gel chromatography to obtain 3,5-bis(4-t-butylphenyl)benzaldehyde (3.5 g) as a white solid.

Next, 3,5-bis(4-t-butylphenyl)benzaldehyde (1.5 g) and 2,4-dimethylpyrrole (0.7 g) were put into a reaction solution, and dehydrated dichloromethane (200 ml) and trifluoroacetic acid (one drop) were added thereto, and the resultant mixture was stirred for 4 hours in a nitrogen atmosphere. Subsequently, a dehydrated dichloromethane solution of 2,3-dichloro-5,6-dicyano-1,4-benzoquinone (0.85 g) was added thereto, and the resultant mixture was stirred for additional 1 hour. After completion of reaction, a boron trifluoride diethyl ether complex (7.0 ml) and diisopropylethylamine (7.0 ml) were added thereto, and the resultant mixture was stirred for 4 hours. Water (100 ml) was then further added thereto, the resultant mixture was stirred, and the organic layer was separated. This organic layer was dried with magnesium sulfate and was filtered, and the solvent was then distilled off therefrom. The obtained reaction product was purified by silica gel chromatography to obtain a compound (0.4 g) (yield: 18%). A $^1$H-NMR analysis result of this obtained compound is as follows, by which it was confirmed that this compound was Compound G-1.

$^1$H-NMR (CDCl$_3$ (d=ppm)): 7.95 (s, 1H), 7.63-7.48 (m, 10H), 6.00 (s, 2H), 2.58 (s, 6H), 1.50 (s, 6H), 1.37 (s, 18H).

Figure 6:
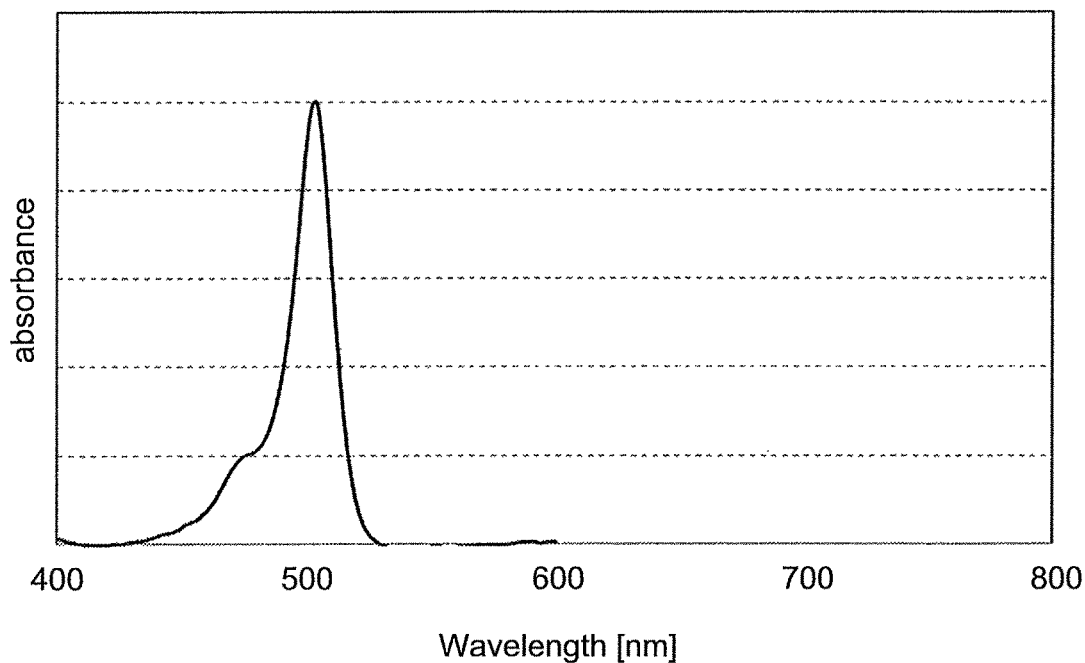
FIG. 6 is a diagram exemplifying an absorption spectrum of a compound of Synthesis Example 1 in examples of the present invention.
Figure 7:
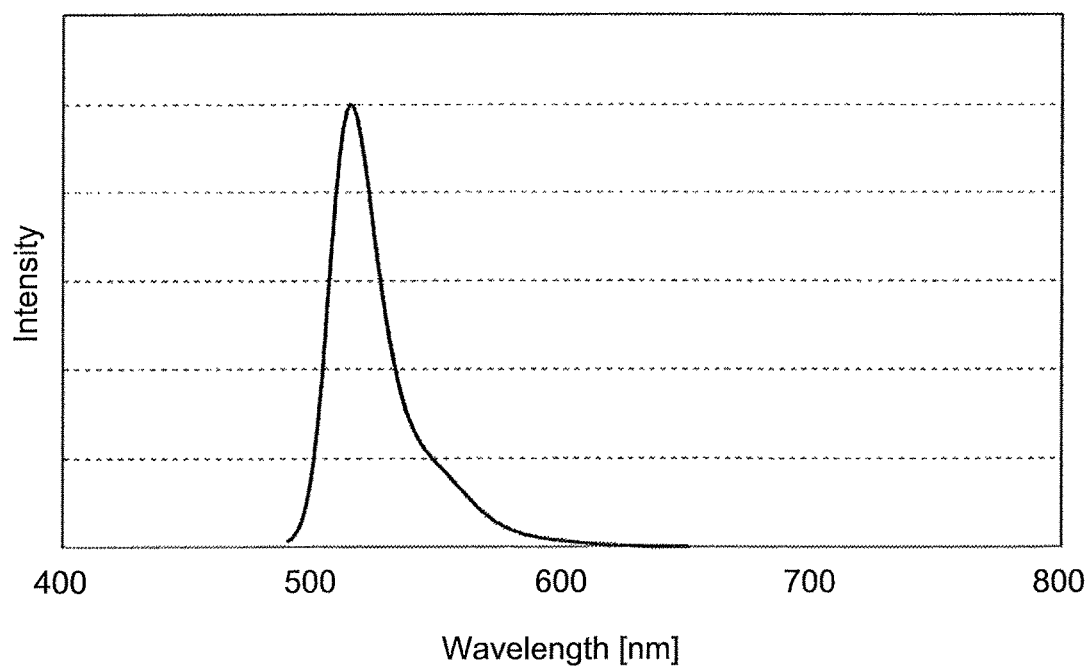
FIG. 7 is a diagram exemplifying an emission spectrum of the compound of Synthesis Example 1 in the examples of the present invention.

An absorption spectrum of this compound G-1 is as illustrated in FIG. 6, which showed light absorption characteristics against a blue excitation light source (460 nm). A fluorescence spectrum of this compound G-1 is as illustrated in FIG. 7, which showed a sharp emission peak in the green region. Showing a fluorescence quantum yield of 83%, this Compound G-1 was a compound that enabled efficient color conversion.

Synthesis Example 2

The following describes a method for synthesizing Compound R-1 of Synthesis Example 2 of the present invention. In the method for synthesizing Compound R-1, a mixed solution of 4-(4-t-butylphenyl)-2-(4-methoxyphenyl)pyrrole (300 mg), 2-methoxybenzoyl chloride (201 mg), and toluene (10 ml) was heated at 120° C. for 6 hours in a nitrogen flow. This heated solution was cooled to room temperature and was then evaporated. Next, the resultant concentrate was washed with ethanol (20 ml) and was dried in a vacuum to obtain 2-(2-methoxybenzoyl)-3-(4-t-butylphenyl)-5-(4-methoxyphenyl)pyrrole (260 mg).

Next, a mixed solution of 2-(2-methoxybenzoyl)-3-(4-t-butylphenyl)-5-(4-methoxyphenyl)pyrrole (260 mg), 4-(4-t-butylphenyl)-2-(4-methoxyphenyl)pyrrole (180 mg), methanesulfonic acid anhydride (206 mg), and degassed toluene (10 ml) was heated at 125° C. for 7 hours in a nitrogen flow. This heated solution was cooled to room temperature, water (20 ml) was then injected thereto, and extraction was performed with dichloromethane (30 ml). The organic layer was washed with water (20 ml) twice and was evaporated, and the resultant concentrate was dried in a vacuum.

Next, to a mixed solution of the obtained pyrromethene body and toluene (10 ml) in a nitrogen stream, diisopropylethylamine (305 mg) and a boron trifluoride diethyl ether complex (670 mg) were added, and the resultant mixture was stirred at room temperature for 3 hours. Water (20 ml) was then injected thereinto, and extraction was performed with dichloromethane (30 ml). The organic layer was washed with water (20 ml) twice, was dried with magnesium sulfate, and was evaporated. The resultant concentrate was purified by silica gel chromatography and was dried in a vacuum to obtain reddish-violet powder (0.27 g). A $^1$H-NMR analysis result of the obtained powder is as follows, by which it was confirmed that the reddish-violet powder obtained above was Compound R-1.

$^1$H-NMR (CDCl$_3$, ppm): 1.19 (s, 18H), 3.42 (s, 3H), 3.85 (s, 6H), 5.72 (d, 1H), 6.20 (t, 1H), 6.42-6.97 (m, 16H), 7.89 (d, 4H).

Figure 8:
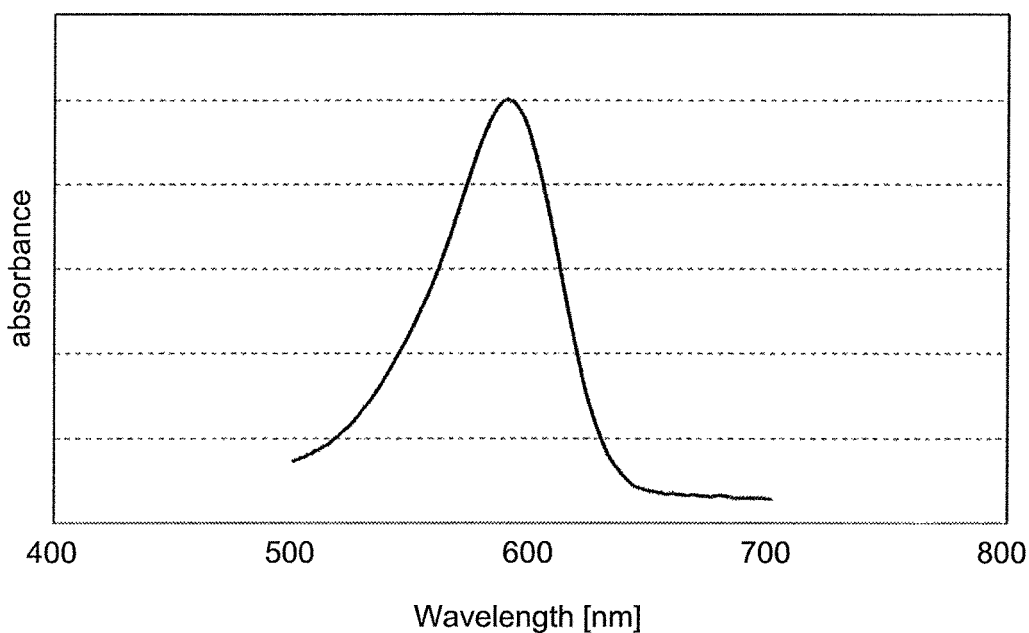
FIG. 8 is a diagram exemplifying an absorption spectrum of a compound of Synthesis Example 2 in the example of the present invention.
Figure 9:
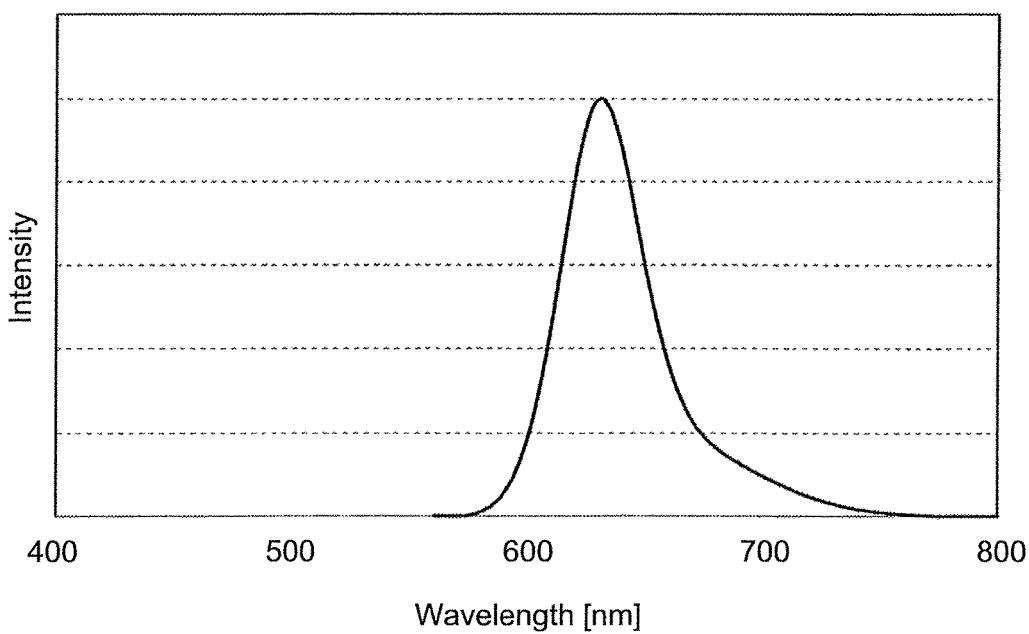
FIG. 9 is a diagram exemplifying an emission spectrum of the compound of Synthesis Example 2 in the examples of the present invention.

An absorption spectrum of this compound R-1 is as illustrated in FIG. 8, which showed light absorption characteristics against blue and green excitation light sources. A fluorescence spectrum of this compound G-1 is as illustrated in FIG. 9, which showed a sharp emission peak in the red region. Showing a fluorescence quantum yield of 90%, this Compound R-1 was a compound that enabled efficient color conversion.

Example 1

In Example 1 of the present invention/using Polyester Resin F1 (refer to Table 2) as Component (B), 0.20 part by weight of Compound G-1 as Component (A) and 300 parts by weight of toluene as a solvent were mixed with 100 parts by weight of Component (B), and the resultant mixture was then stirred and defoamed at 300 rpm for 20 minutes using a planetary stirring and defoaming apparatus "Mazerustar KK-400" (manufactured by Kurabo Industries Ltd.) to obtain a color conversion composition as a resin liquid for sheet preparation.

Next, the resin liquid for sheet preparation was applied to "Lumirror" U48 (manufactured by Toray Industries, Inc., thickness: 50 μm) using a slit die coater and was heated and dried at 100° C. for 1 hour to form a color conversion layer with an average film thickness of 10 μm. Next, "Lumirror" U48 (thickness: 50 μm) was laminated by heating on the color conversion layer to prepare a color conversion sheet with a structure similar to that of the color conversion sheet 1 illustrated in FIG. 2.

Blue LED light was subjected to color conversion using this color conversion sheet; when only the emission region of green light was extracted, high color purity green emission with a peak wavelength of 530 nm and with a full width at half maximum of an emission spectrum at the peak wavelength being 26 nm was obtained. When the color conversion sheet was continuously irradiated with the light from the blue LED element at room temperature, the time elapsed until the luminance decreased by 5% was 320 hours. An evaluation result of Example 1 is listed in Table 3 below.

Examples 2 to 8 and Comparative Examples 1 to 6

In Examples 2 to 8 of the present invention and Comparative Examples 1 to 6 against the present invention, color conversion sheets were prepared and evaluated similarly to Example 1 except that light-emitting materials (Compounds G-1, G-2, G-3, G-4, and G-5) listed in Table 3 were used as Component (A), and resins (Polyester Resins F1, F2, F3, F4, and F5 and Acrylic Resin F21) listed in Table 3 were used as Component (B). Evaluation results of Examples 2 to 3 and Comparative Examples 1 to 6 are listed in Table 3.

Example 9

In Example 9 of the present invention, a color conversion sheet was prepared and evaluated similarly to Example 1 except that a resin (a 1:1 mixture of Polyester Resin F1 and Polyester Resin F3) listed in Table 3 was used as Component (B). An evaluation result of Example 9 is listed in Table 3.

Example 10

In Example 10 of the present invention, using Polyester Resin F1 (refer to Table 2) as Component (B), 0.08 part by weight of Compound R-1 as Component (A) and 300 parts by weight of toluene as a solvent were mixed with 100 parts by weight of Component (B), and the resultant mixture was stirred and defoamed at 300 rpm for 20 minutes using a planetary stirring and defoaming apparatus "Mazerustar KK-400" (manufactured by Kurabe Industries Ltd.) to obtain a color conversion composition as a resin liquid for sheet preparation.

Next, the resin liquid for sheet preparation was applied to "Lumirror" U48 (manufactured by Toray Industries, Inc., thickness: 50 μm) using a slit die coater and was heated and dried at 100° C. for 1 hour to form a color conversion layer with an average film thickness of 10 μm. Next, "Lumirror" U48 (thickness: 50 μm) was laminated by heating on the color conversion layer to prepare a color conversion sheet with a structure similar to that of the color conversion sheet 1 illustrated in FIG. 2.

Blue LED light was subjected to color conversion using this color conversion sheet; when only the emission region of red light was extracted, high color purity red emission with a peak wavelength of 635 nm and with a full width at half maximum of an emission spectrum at the peak wavelength being 49 nm was obtained. When the color conversion sheet was continuously irradiated with the light from the blue LED element at room temperature, the time elapsed until the luminance decreased by 2% was 340 hours. An evaluation result of Example 10 is listed in Table 4 below.

Examples 11 to 16 and Comparative Examples 7 to 11

In Examples 11 to 16 of the present invention and Comparative Examples 7 to 11 against the present invention, color conversion sheets were prepared and evaluated similarly to Example 10 except that light-emitting materials (Compounds R-2, R-2, R-3, and R-4) listed in Table 4 were used as Component (A), and resins (Polyester Resins F1, F2, F3, F4, and F5 and Acrylic Resin F21) listed in Table 4 were used as Component (B). Evaluation results of Examples 11 to 16 and Comparative Examples 7 to 11 are listed in Table 4.

Example 17

In Example 17 of the present invention, a color conversion sheet was prepared and evaluated similarly to Example 10 except that a resin (a 1:1 mixture of Polyester Resin F1 and Polyester Resin F3) listed in Table 4 was used as Component (B). An evaluation result of Example 17 is listed in Table 4.

Example 18

In Example 18 of the present invention, using Polyester Resin 1 (refer to Table 2) as Component (B), 0.20 part by weight of Compound G-1 as Light-Emitting Material (a) of Component (A), 0.08 part by weight of Compound R-1 as Light-Emitting Material (b) of Component (A), and 300 parts by weight of toluene as a solvent were mixed with 100 parts by weight of Component (B), and the resultant mixture was stirred and defoamed at 300 rpm for 20 minutes using a planetary stirring and defoaming apparatus "Mazerustar KK-400" (manufactured by Kurabo Industries Ltd.) to obtain a color conversion composition as a resin liquid for sheet preparation.

Next, the resin liquid for sheet, preparation was applied to "Lumirror" U48 (manufactured by Toray Industries, Inc., thickness: 50 μm) using a slit die coater and was heated and dried at 100° C. for 1 hour to form a color conversion layer with an average film thickness of 10 μm. Next, "Lumirror" U48 (thickness: 50 μm) was laminated by heating on the color conversion layer to prepare color conversion sheet with a structure similar to that of the color conversion sheet 1 illustrated in FIG. 2.

Blue LED light was subjected to color conversion using this color conversion sheet; when only the emission region of green light was extracted, high color purity green emission with a peak wavelength of 530 nm and with a full width at half maximum of an emission spectrum at the peak wavelength being 28 nm was obtained; when only the emission region of red light was extracted, high color purity red emission with a peak wavelength of 635 nm and with a full width at half maximum of an emission spectrum at the peak wavelength being 49 nm was obtained. When the color conversion sheet was continuously irradiated with the light from the blue LED element at room temperature, the time elapsed until the luminance decreased by 5% was 330 hours. An evaluation result of Example 18 is listed in Table 5 below.

Examples 19 to 26 and Comparative Examples 12 to 18

In Examples 19 to 26 of the present invention and Comparative Examples 12 to 18 against the present invention, color conversion sheets were prepared and evaluated similarly to Example 18 except that Light-Emitting Material (a) (Compounds G-1, G-2, G-3, and G-4) and Light-Emitting Material (b) (Compounds R-1, R-2, and R-3) listed in Table 5 were used as Component (A), and resins (Polyester Resins F1, F2, F3, F4, and F5 and Acrylic Resin F21) listed in Table 5 were used as Component (B). Evaluation results of Examples 19 to 26 and Comparative Examples 12 to 18 are listed in Table 5.

Example 27

In Example 27 of the present invention, a color conversion sheet was prepared and evaluated similarly to Example 18 except that a resin (a 1:1 mixture of Polyester Resin F1 and Polyester Resin F3) listed in Table 5 was used as Component (B). An evaluation result of Example 27 is listed in Table 5.

Example 28

In Example 28 of the present invention, using Bisphenol Resin F11 (refer to Table 2) as Component (B), 0.20 part by weight of Compound G-1 as Component (A) and 200 parts by weight of methyl ethyl ketone as a solvent were mixed with 100 parts by weight of Component (3), and the resultant mixture was stirred and defoamed at 300 rpm for 20 minutes using a planetary stirring and defoaming apparatus "Mazerustar KK-400" (manufactured by Kurabo Industries Ltd.) to obtain a color conversion composition as a resin liquid for sheet preparation.

Next, the resin liquid for sheet preparation was applied to "Lumirror" U40 (manufactured by Toray Industries, Inc., thickness: 50 μm) using a slit die coater and was heated and dried at 100° C. for 1 hour to form a color conversion layer with an average film thickness of 10 μm. Next, "Lumirror" U40 (thickness: 50 μm) was overlaid on the color conversion layer and was laminated by heating at 90° C. in a vacuum condition to prepare a color conversion sheet with a structure similar to that of the color conversion sheet 1 illustrated in FIG. 2.

Blue LED light was subjected to color conversion using this color conversion sheet; when only the emission region of green light was extracted, high color purity green emission with a peak wavelength of 526 nm and with a full width at half maximum of an emission spectrum at the peak wavelength being 25 nm was obtained. When the color conversion sheet was continuously irradiated with the light from the blue LED element at room temperature, the time elapsed until the luminance decreased by 5% was 210 hours. An evaluation result of Example 28 is listed in Table 6 below.

Examples 29 to 37 and Comparative Examples 19 to 23

In Examples 29 to 37 of the present invention and Comparative Examples 19 to 23 against the present invention, color conversion sheets were prepared and evaluated similarly to Example 28 except that light-emitting materials (Compounds G-1, G-2, G-3, G-4, and G-5) listed in Table 6 were used as Component (A), and resins (Bisphenol Resins F11 and F12 and Acrylic Resin F22) listed in Table 6 were used as Component (B). Evaluation results of Examples 29 to 37 and Comparative Examples 19 to 23 are listed in Table 6.

Example 38

In Example 38 of the present invention, a color conversion sheet was prepared and evaluated similarly to Example 28 except that a resin (a 1:1 mixture of Bisphenol Resin F11 and Polyester Resin F1) listed in Table 6 was used as Component (B). An evaluation result of Example 38 is listed in Table 6.

Example 39

In Example 39 of the present invention, using Bisphenol Resin F11 (refer to Table 2) as Component (B), 0.08 part by weight of Compound R-1 as Component (A) and 200 parts by weight of methyl ethyl ketone as a solvent were mixed with 100 parts by weight of Component. (B), and the resultant mixture was stirred and defoamed at 300 rpm for 20 minutes using a planetary stirring and defoaming apparatus "Mazerustar KK-400" (manufactured by Kurabo Industries Ltd.) to obtain a color conversion composition as a resin liquid for sheet preparation.

Next, the resin liquid for sheet preparation was applied to "Lumirror" U40 (manufactured by Toray Industries, Inc., thickness: 50 µm) using a slit die coater and was heated and dried at 100° C. for 1 hour to form a color conversion layer with an average film thickness of 10 µm. Next, "Lumirror" U40 (thickness: 50 µm) was overlaid on the color conversion layer and was laminated by heating at 90° C. in a vacuum condition to prepare a color conversion sheet with a structure similar to that of the color conversion sheet 1 illustrated in FIG. 2.

Blue LED light was subjected to color conversion using this color conversion sheet; when only the emission region of red light was extracted, high color purity red emission with a peak wavelength of 635 nm and with a full width at half maximum of an emission spectrum at the peak wavelength being 49 nm was obtained. When the color conversion sheet was continuously irradiated with the light from the blue LED element at room temperature, the time elapsed until the luminance decreased by 2% was 210 hours. An evaluation result of Example 39 is listed in Table 6 below.

Examples 40 to 46 and Comparative Examples 24 to 27

In Examples 40 to 46 of the present invention and Comparative Examples 24 to 27 against the present invention, color conversion sheets were prepared and evaluated similarly to Example 39 except that light-emitting materials (Compounds R-1, R-2, R-3, and R-4) listed in Table 7 were used as Component (A), and resins (Bisphenol Resins F11 and F12 and Acrylic Resin F22) listed in Table 7 were used as Component (B). Evaluation results of Examples 40 to 46 and Comparative Examples 24 to 27 are listed in Table 7.

Example 47

In Example 47 of the present invention, a color conversion sheet was prepared and evaluated similarly to Example 39 except that a resin (a 1:1 mixture of Bisphenol Resin F11 and Polyester Resin F1) listed in Table 7 was used as Component (B). An evaluation result of Example 47 is listed in Table 7.

Example 48

In Example 48 of the present invention, using Bisphenol Resin F11 (refer to Table 2) as Component (B), 0.20 part by weight of Compound G-1 as Light-Emitting Material (a) of Component (A), 0.08 part by weight of Compound R-1 as Light-Emitting Material (b) of Component (A), and 200 parts by weight of methyl ethyl ketone as a solvent were mixed with 100 parts by weight of Component (B), and the resultant mixture was stirred and defoamed at 300 rpm for 20 minutes using a planetary stirring and defoaming apparatus "Mazerustar KK-400" (manufactured by Kurabo Industries Ltd.) to obtain a color conversion composition as a resin liquid for sheer, preparation.

Next, the resin liquid for sheet preparation was applied to "Lumirror" U40 (manufactured by Toray Industries, Inc., thickness: 50 nm) using a slit die coater and was heated and dried at 100° C. for 1 hour to form a color conversion layer with an average film thickness of 10 µm. Next, "Lumirror" U40 (thickness: 50 µm) was overlaid on the color conversion layer and was laminated by heating at 90° C. in a vacuum condition to prepare a color conversion sheet with a structure similar to that of the color conversion sheet 1 illustrated in FIG. 2.

Blue LED light was subjected to color conversion using this color conversion sheet; when only the emission region of green light was extracted, high color purity green emission with a peak, wavelength of 527 nm and with a full width at half maximum of an emission spectrum at the peak wavelength being 28 nm was obtained; when only the emission region of red light was extracted, high color purity red emission with a peak wavelength of 635 nm and with a full width at half maximum of an emission spectrum at the peak wavelength being 49 nm was obtained. When the color conversion sheet was continuously irradiated with the light from the blue LED element at room temperature, the time elapsed until the luminance decreased by 5% was 200 hours. An evaluation result of Example 48 is listed in Table 8 below.

Examples 49 to 59 and Comparative Examples 28 to 33

In Examples 49 to 59 of the present invention and Comparative Examples 23 to 33 against the present invention, color conversion sheets were prepared and evaluated similarly to Example 48 except that Light-Emitting Material (a) (Compounds G-1, G-2, G-3, and G-5) and Light-Emitting Material (b) (Compounds R-1, R-2, and R-3) listed in Table 8 were used as Component (A), and resins (Bisphenol Resins F11 and F12 and Acrylic Resin F22) listed in Table 8 were used as Component (B). Evaluation results of Examples 49 to 59 and Comparative Examples 28 to 33 are listed in Table 8.

Example 60

In Example 60 of the present invention, a color conversion sheet was prepared and evaluated similarly to Example 48 except that a resin (a 1:1 mixture of Bisphenol Resin F11 and Polyester Resin F1) listed in Table 8 was used as Component (B). An evaluation result of Example 60 is listed in Table 8.

TABLE 3

| | Light-emitting material | Resin | Peak wavelength (nm) | Full width at half maximum (nm) | Light-fastness (h) |
|---|---|---|---|---|---|
| Example 1 | G-1 | Polyester Resin F1 | 530 | 26 | 320 |
| Example 2 | G-2 | Polyester Resin F1 | 530 | 26 | 300 |
| Example 3 | G-3 | Polyester Resin F1 | 530 | 26 | 270 |
| Example 4 | G-4 | Polyester Resin F1 | 493 | 55 | 180 |
| Example 5 | G-5 | Polyester Resin F1 | 534 | 47 | 240 |
| Example 6 | G-1 | Polyester Resin F2 | 530 | 26 | 320 |
| Example 7 | G-1 | Polyester Resin F3 | 530 | 26 | 290 |
| Example 8 | G-1 | Polyester Resin F4 | 530 | 26 | 190 |
| Example 9 | G-1 | Polyester Resins F1 and F3 (1:1) | 530 | 26 | 310 |
| Comparative Example 1 | G-1 | Acrylic Resin F21 | 526 | 26 | 20 |
| Comparative Example 2 | G-2 | Acrylic Resin F21 | 526 | 26 | 19 |
| Comparative Example 3 | G-3 | Acrylic Resin F21 | 527 | 26 | 18 |
| Comparative Example 4 | G-4 | Acrylic Resin F21 | 490 | 55 | 30 |
| Comparative Example 5 | G-5 | Acrylic Resin F21 | 530 | 47 | 80 |
| Comparative Example 6 | G-1 | Acrylic Resin F5 | 529 | 26 | 30 |

TABLE 4

| | Light-emitting material | Resin | Peak wavelength (nm) | Full width at half maximum (nm) | Light-fastness (h) |
|---|---|---|---|---|---|
| Example 10 | R-1 | Polyester Resin F1 | 635 | 49 | 340 |
| Example 11 | R-2 | Polyester Resin F1 | 617 | 47 | 330 |
| Example 12 | R-3 | Polyester Resin F1 | 638 | 48 | 290 |
| Example 13 | R-4 | Polyester Resin F1 | 647 | 30 | 100 |
| Example 14 | R-1 | Polyester Resin F2 | 635 | 49 | 340 |
| Example 15 | R-1 | Polyester Resin F3 | 635 | 49 | 300 |
| Example 16 | R-1 | Polyester Resin F4 | 635 | 49 | 170 |
| Example 17 | R-1 | Polyester Resin F1 and F3 (1:1) | 635 | 49 | 320 |
| Comparative Example 7 | R-1 | Acrylic Resin F21 | 633 | 49 | 100 |
| Comparative Example 8 | R-2 | Acrylic Resin F21 | 615 | 47 | 95 |
| Comparative Example 9 | R-3 | Acrylic Resin F21 | 636 | 48 | 93 |
| Comparative Example 10 | R-4 | Acrylic Resin F21 | 645 | 30 | 74 |
| Comparative Example 11 | R-1 | Acrylic Resin F5 | 634 | 49 | 120 |

TABLE 5

| | Light-emitting material | | Resin | Peak wavelength (nm) | Full width at half maximum (nm) | Light-fastness (h) |
|---|---|---|---|---|---|---|
| | (a) | (b) | | | | |
| Example 18 | G-1 | R-1 | Polyester Resin F1 | 530, 635 | 28, 49 | 330 |
| Example 19 | G-1 | R-2 | Polyester Resin F1 | 530, 617 | 28, 48 | 320 |
| Example 20 | G-1 | R-3 | Polyester Resin F1 | 530, 638 | 28, 48 | 320 |
| Example 21 | G-2 | R-1 | Polyester Resin F1 | 530, 635 | 28, 49 | 310 |
| Example 22 | G-3 | R-1 | Polyester Resin F1 | 530, 635 | 28, 49 | 280 |
| Example 23 | G-4 | R-1 | Polyester Resin F1 | 493, 635 | 56, 49 | 180 |
| Example 24 | G-1 | R-1 | Polyester Resin F2 | 530, 635 | 28, 49 | 320 |
| Example 25 | G-1 | R-1 | Polyester Resin F3 | 530, 635 | 28, 49 | 290 |
| Example 26 | G-1 | R-1 | Polyester Resin F4 | 530, 635 | 28, 49 | 180 |
| Example 27 | G-1 | R-1 | Polyester Resins F1 and F3 (1:1) | 530, 635 | 28, 49 | 310 |
| Comparative Example 12 | G-1 | R-1 | Acrylic Resin F21 | 526, 633 | 28, 49 | 21 |
| Comparative Example 13 | G-1 | R-2 | Acrylic Resin F21 | 526, 615 | 28, 48 | 20 |
| Comparative Example 14 | G-1 | R-3 | Acrylic Resin F21 | 526, 636 | 28, 48 | 20 |

TABLE 5-continued

|  | Light-emitting material | | Resin | Peak wavelength (nm) | Full width at half maximum (nm) | Light-fastness (h) |
|---|---|---|---|---|---|---|
|  | (a) | (b) | | | | |
| Comparative Example 15 | G-2 | R-1 | Acrylic Resin F21 | 526, 633 | 28, 49 | 20 |
| Comparative Example 16 | G-3 | R-1 | Acrylic Resin F21 | 527, 633 | 28, 49 | 18 |
| Comparative Example 17 | G-4 | R-1 | Acrylic Resin F21 | 490, 633 | 56, 49 | 31 |
| Comparative Example 18 | G-1 | R-1 | Polyester Resin F5 | 529, 634 | 28, 49 | 32 |

TABLE 6

|  | Light-emitting material | Resin | Peak wavelength (nm) | Full width at half maximum (nm) | Light-fastness (h) |
|---|---|---|---|---|---|
| Example 28 | G-1 | Bisphenol Resin F11 | 526 | 25 | 210 |
| Example 29 | G-2 | Bisphenol Resin F11 | 526 | 25 | 200 |
| Example 30 | G-3 | Bisphenol Resin F11 | 527 | 25 | 160 |
| Example 31 | G-4 | Bisphenol Resin F11 | 511 | 35 | 70 |
| Example 32 | G-5 | Bisphenol Resin F11 | 490 | 55 | 140 |
| Example 33 | G-1 | Bisphenol Resin F12 | 526 | 25 | 200 |
| Example 34 | G-2 | Bisphenol Resin F12 | 526 | 25 | 200 |
| Example 35 | G-3 | Bisphenol Resin F12 | 527 | 25 | 150 |
| Example 36 | G-4 | Bisphenol Resin F12 | 511 | 35 | 70 |
| Example 37 | G-5 | Bisphenol Resin F12 | 490 | 55 | 130 |
| Example 38 | G-1 | Bisphenol Resin F11 and Polyester Resin F1 (1:1) | 528 | 26 | 230 |
| Comparative Example 19 | G-1 | Acrylic Resin F22 | 526 | 25 | 19 |
| Comparative Example 20 | G-2 | Acrylic Resin F22 | 526 | 25 | 18 |
| Comparative Example 21 | G-3 | Acrylic Resin F22 | 527 | 25 | 16 |
| Comparative Example 22 | G-4 | Acrylic Resin F22 | 511 | 35 | 18 |
| Comparative Example 23 | G-5 | Acrylic Resin F22 | 490 | 55 | 29 |

TABLE 7

|  | Light-emitting material | Resin | Peak wavelength (nm) | Full width at half maximum (nm) | Light-fastness (h) |
|---|---|---|---|---|---|
| Example 39 | R-1 | Bisphenol Resin F11 | 635 | 49 | 210 |
| Example 40 | R-2 | Bisphenol Resin F11 | 617 | 47 | 180 |
| Example 41 | R-3 | Bisphenol Resin F11 | 638 | 48 | 170 |
| Example 42 | R-4 | Bisphenol Resin F11 | 647 | 30 | 70 |
| Example 43 | R-1 | Bisphenol Resin F12 | 635 | 49 | 200 |
| Example 44 | R-2 | Bisphenol Resin F12 | 617 | 47 | 180 |
| Example 45 | R-3 | Bisphenol Resin F12 | 638 | 48 | 160 |
| Example 46 | R-4 | Bisphenol Resin F12 | 647 | 30 | 70 |
| Example 47 | R-1 | Bisphenol Resin F11 and Polyester Resin F1 (1:1) | 635 | 49 | 220 |
| Comparative Example 24 | R-1 | Acrylic Resin F22 | 635 | 49 | 100 |
| Comparative Example 25 | R-2 | Acrylic Resin F22 | 617 | 47 | 94 |
| Comparative Example 26 | R-3 | Acrylic Resin F22 | 638 | 48 | 91 |
| Comparative Example 27 | R-4 | Acrylic Resin F22 | 647 | 30 | 75 |

TABLE 8

| | Light-emitting material (a) | Light-emitting material (b) | Resin | Peak wavelength (nm) | Full width at half maximum (nm) | Light-fastness (h) |
|---|---|---|---|---|---|---|
| Example 48 | G-1 | R-1 | Bisphenol Resin F11 | 527, 635 | 28, 49 | 200 |
| Example 49 | G-1 | R-2 | Bisphenol Resin F11 | 527, 628 | 28, 48 | 190 |
| Example 50 | G-1 | R-3 | Bisphenol Resin F11 | 527, 638 | 28, 48 | 180 |
| Example 51 | G-2 | R-1 | Bisphenol Resin F11 | 527, 635 | 28, 49 | 165 |
| Example 52 | G-3 | R-1 | Bisphenol Resin F11 | 528, 635 | 28, 49 | 150 |
| Example 53 | G-5 | R-1 | Bisphenol Resin F11 | 490, 635 | 56, 49 | 110 |
| Example 54 | G-1 | R-1 | Bisphenol Resin F12 | 527, 635 | 28, 49 | 190 |
| Example 55 | G-1 | R-2 | Bisphenol Resin F12 | 527, 628 | 28, 48 | 180 |
| Example 56 | G-1 | R-3 | Bisphenol Resin F12 | 527, 638 | 28, 48 | 170 |
| Example 57 | G-2 | R-1 | Bisphenol Resin F12 | 527, 635 | 28, 49 | 150 |
| Example 58 | G-3 | R-1 | Bisphenol Resin F12 | 528, 635 | 28, 49 | 140 |
| Example 59 | G-5 | R-1 | Bisphenol Resin F12 | 490, 635 | 56, 49 | 100 |
| Example 60 | G-1 | R-1 | Bisphenol Resin F11 and Polyester Resin F1 (1:1) | 529, 635 | 28, 49 | 210 |
| Comparative Example 28 | G-1 | R-1 | Acrylic Resin F22 | 527, 635 | 28, 49 | 21 |
| Comparative Example 29 | G-1 | R-2 | Acrylic Resin F22 | 527, 628 | 28, 48 | 20 |
| Comparative Example 30 | G-1 | R-3 | Acrylic Resin F22 | 527, 638 | 28, 48 | 20 |
| Comparative Example 31 | G-2 | R-1 | Acrylic Resin F22 | 527, 635 | 28, 49 | 20 |
| Comparative Example 32 | G-3 | R-1 | Acrylic Resin F22 | 528, 635 | 28, 49 | 18 |
| Comparative Example 33 | G-5 | R-1 | Acrylic Resin F22 | 490, 635 | 56, 49 | 31 |

INDUSTRIAL APPLICABILITY

As described above, the color conversion composition, the color conversion sheet and the light source unit including the same, the display, the lighting apparatus, the backlight unit, the LED chip, and the LED package according to the present invention are suitable for a color conversion composition, a color conversion sheet and a light source unit including the same, a display, a lighting apparatus, a backlight unit, an LED chip, and an LED package that achieve both high color reproducibility and high durability.

REFERENCE SIGNS LIST

1 Color conversion sheet
10 Base layer
11 Color conversion layer
12 Barrier film
21 LED chip
22 Color conversion sheet
23 Electrode
24 Color conversion composition
25 Reflector
26 Transparent sealant
27 Mounting substrate
28 Gold bump
29 Transparent adhesive
30 Base
31 Formed object
32 LED package

The invention claimed is:

1. A color conversion composition that converts incident light into light with a wavelength longer than that of the incident light, the color conversion composition comprising the following Component (A) and Component (B):

Component (A): an organic light-emitting material; and
Component (B): at least one of a polyester resin having a partial structure represented by General Formula (1) in a molecular structure of the polyester resin and a resin containing a bisphenol structure represented by General Formula (2):

  (1)

where Y is a divalent saturated aliphatic hydrocarbon group having at least one of a tertiary carbon and a quaternary carbon, and

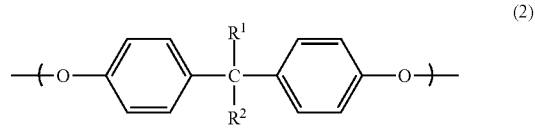  (2)

where $R^1$ and $R^2$ each represents hydrogen or a $C_{1-20}$ organic group; $R^1$ and $R^2$ are the same as or different from each other,
wherein when a weight ratio of the partial structure represented by the General Formula (1) to a total amount of the polyester resin contained as the Component (B) is represented as $m_1\%$ by weight, $m_1$ satisfies $10 \leq m_1 \leq 60$.

2. The color conversion composition according to claim 1, wherein the polyester resin has at least one of a partial structure represented by General Formula (3) and a partial structure represented by General Formula (4) in the molecular structure of the polyester resin:

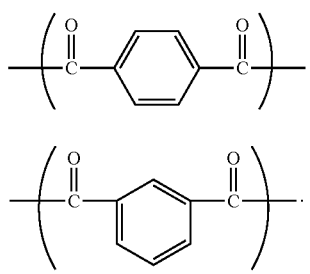

3. The color conversion composition according to claim 2, wherein the polyester resin has at least the partial structure represented by the General Formula (3) in the molecular structure of the polyester resin, and when a weight ratio of the partial structure represented by the General Formula (3) to a total amount of the polyester resin contained as the Component (B) is represented as $m_2$% by weight, $m_2$ satisfies $20 \leq m_2 \leq 70$.

4. The color conversion composition according to claim 2, wherein when a weight ratio of the partial structure represented by the General Formula (3) to a total amount of the polyester resin contained as the Component (B) is represented as $m_2$% by weight, and a weight ratio of the partial structure represented by the General Formula (4) to a total amount of the polyester resin contained as the Component (B) is represented as $m_3$% by weight, $m_2$ and $m_3$ satisfy $20 \leq m_2 + m_3 \leq 70$.

5. The color conversion composition according to claim 1, wherein the polyester resin has at least one of a partial structure represented by General Formula (5) and a partial structure represented by General Formula (6) in a molecular structure of the polyester resin:

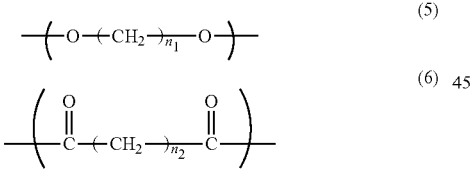

where $n_1$ and $n_2$ are natural numbers, in which $2 \leq n_1 \leq 10$ and $2 \leq n_2 \leq 14$.

6. The color conversion composition according to claim 1, wherein the resin containing the bisphenol structure has at least a structure represented by General Formula (7) in a molecular structure of the resin:

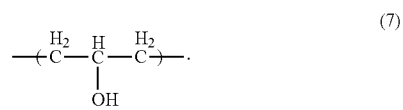

7. The color conversion composition according to claim 1, wherein the Component (A) contains a compound represented by General Formula (8):

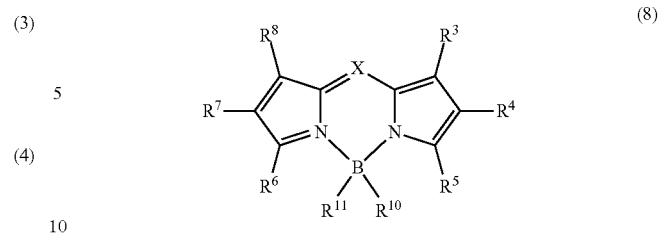

where X is C—$R^9$ or N; $R^3$ to $R^{11}$ are the same as or different from each other and are selected from hydrogen, an alkyl group, a cycloalkyl group, a heterocyclic group, an alkenyl group, a cycloalkenyl group, an alkynyl group, a hydroxy group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a boryl group, a phosphine oxide group, and a condensed ring and an aliphatic ring formed between adjacent substituents.

8. The color conversion composition according to claim 7, wherein X in the General Formula (8) is C—$R^9$ in which $R^9$ is a group represented by General Formula (9):

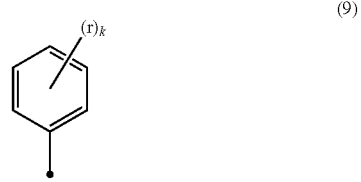

where r is selected from the group consisting of hydrogen, an alkyl group, a cycloalkyl group, a heterocyclic group, an alkenyl group, a cycloalkenyl group, an alkynyl group, a hydroxy group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a boryl group, and a phosphine oxide group; k is an integer of 1 to 3; when k is 2 or more, rs are the same as or different from each other.

9. The color conversion composition according to claim 7, wherein $R^3$, $R^5$, $R^6$, and $R^8$ in the General Formula (8) are the same as or different from each other, and $R^3$, $R^5$, $R^6$, and $R^8$ in the General Formula (8) are substituted or unsubstituted phenyl groups or are substituted or unsubstituted alkyl groups.

10. The color conversion composition according to claim 1, wherein the Component (A) contains a light-emitting material that exhibits light emission with a peak wavelength observed in a region of 500 nm or more and 580 nm or less by using excitation light in a wavelength range of 400 nm or more and 500 nm or less.

11. The color conversion composition according to claim 1, wherein the Component (A) contains the following Light-Emitting Material (a) and Light-Emitting Material (b):

Light-Emitting Material (a): a light-emitting material that exhibits light emission with a peak wavelength observed in a region of 500 nm or more and 580 nm or less by using excitation light in a wavelength range of 400 nm or more and 500 nm or less, and Light-Emitting Material (b): a light-emitting material that exhibits light emission with a peak wavelength observed in a region of 580 nm or more and 750 nm or less by being excited by at least either excitation light in a wavelength range of 400 nm or more and 500 nm or less or light emission from the Light-Emitting Material (a).

12. The color conversion composition according to claim 11, wherein a content $w_a$ of the Light-Emitting Material (a) and a content $w_b$ of the Light-Emitting Material (b) have a relation of $w_a \geq w_b$.

13. The color conversion composition according to claim 10, wherein
the Component (A) contains a compound represented by General Formula (8):

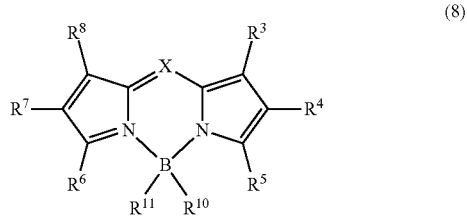

(8)

where X is C—$R^9$ or N; $R^3$ to $R^{11}$ are the same as or different from each other and are selected from hydrogen, an alkyl group, a cycloalkyl group, a heterocyclic group, an alkenyl group, a cycloalkenyl group, an alkynyl group, a hydroxy group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a boryl group, a phosphine oxide group, and a condensed ring and an aliphatic ring formed between adjacent substituents, and the light-emitting material that exhibits light emission with a peak wavelength of 500 nm or more and 580 nm or less by using the excitation light in a wavelength range of 400 nm or more and 500 nm or less is the compound represented by the General Formula (8).

14. The color conversion composition according to claim 11, wherein
the Component (A) contains a compound represented by General Formula (8):

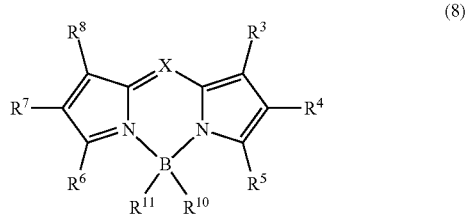

(8)

where X is C—$R^9$ or N; $R^3$ to $R^{11}$ are the same as or different from each other and are selected from hydro-gen, an alkyl group, a cycloalkyl group, a heterocyclic group, an alkenyl group, a cycloalkenyl group, an alkynyl group, a hydroxy group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a boryl group, a phosphine oxide group, and a condensed ring and an aliphatic ring formed between adjacent substituents, and the Light-Emitting Material (b) is the compound represented by the General Formula (8).

15. A color conversion sheet comprising a layer of the color conversion composition according to claim 1 or a layer of a cured object of the color conversion composition according to claim 1.

16. The color conversion sheet according to claim 15, further comprising a barrier layer.

17. A light source unit comprising:
a light source; and
the color conversion sheet according to claim 2.

18. The light source unit according to claim 17, wherein the light source is a light-emitting diode having maximum emission in a range of 400 nm or more and 500 nm or less.

19. A display or a lighting apparatus comprising the light source unit according to claim 17.

20. An LED chip comprising a light-emitting face provided with the color conversion sheet according to claim 15.

21. An LED package comprising a cured object of the color conversion composition according to claim 1.

22. A backlight unit or a display or a lighting apparatus comprising the LED package according to claim 21.

23. The color conversion composition according to claim 11, wherein
the Component (A) contains a compound represented by General Formula (8):

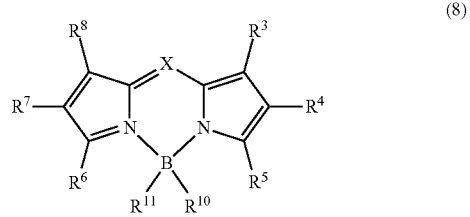

(8)

where X is C—$R^9$ or N; $R^3$ to $R^{11}$ are the same as or different from each other and are selected from hydrogen, an alkyl group, a cycloalkyl group, a heterocyclic group, an alkenyl group, a cycloalkenyl group, an alkynyl group, a hydroxy group, a thiol group, an alkoxy group, an alkylthio group, an aryl ether group, an aryl thioether group, an aryl group, a heteroaryl group, halogen, a cyano group, an aldehyde group, a carbonyl group, a carboxy group, an oxycarbonyl group, a carbamoyl group, an amino group, a nitro group, a silyl group, a siloxanyl group, a boryl group, a phosphine oxide group, and a condensed ring and an aliphatic ring formed between adjacent substituents, and the light-emitting material that exhibits light emission with a peak wavelength of 500 nm or more and 580 nm or less by using the excitation light in a wavelength range of 400 nm or more and 500 nm or less is the compound represented by the General Formula (8).

24. An LED package comprising the color conversion sheet according to claim 15.

* * * * *